United States Patent
Yen et al.

(10) Patent No.: US 10,693,074 B2
(45) Date of Patent: Jun. 23, 2020

(54) 5,12-DIHYDROTETRACENE DERIVATIVE AND ORGANIC ELECTROLUMINESCENCE DEVICE USING THE SAME

(71) Applicants: Feng-Wen Yen, Taipei (TW); Li-Chieh Chuang, Hsinchu (TW)

(72) Inventors: Feng-Wen Yen, Taipei (TW); Li-Chieh Chuang, Hsinchu (TW)

( * ) Notice: Subject to any disclaimer, the term of this patent is extended or adjusted under 35 U.S.C. 154(b) by 295 days.

(21) Appl. No.: 15/879,458

(22) Filed: Jan. 25, 2018

(65) Prior Publication Data
US 2019/0229270 A1    Jul. 25, 2019

(51) Int. Cl.
| | | |
|---|---|---|
| H01L 51/50 | (2006.01) | |
| H01L 51/00 | (2006.01) | |
| C09K 11/06 | (2006.01) | |
| C07C 13/66 | (2006.01) | |
| C07D 409/10 | (2006.01) | |
| C07D 417/10 | (2006.01) | |
| C07D 409/14 | (2006.01) | |
| C07D 495/04 | (2006.01) | |

(Continued)

(52) U.S. Cl.
CPC .......... *H01L 51/0054* (2013.01); *C07C 13/66* (2013.01); *C07C 255/58* (2013.01); *C07D 209/86* (2013.01); *C07D 209/88* (2013.01); *C07D 215/12* (2013.01); *C07D 219/02* (2013.01); *C07D 239/26* (2013.01); *C07D 251/24* (2013.01); *C07D 253/06* (2013.01); *C07D 265/38* (2013.01); *C07D 333/58* (2013.01); *C07D 333/76* (2013.01); *C07D 401/10* (2013.01); *C07D 403/10* (2013.01); *C07D 403/14* (2013.01); *C07D 409/10* (2013.01); *C07D 409/14* (2013.01); *C07D 411/10* (2013.01); *C07D 413/10* (2013.01); *C07D 413/14* (2013.01); *C07D 417/10* (2013.01); *C07D 417/14* (2013.01); *C07D 495/04* (2013.01); *C07F 7/02* (2013.01); *C07F 7/0816* (2013.01); *C09K 11/06* (2013.01); *H01L 51/006* (2013.01); *H01L 51/0052* (2013.01); *H01L 51/0059* (2013.01); *H01L 51/0067* (2013.01); *H01L 51/0071* (2013.01); *H01L 51/0072* (2013.01); *H01L 51/0074* (2013.01); *H01L 51/5012* (2013.01); *C07C 2603/44* (2017.05); *C09K 2211/1011* (2013.01)

(58) Field of Classification Search
None
See application file for complete search history.

(56) References Cited

U.S. PATENT DOCUMENTS

2016/0163989 A1    6/2016    Yang et al.

OTHER PUBLICATIONS

Rafig et al., Synthesis of Annulated Arenes and Heteroarenes by Hydriodic Acid and Red Phosphorus Mediated Reductive Cyclization of 2-(Hetero)aroylbenzoic Acids or 3-(Hetero)arylphthalides, 2017, Synlett (2017), 28(3), 362-370 (Year: 2017).*

* cited by examiner

*Primary Examiner* — Gregory D Clark

(57) ABSTRACT

The present invention discloses a 5,12-dihydrotetracene derivative and an organic electroluminescence device employing the 5,12-dihydrotetracene derivative as the thermally activated delayed fluorescence host material or the thermally activated delayed fluorescence dopant material in the light emitting layer. The organic electroluminescence device of the present invention exhibits improved performance, such as reduced power consumption and increased current efficiency.

9 Claims, 1 Drawing Sheet

(51) Int. Cl.
*C07D 417/14* (2006.01)
*C07D 239/26* (2006.01)
*C07D 411/10* (2006.01)
*C07C 255/58* (2006.01)
*C07F 7/02* (2006.01)
*C07F 7/08* (2006.01)
*C07D 265/38* (2006.01)
*C07D 403/10* (2006.01)
*C07D 219/02* (2006.01)
*C07D 333/58* (2006.01)
*C07D 401/10* (2006.01)
*C07D 209/88* (2006.01)
*C07D 215/12* (2006.01)
*C07D 251/24* (2006.01)
*C07D 253/06* (2006.01)
*C07D 333/76* (2006.01)
*C07D 209/86* (2006.01)
*C07D 413/14* (2006.01)
*C07D 413/10* (2006.01)
*C07D 403/14* (2006.01)

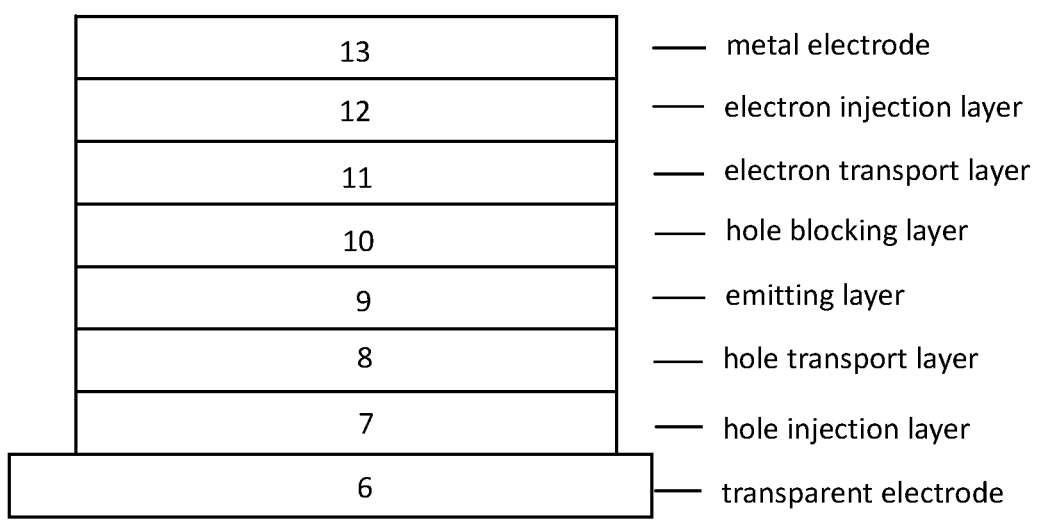

5,12-DIHYDROTETRACENE DERIVATIVE AND ORGANIC ELECTROLUMINESCENCE DEVICE USING THE SAME

FIELD OF INVENTION

The present invention relates to a 5,12-dihydrotetracene derivative and, more particularly, to an organic electroluminescence device using the 5,12-dihydrotetracene derivative.

BACKGROUND OF THE INVENTION

An organic electroluminescence (organic EL) device is an organic light-emitting diode (OLED) in which the light emitting layer is a film made from organic compound that emits light in response to an electric current. The organic EL device is applied to flat panel displays due to its high illumination, low weight, ultra-thin profile, self-illumination without back light, low power consumption, wide viewing angle, high contrast, simple fabrication methods and rapid response time.

The first diode device was reported by Ching W. Tang and Steven Van Slyke at Eastman Kodak in 1987. The device used a two-layer structure with separate hole transporting and electron transporting layers such that recombination and light emission occurred in the middle of the organic layer. This resulted in reduction of operating voltage and improvement of the efficiency, thereby leading to the current area of organic EL device research and device production.

Typically, the organic EL device is composed of organic material layers sandwiched between two electrodes. The organic material layers include the hole transporting layer, the light emitting layer, and the electron transporting layer. The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device.

In 2012, a new type of fluorescent organic EL device was developed by Adachi and coworkers. The new organic EL device incorporated the mechanism of thermally activated delayed fluorescence (TADF), which was a promising way to obtain a high percentage of singlet exciton formation by converting spin-forbidden triplet excitons up to the singlet level through the mechanism of reverse intersystem crossing (RISC). However, there still exists a need for the compound with TADF property to improve the performance of the organic EL devices.

SUMMARY OF THE INVENTION

Accordingly, an object of the present invention is to provide a novel compound with TADF property. The present invention discloses a 5,12-dihydrotetracene derivative and an organic EL device using the same, which can operate under reduced voltage and exhibit increased current efficiency.

Another object of the present invention is to provide a 5,12-dihydrotetracene derivative, which can be used as a TADF host material or a TADF dopant material in the emitting layer of an organic EL device to improve the power consumption and current efficiency.

The present invention has the economic advantages for industrial practice. Accordingly, a 5,12-dihydrotetracene derivative that can be used in organic EL devices is disclosed. The 5,12-dihydrotetracene derivative is represented by the following formula (1) or formula (2):

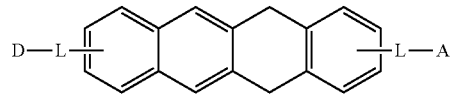

formula (1)

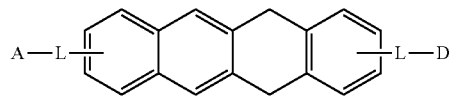

formula (2)

wherein L represents a single bond, a substituted or unsubstituted divalent arylene group having 6 to 30 ring carbon atoms, or a substituted or unsubstituted divalent heteroarylene group having 6 to 30 ring carbon atoms; D is an electron donor moiety selected from the group consisting of a substituted or unsubstituted carbazolyl group, a substituted or unsubstituted biscarbazolyl group, a substituted or unsubstituted dihydroacridine group, a substituted or unsubstituted phenoxazine group, and a substituted or unsubstituted diarylamine group; and A is an electron acceptor moiety selected from the following formulas:

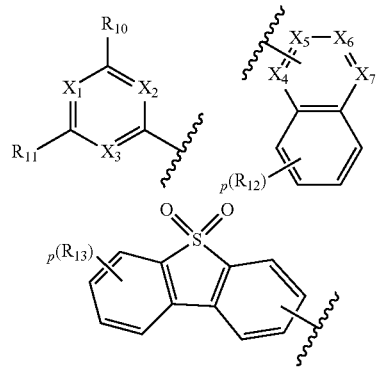

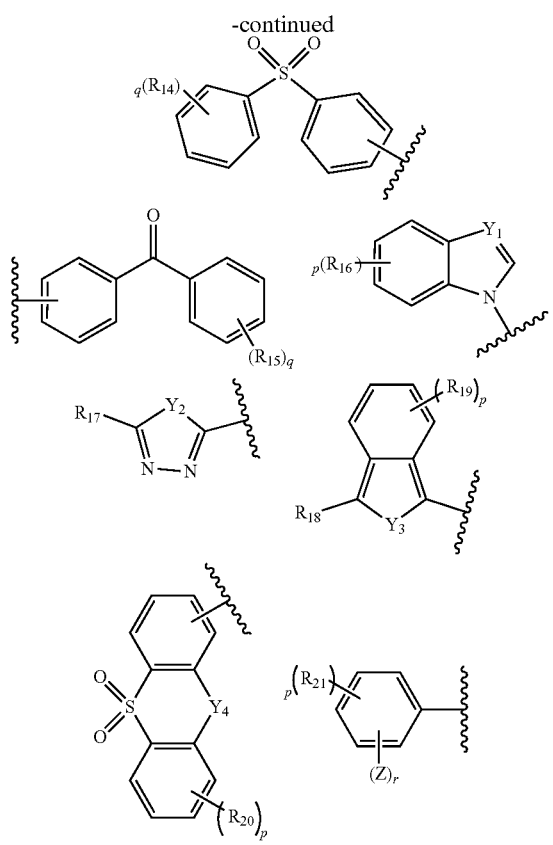

wherein p represents an integer of 0 to 4; q represents an integer of 0 to 5; r represents an integer of 1 to 4; $Y_1$ to $Y_4$ are each independently a divalent bridge selected from the group consisting of O, S, $C(R_{22})(R_{23})$, $NR_{24}$, and $Si(R_{25})(R_{26})$; $X_1$ to $X_7$ independently represent a nitrogen atom or $C(R_s)$, and each $R_s$ represents a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms; Z represents a cyano group or a fluorine atom; and $R_{10}$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

The present invention further discloses an organic electroluminescence device. The organic electroluminescence device comprises a pair of electrodes composed of a cathode and an anode, and a light emitting layer between the pair of electrodes. The light emitting layer comprises the 5,12-dihydrotetracene derivative of formula (1) or formula (2).

BRIEF DESCRIPTION OF THE DRAWINGS

The FIGURE shows one embodiment of the organic EL device of the present invention. In the device, hole injection layer 7 is deposited onto transparent electrode 6, hole transport layer 8 is deposited onto hole injection layer 7, fluorescence or phosphorescence emitting layer 9 is deposited onto hole transport layer 8, hole blocking layer 10 is deposited onto emitting layer 9, electron transport layer 11 is deposited onto hole blocking layer 10, electron injection layer 12 is deposited onto electron transport layer 11, and metal electrode 13 is deposited onto electron injection layer 12.

DESCRIPTION OF THE PREFERRED EMBODIMENTS

What probed into the invention is the 5,12-dihydrotetracene derivative and the organic EL device using the 5,12-dihydrotetracene derivative. Detailed descriptions of the production, structure and elements will be provided as follows such that the invention can be fully understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail as follows. However, it should be understood that the present invention can be practiced in a wide range of other embodiments besides those explicitly described, that is, this invention can also be applied extensively to other embodiments, and the scope of the present invention is definitely not limited except as specified in the accompanying claims.

In one embodiment of the present invention, a 5,12-dihydrotetracene derivative, which can be used as a thermally activated delayed fluorescence host material or a thermally activated delayed fluorescence dopant material in a light emitting layer of an organic EL device, is disclosed. The 5,12-dihydrotetracene derivative is represented by the following formula (1) or formula (2):

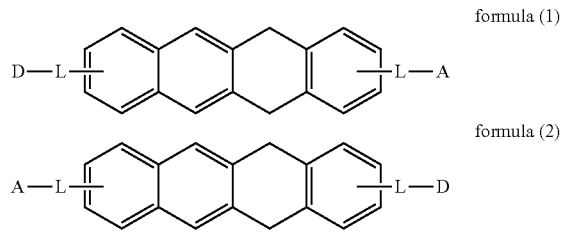

wherein L represents a single bond, a substituted or unsubstituted divalent arylene group having 6 to 30 ring carbon atoms, or a substituted or unsubstituted divalent heteroarylene group having 6 to 30 ring carbon atoms; D is an electron donor moiety selected from the group consisting of a substituted or unsubstituted carbazolyl group, a substituted or unsubstituted biscarbazolyl group, a substituted or unsubstituted dihydroacridine group, a substituted or unsubstituted phenoxazine group, and a substituted or unsubstituted diarylamine group; and A is an electron acceptor moiety selected from the following formulas:

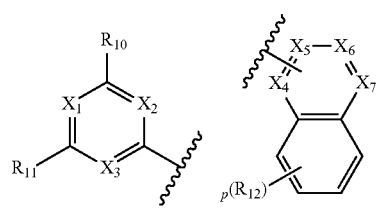

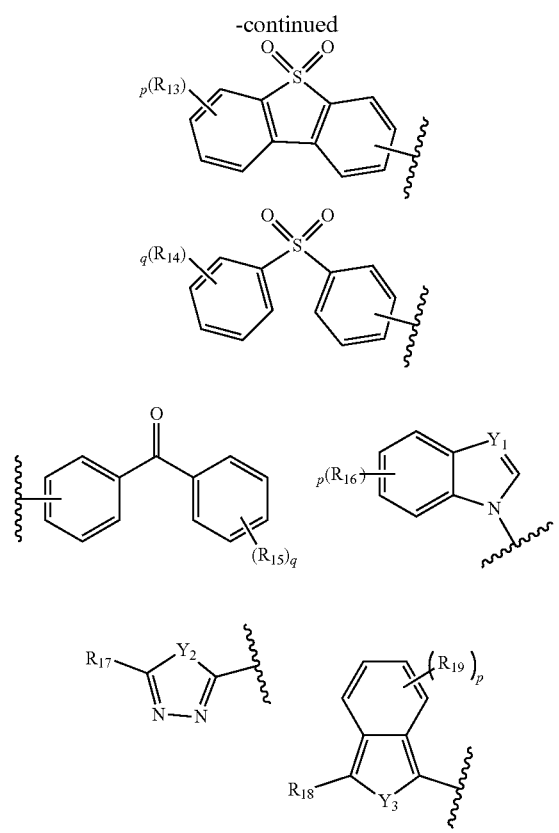

wherein p represents an integer of 0 to 4; q represents an integer of 0 to 5; r represents an integer of 1 to 4; $Y_1$ to $Y_4$ are each independently a divalent bridge selected from the group consisting of O, S, $C(R_{22})(R_{23})$, $NR_{24}$, and $Si(R_{25})(R_{26})$; $X_1$ to $X_7$ independently represent a nitrogen atom or $C(R_s)$, and each $R_s$ represents a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms; Z represents a cyano group or a fluorine atom; and $R_{10}$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

Preferably, the 5,12-dihydrotetracene derivative is one of the following compounds:

Compound 3
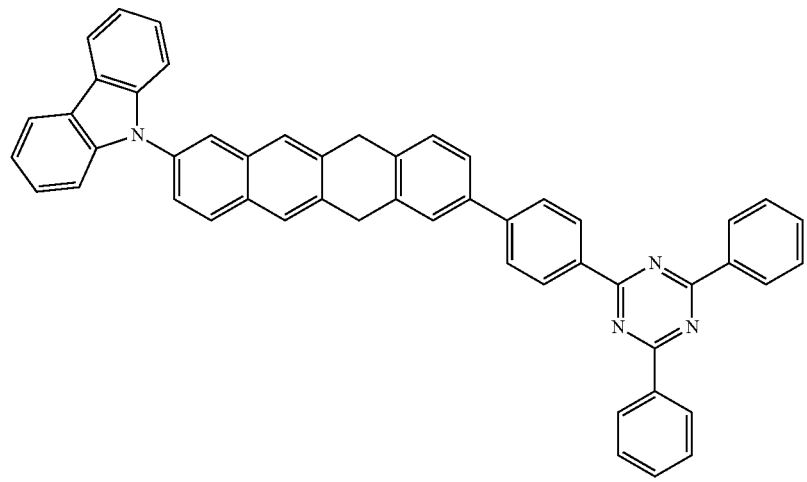
Compound 4
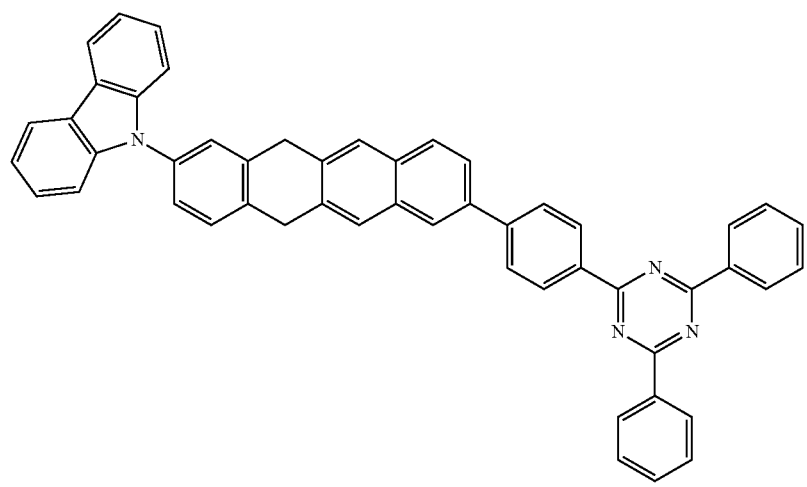
Compound 5
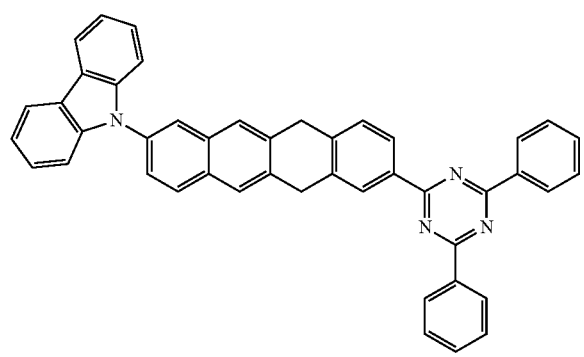
Compound 6
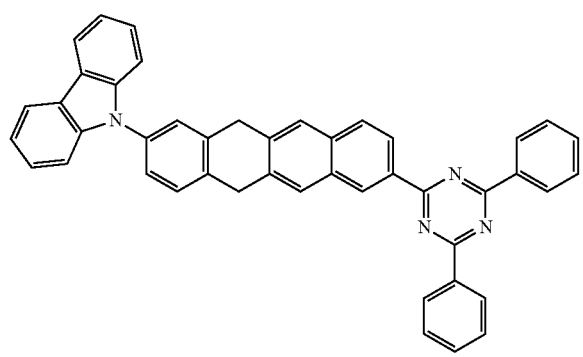

-continued
Compound 7
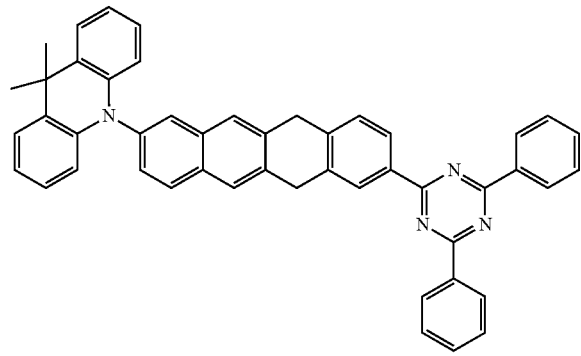
Compound 8
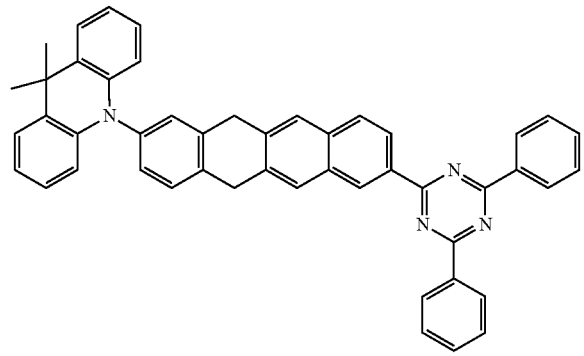
Compound 9
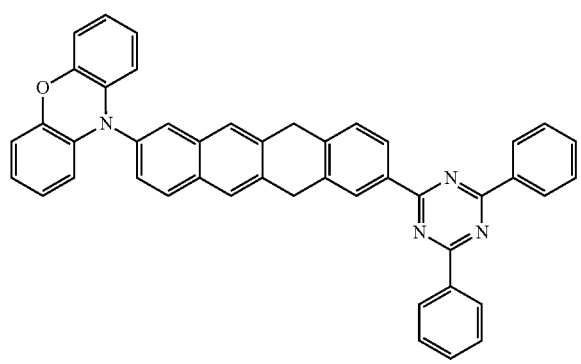
Compound 10
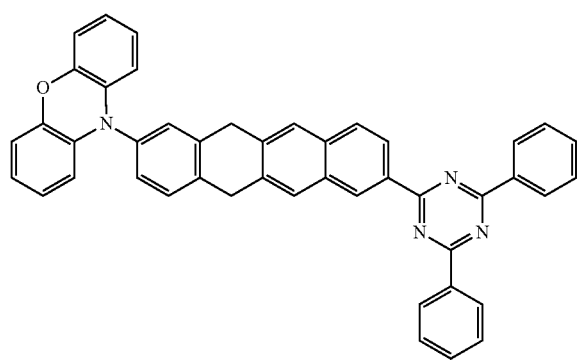
Compound 11
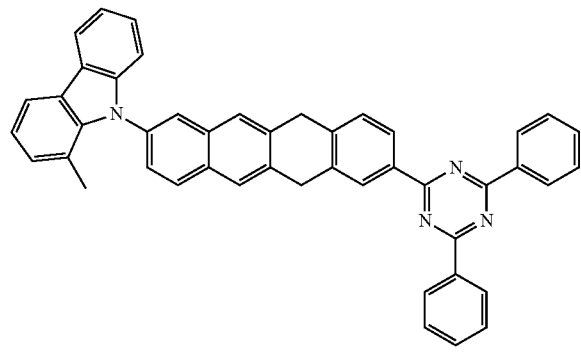
Compound 12
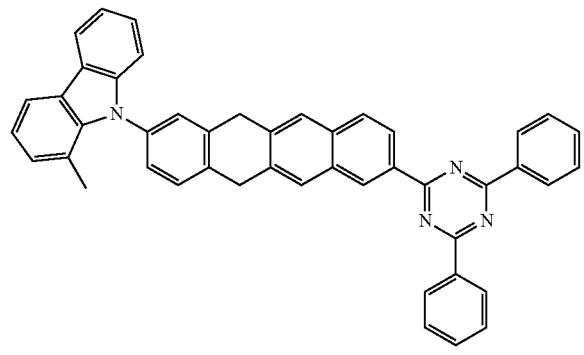
Compound 13
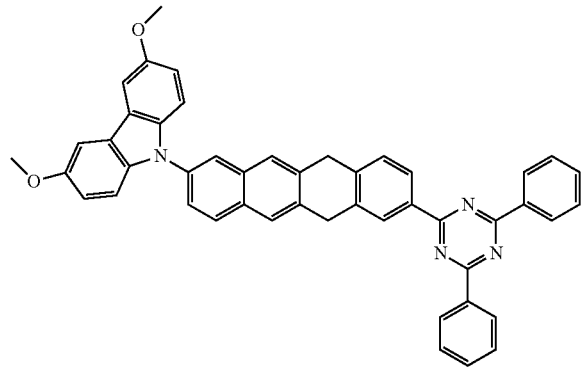
Compound 14
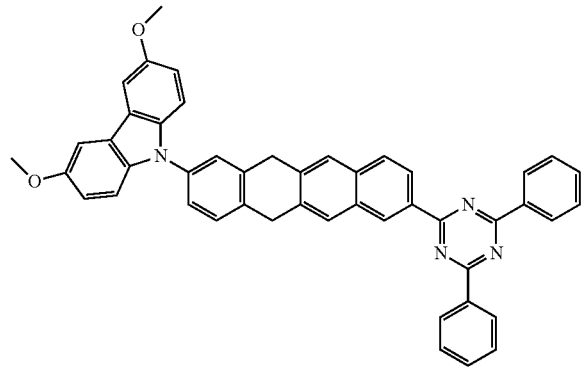

-continued
Compound 15
Compound 16
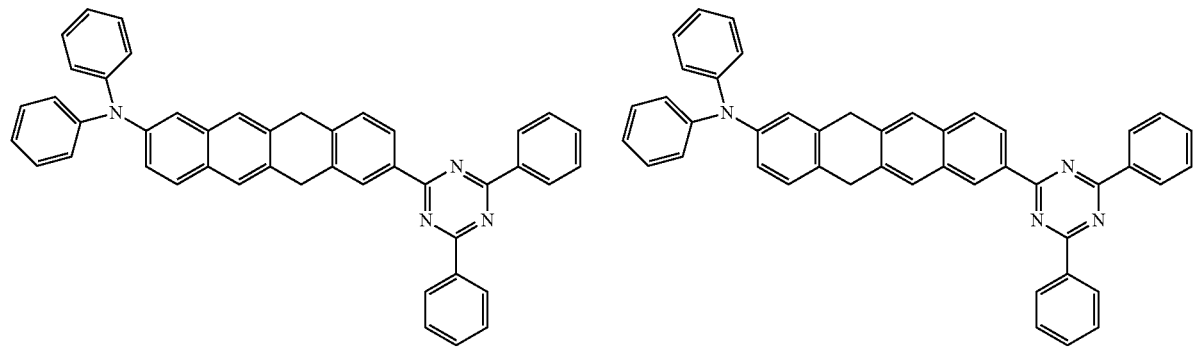
Compound 17
Compound 18
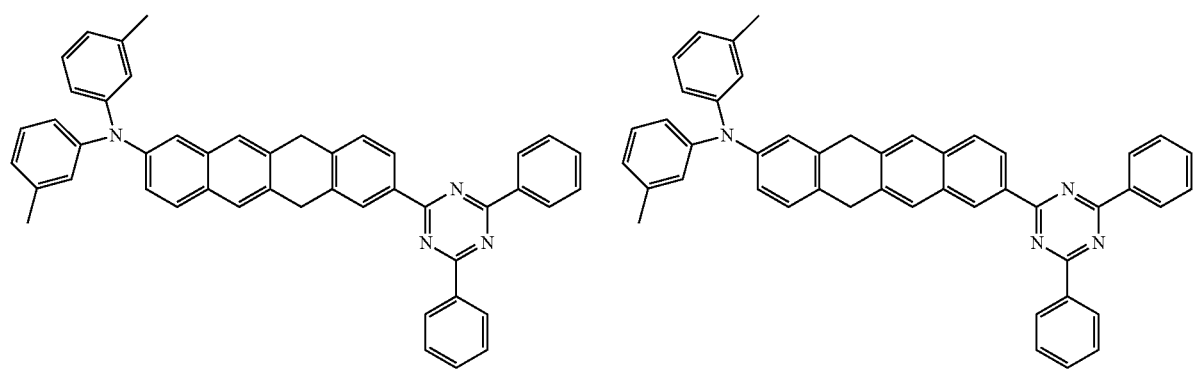
Compound 19
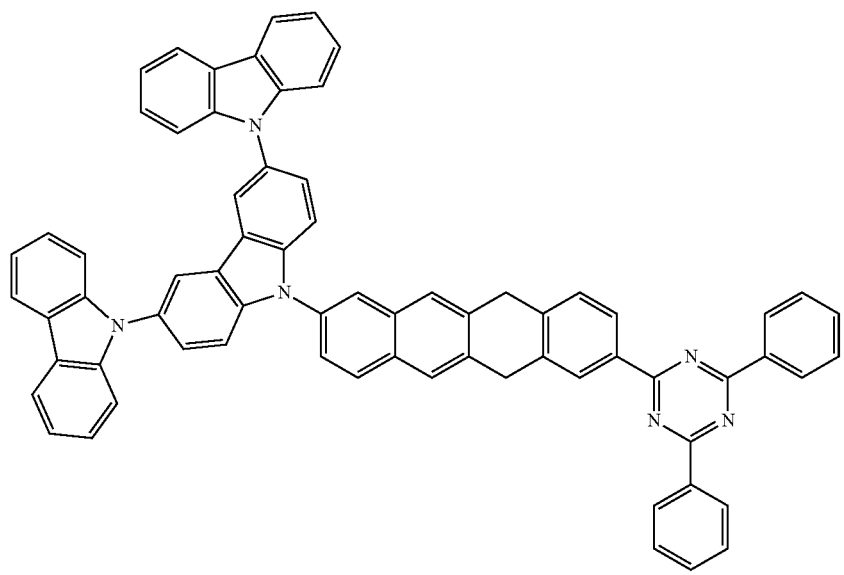

-continued
Compound 20
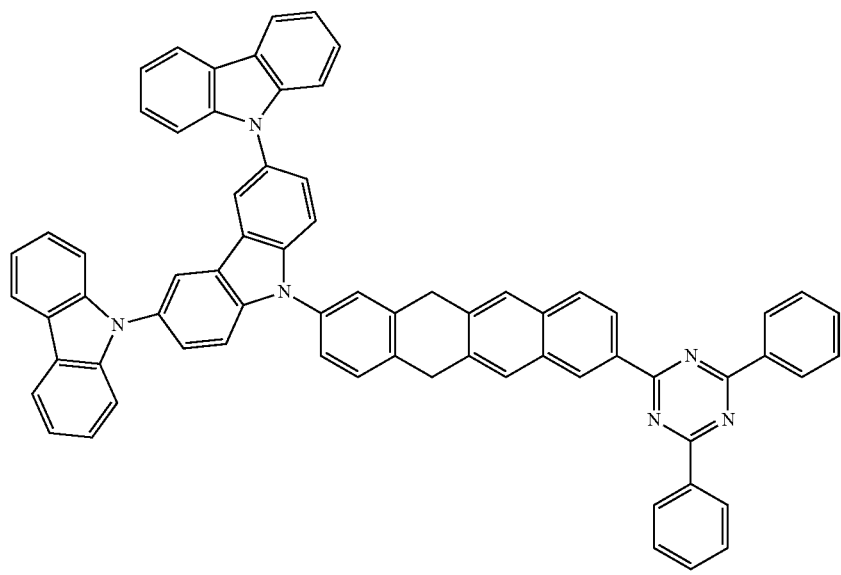
Compound 21
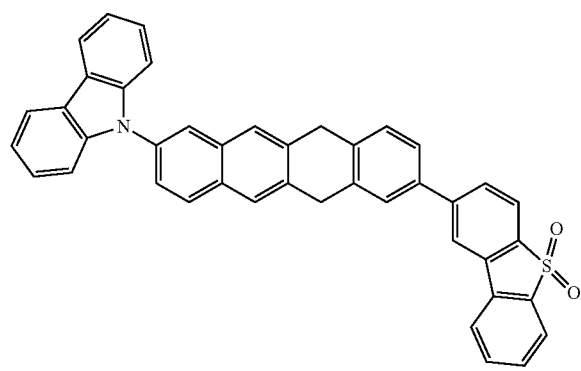
Compound 22
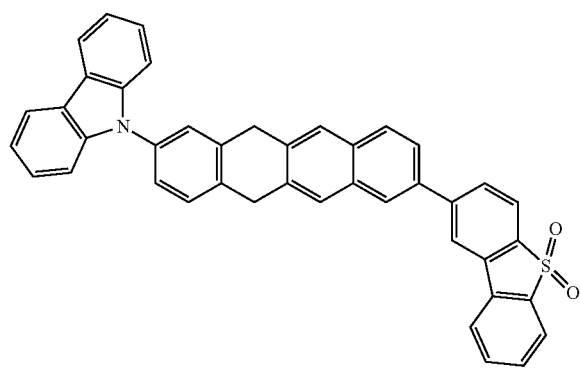
Compound 23
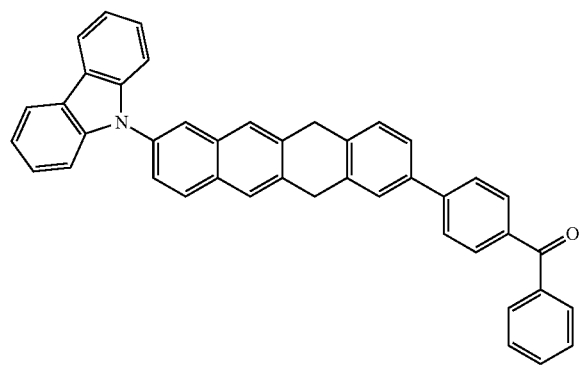
Compound 24
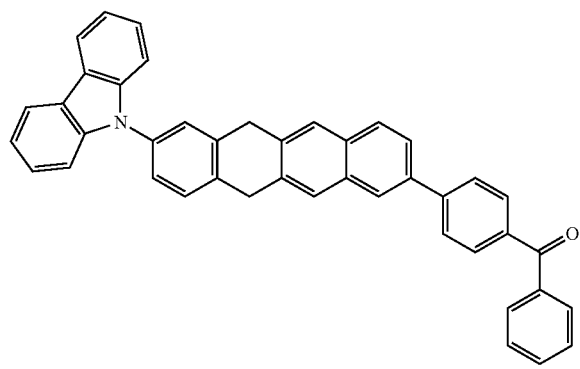

-continued
Compound 25
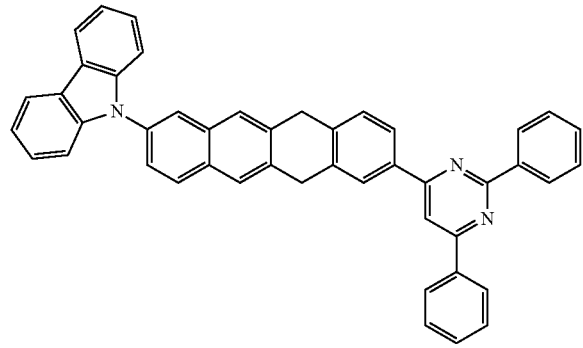
Compound 26
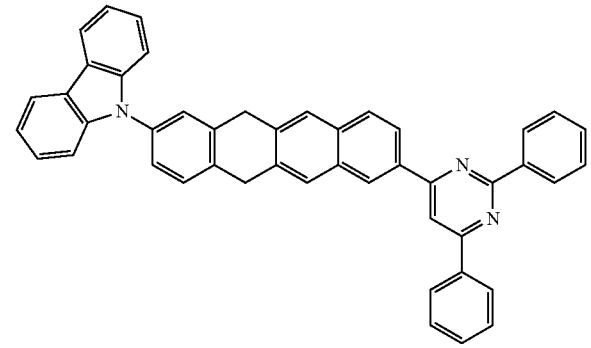
Compound 27
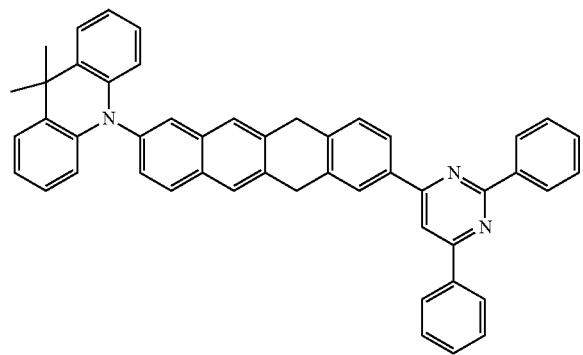
Compound 28
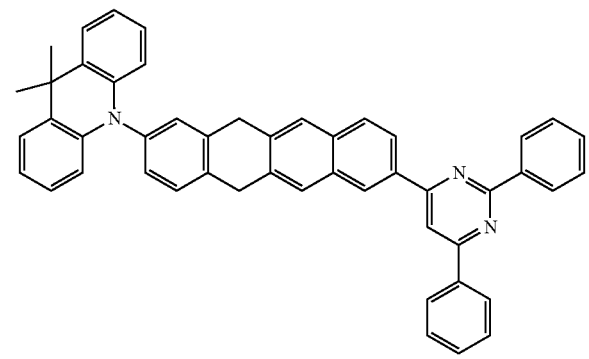
Compound 29
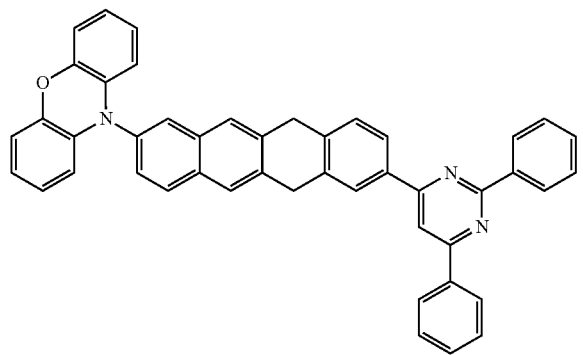
Compound 30
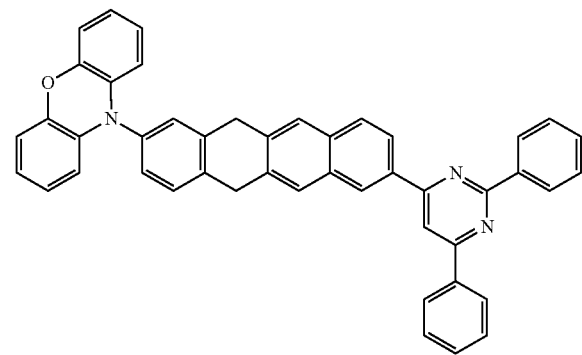
Compound 31
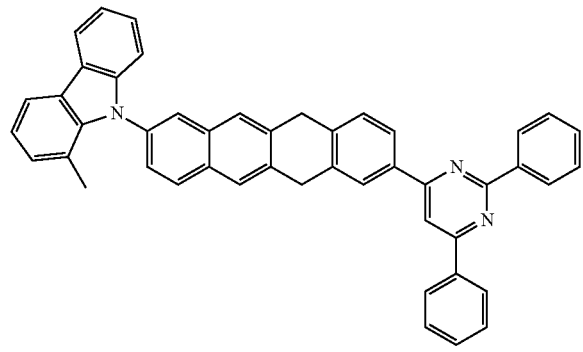
Compound 32
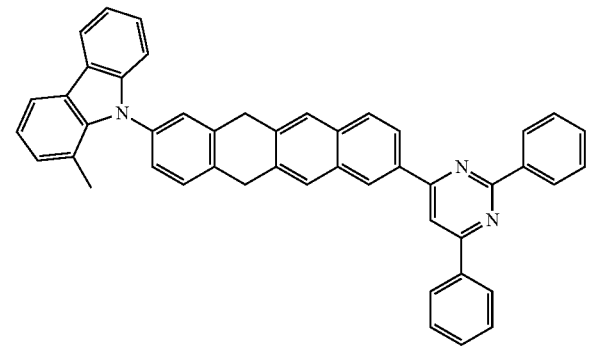

Compound 33
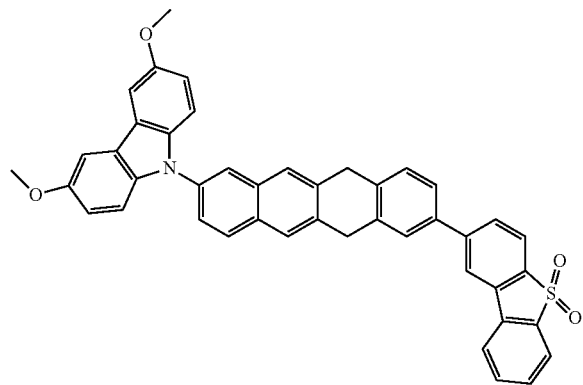
Compound 34
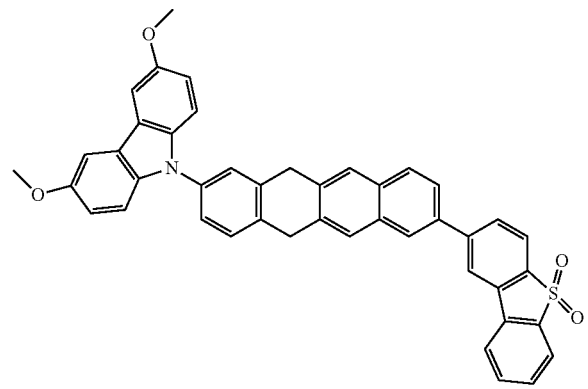
Compound 35
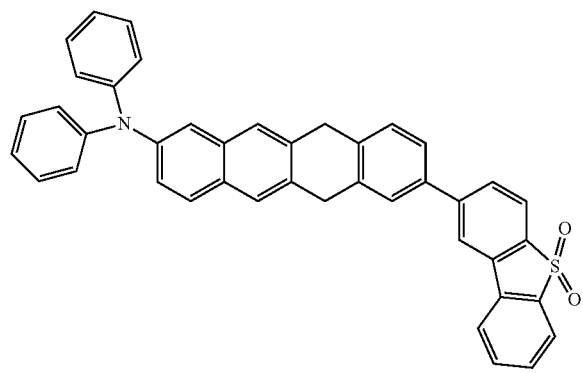
Compound 36
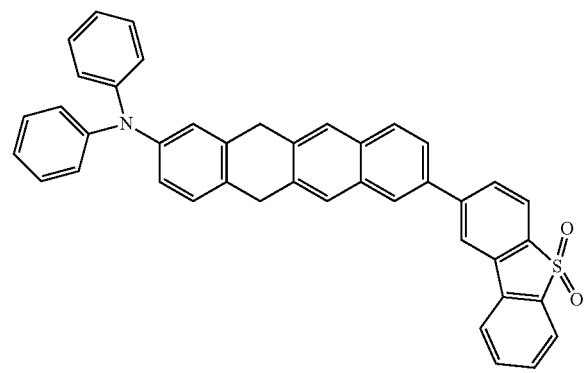
Compound 37
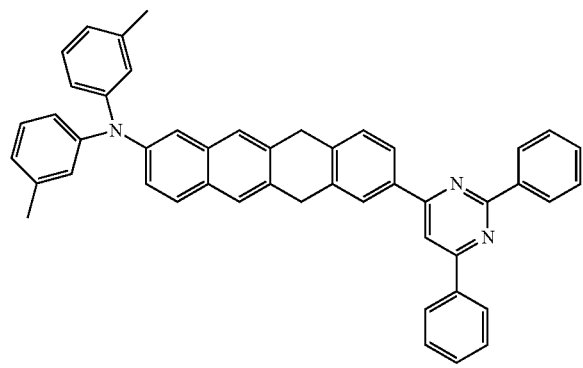
Compound 38
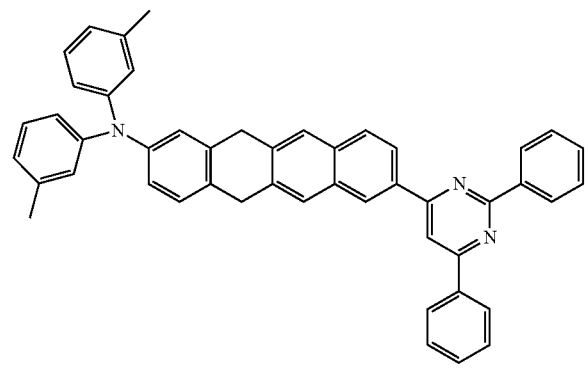

Compound 39
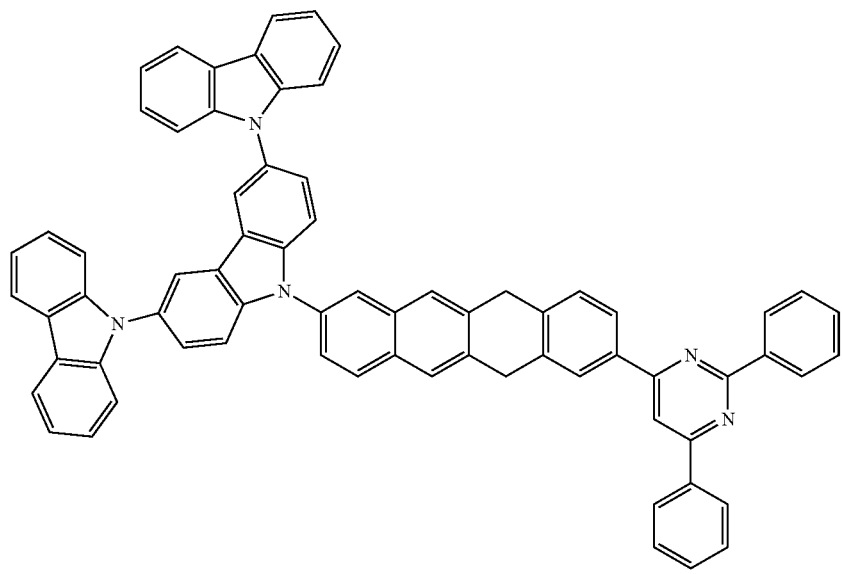
Compound 40
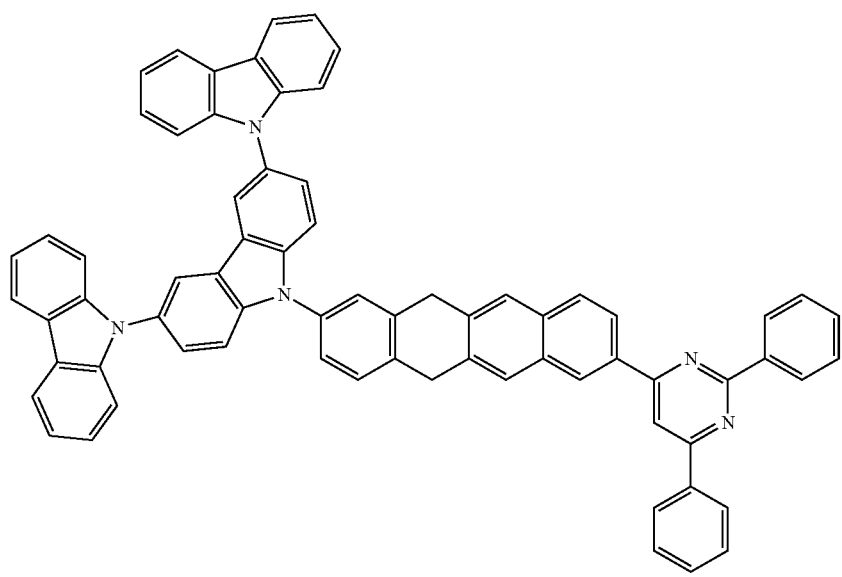
Compound 41
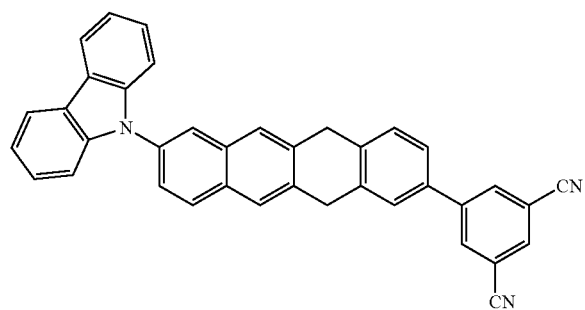
Compound 42
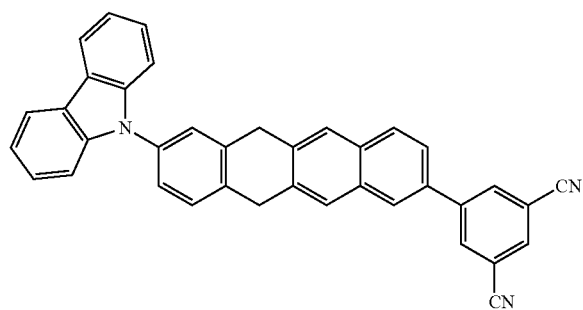

-continued
Compound 43
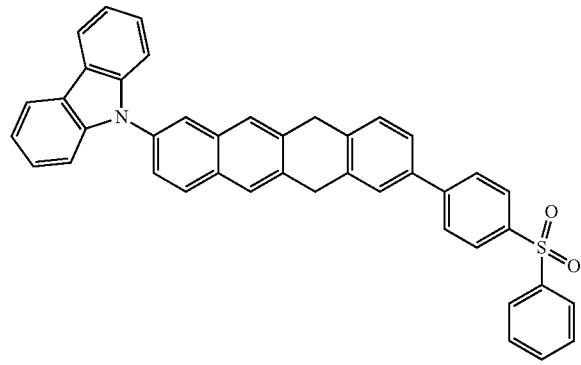
Compound 44
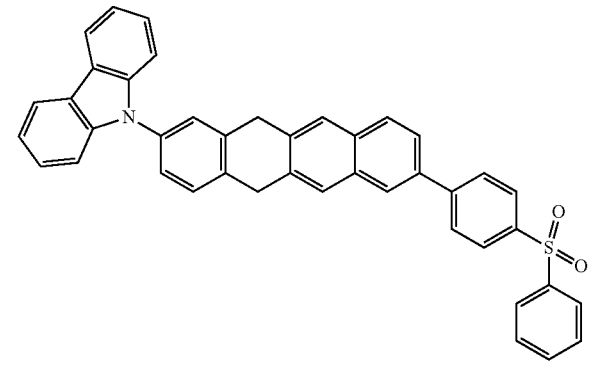
Compound 45
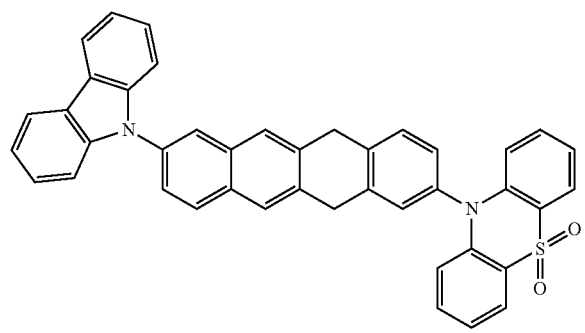
Compound 46
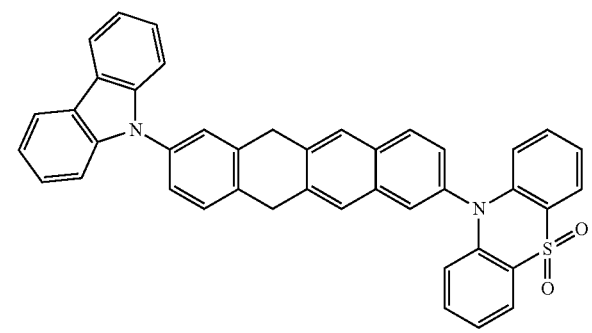
Compound 47
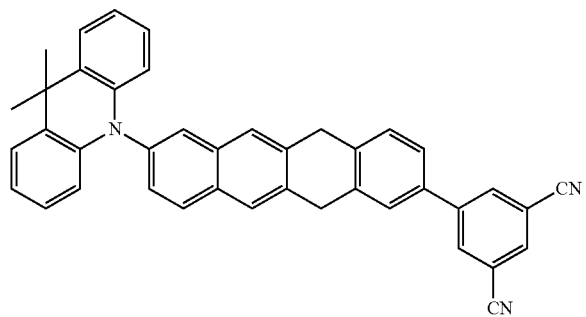
Compound 48
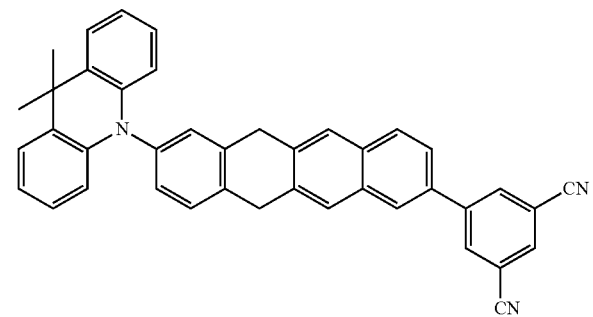
Compound 49
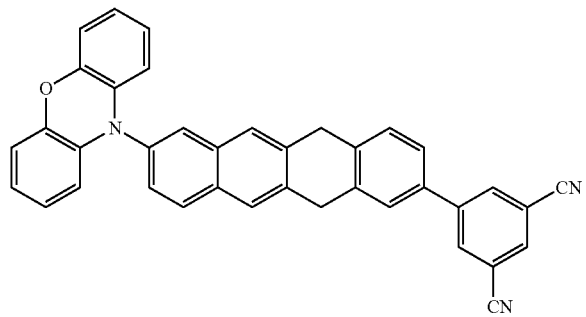
Compound 50
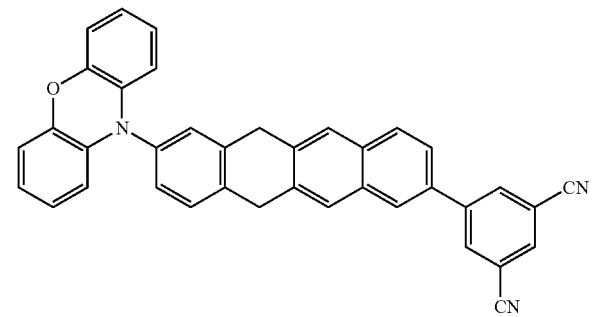

Compound 51
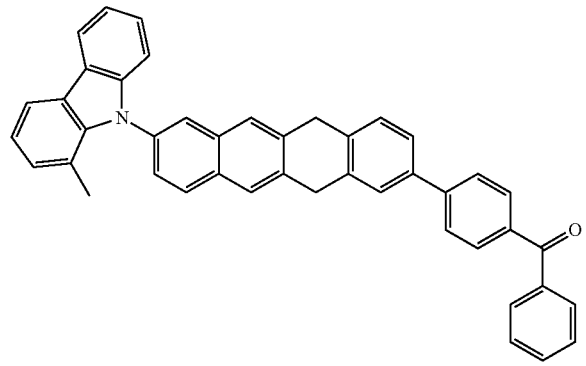
Compound 52
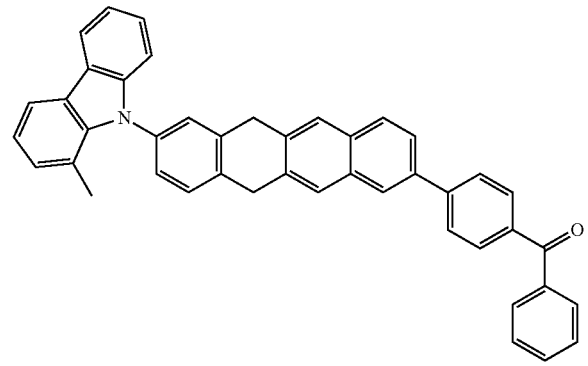
Compound 53
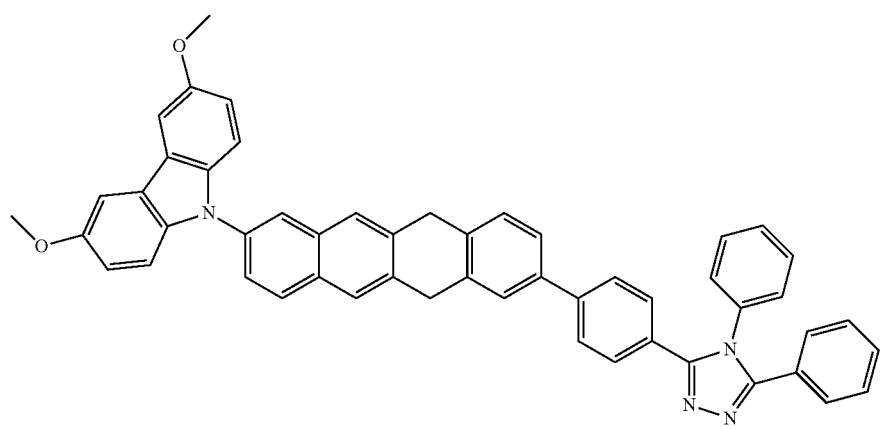
Compound 54
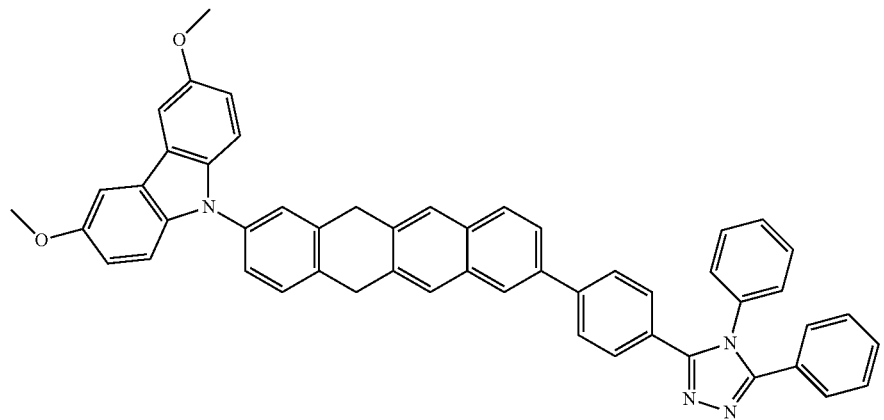
Compound 55
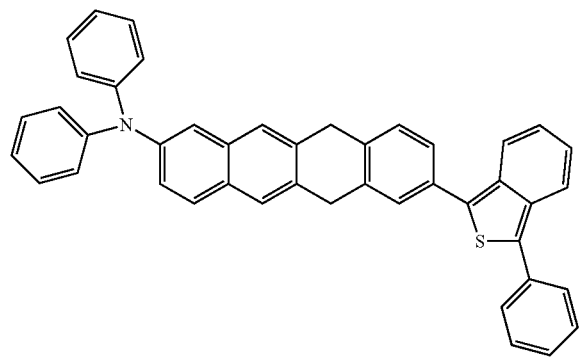
Compound 56
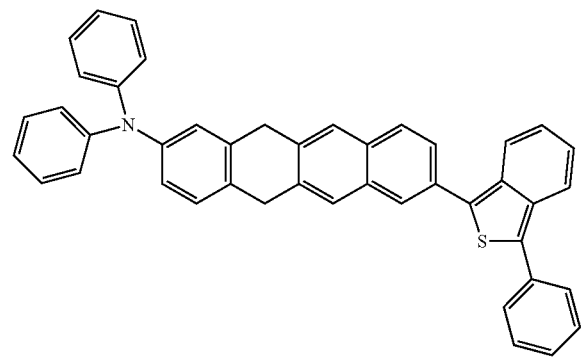

-continued
Compound 57
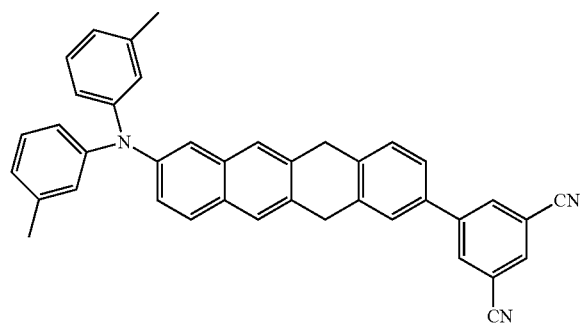
Compound 58
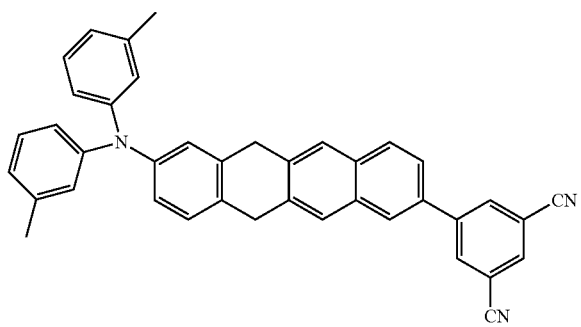
Compound 59
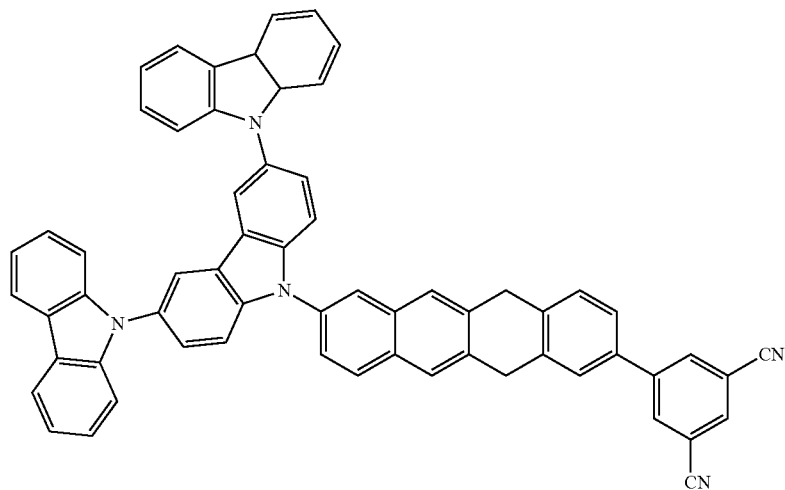
Compound 60
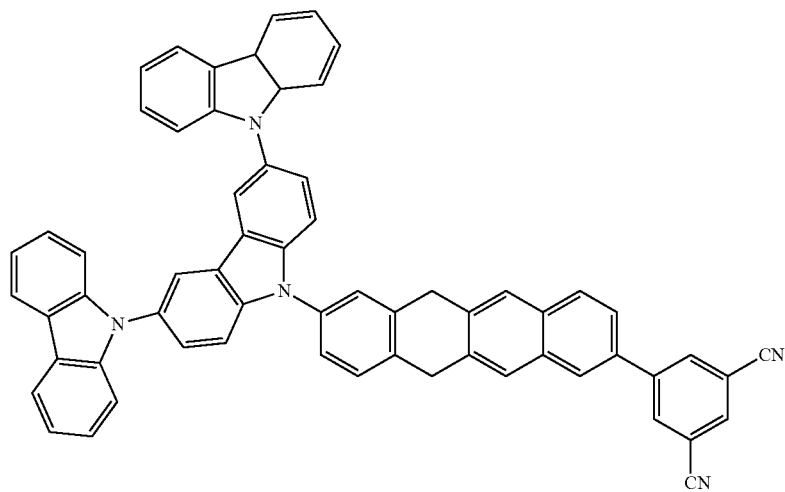

-continued
Compound 61
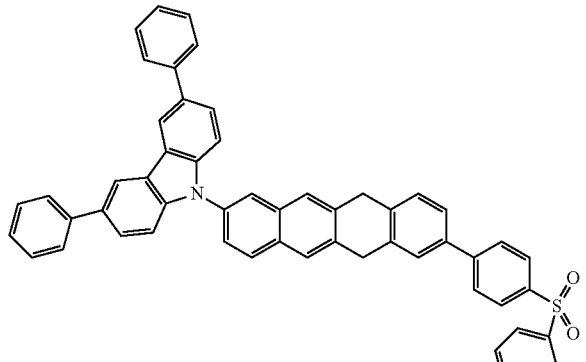
Compound 62
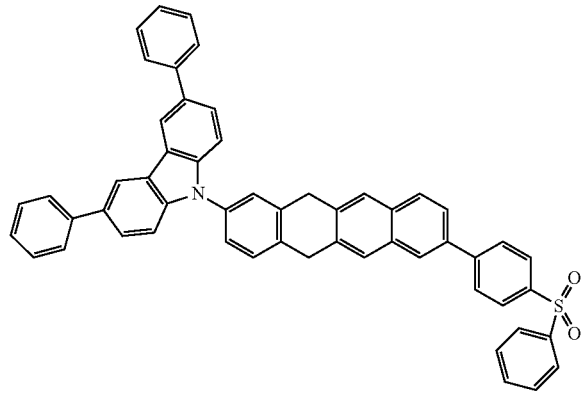
Compound 63
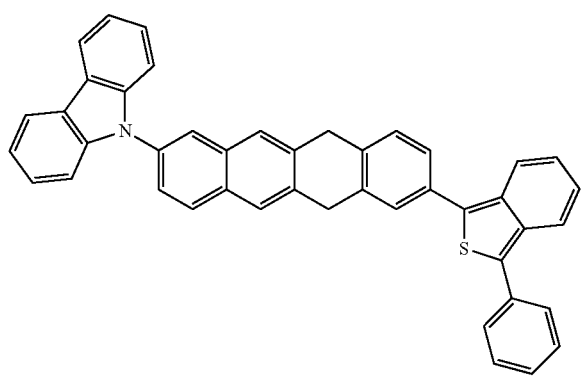
Compound 64
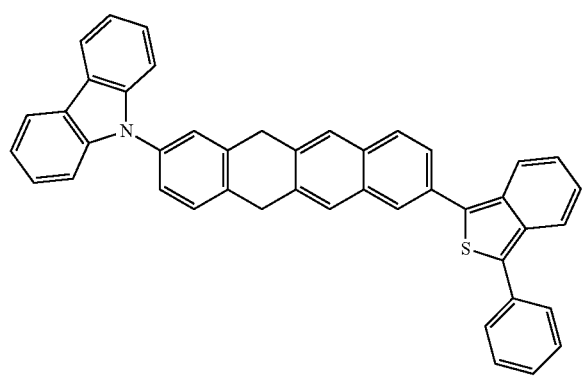
Compound 65
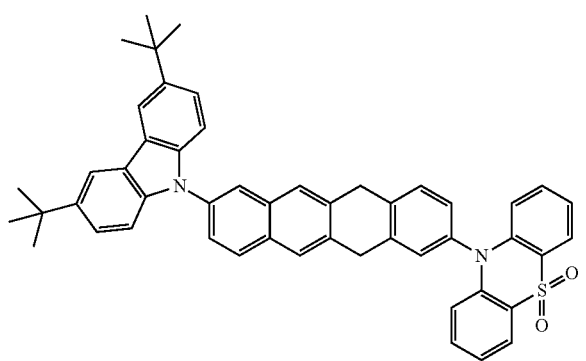
Compound 66
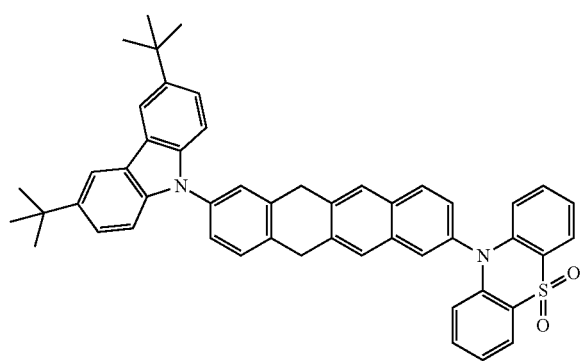
Compound 67
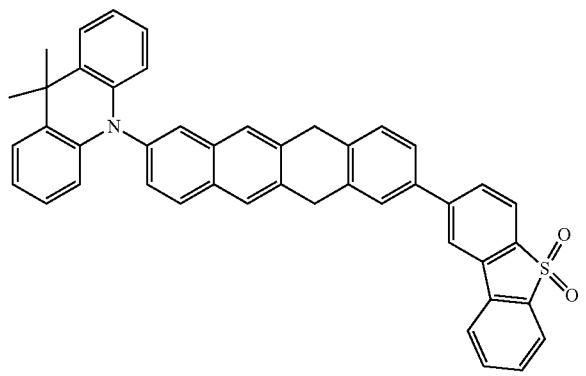
Compound 68
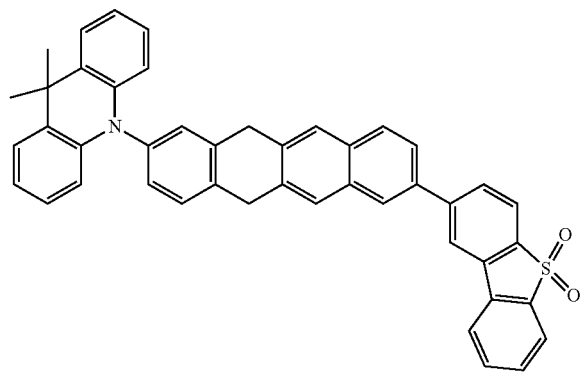

-continued
Compound 69
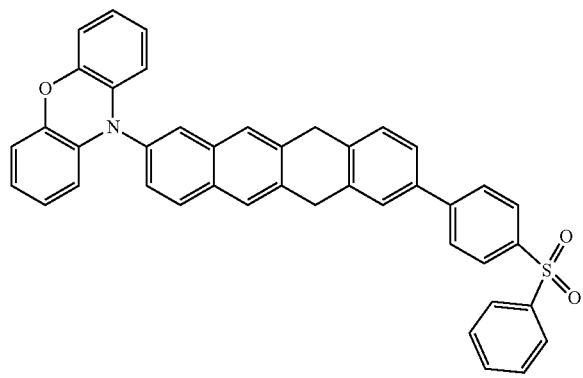
Compound 70
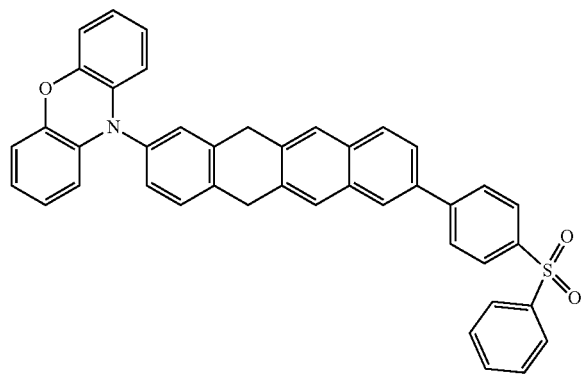
Compound 71
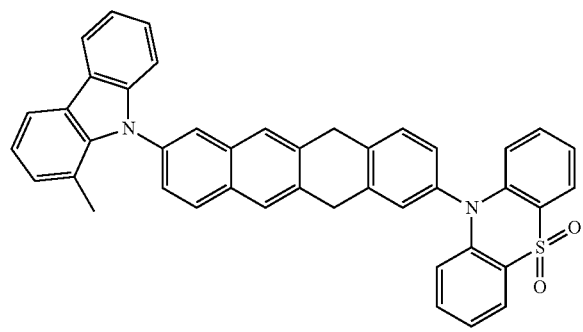
Compound 72
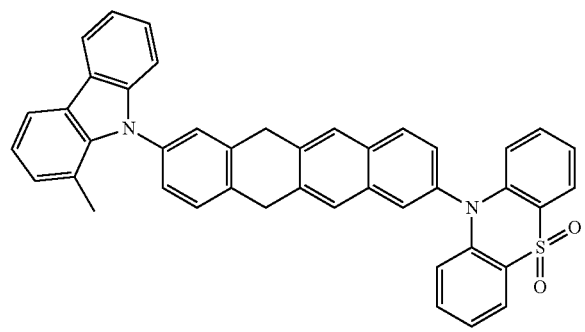
Compound 73
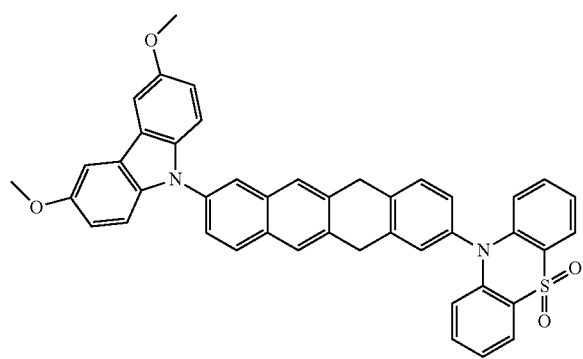
Compound 74
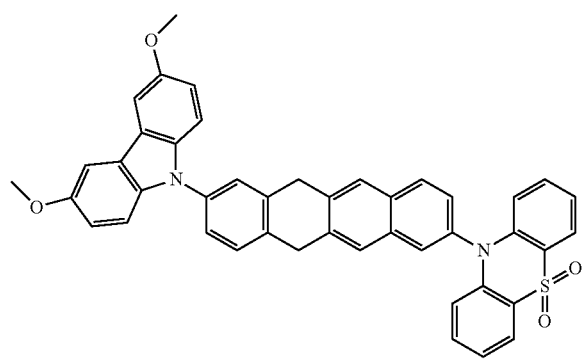
Compound 75
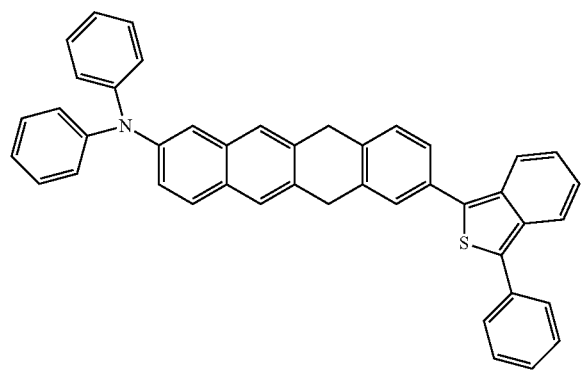
Compound 76
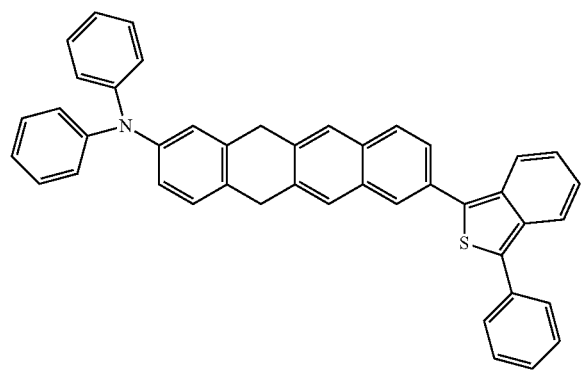

-continued
Compound 77
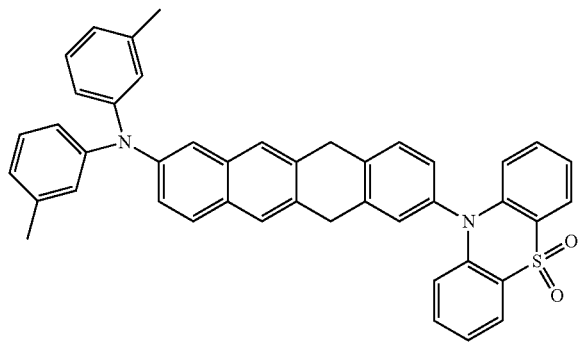
Compound 78
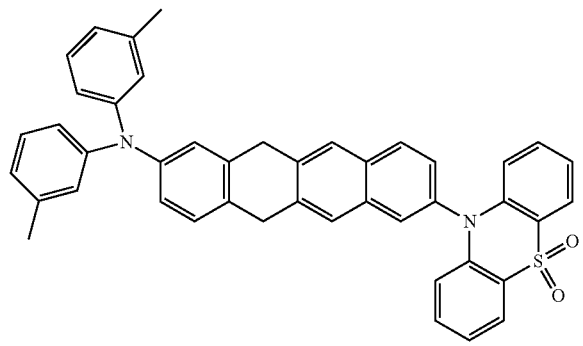
Compound 79
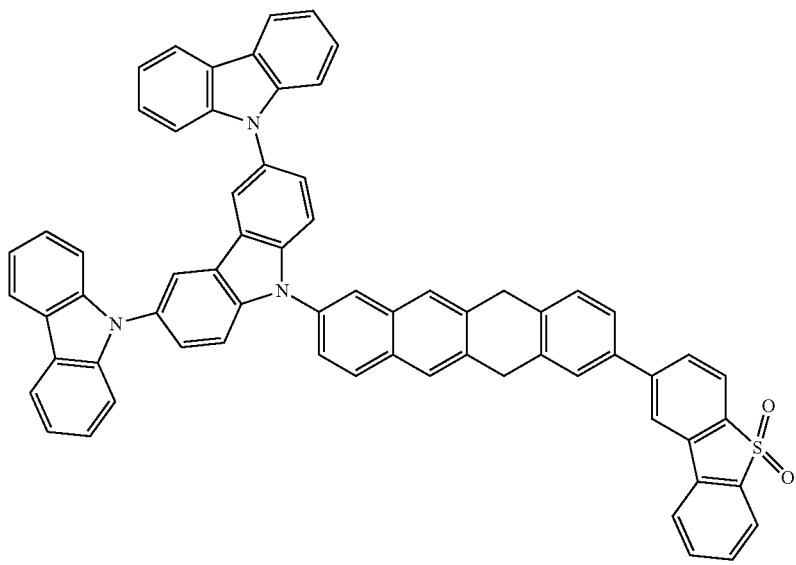
Compound 80
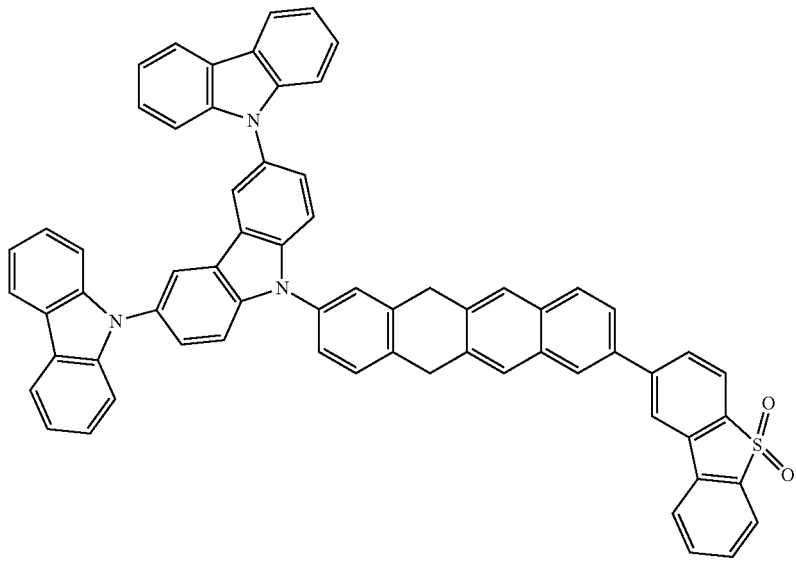

-continued
Compound 81
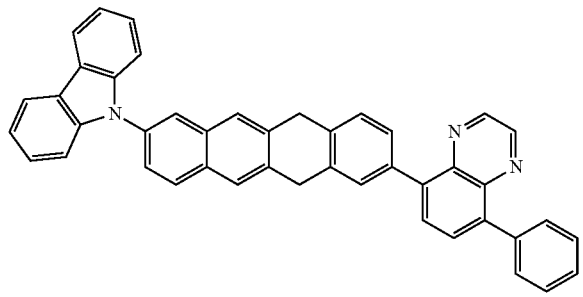
Compound 82
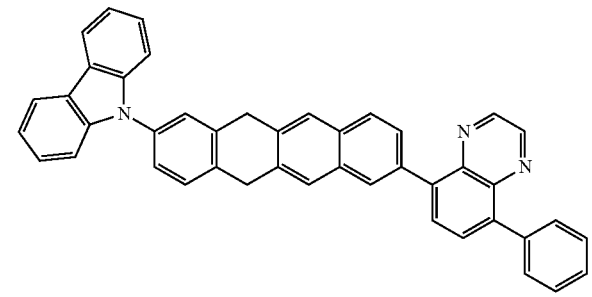
Compound 83
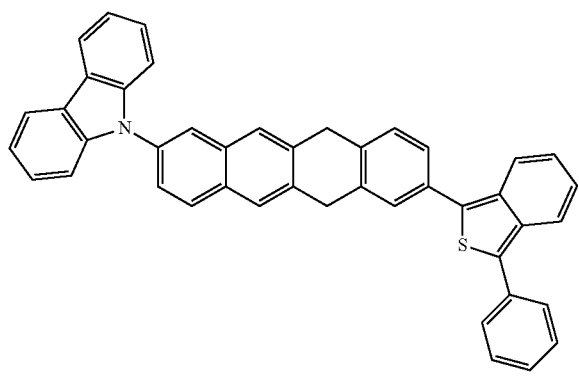
Compound 84
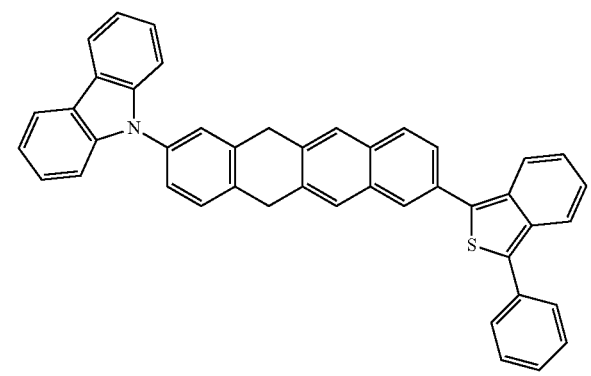
Compound 85
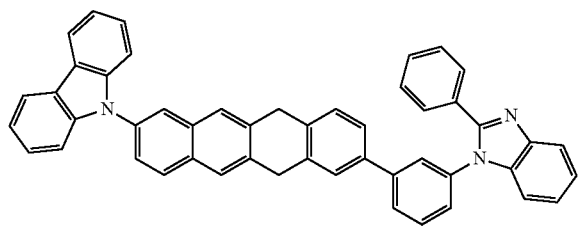
Compound 86
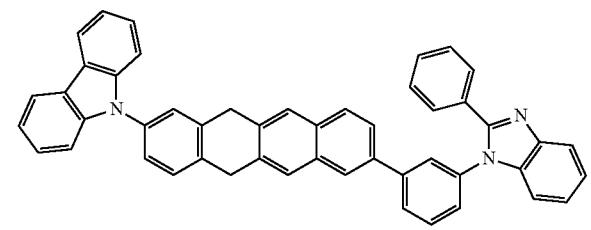
Compound 87
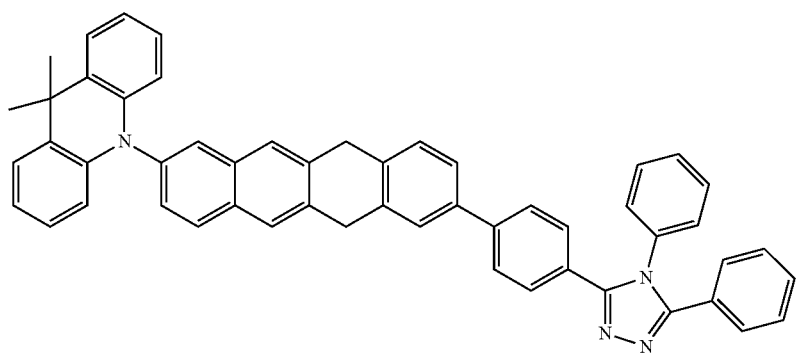

Compound 88
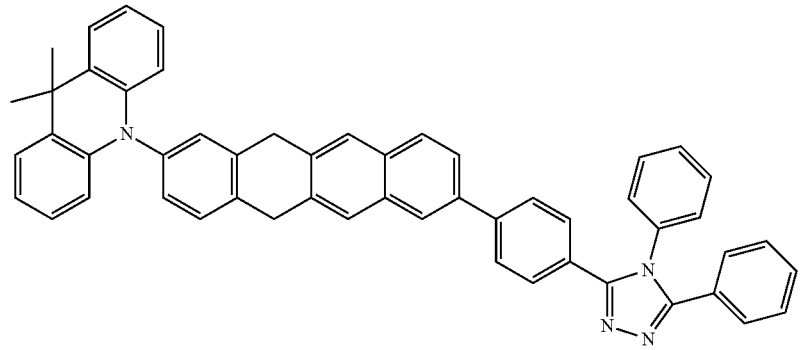
Compound 89
Compound 90
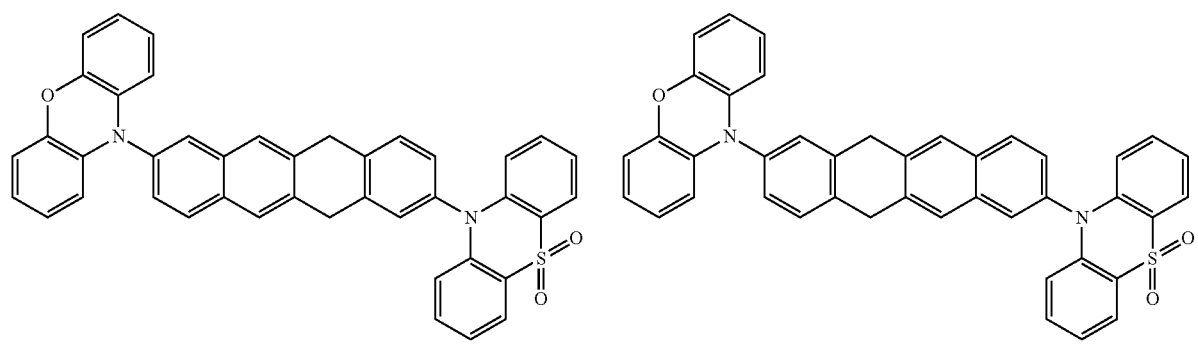
Compound 91
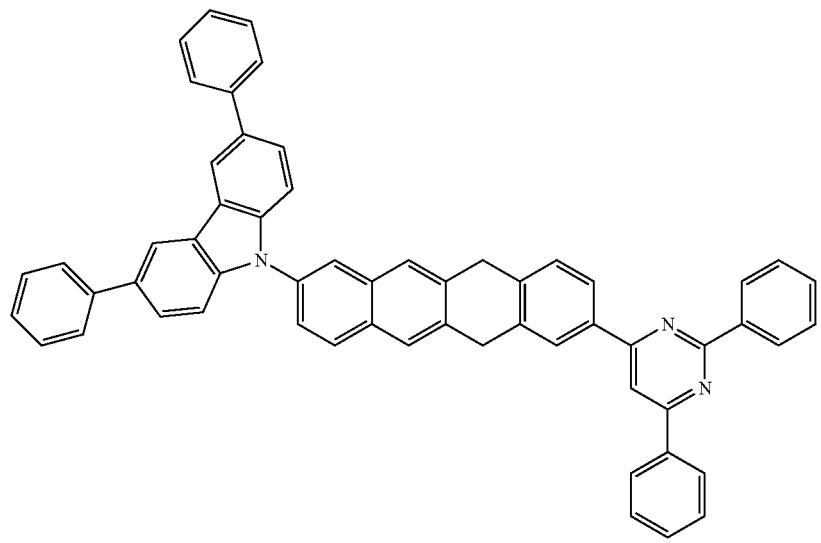

Compound 92
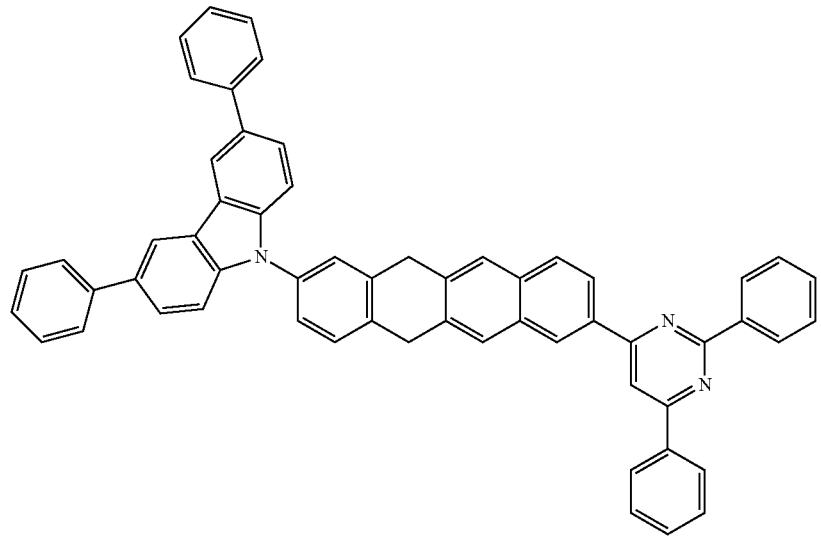
Compound 93
Compound 94
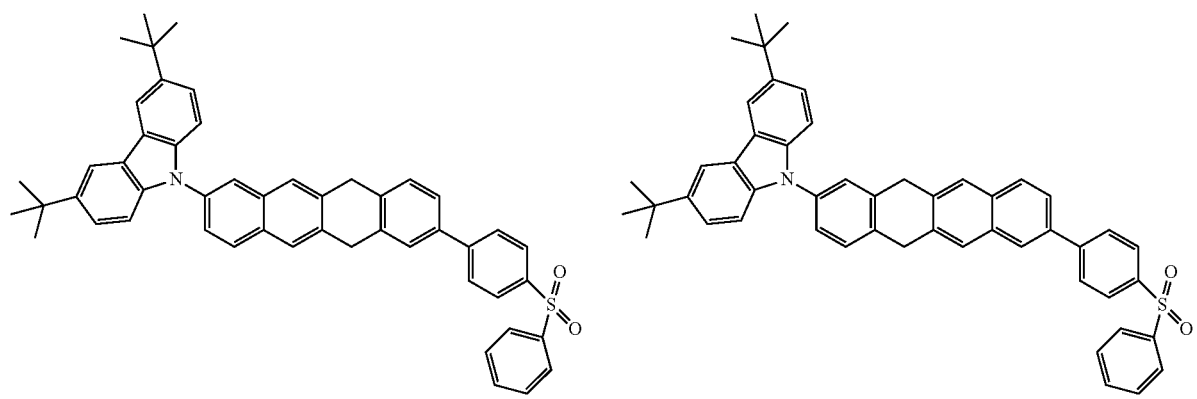
Compound 95
Compound 96
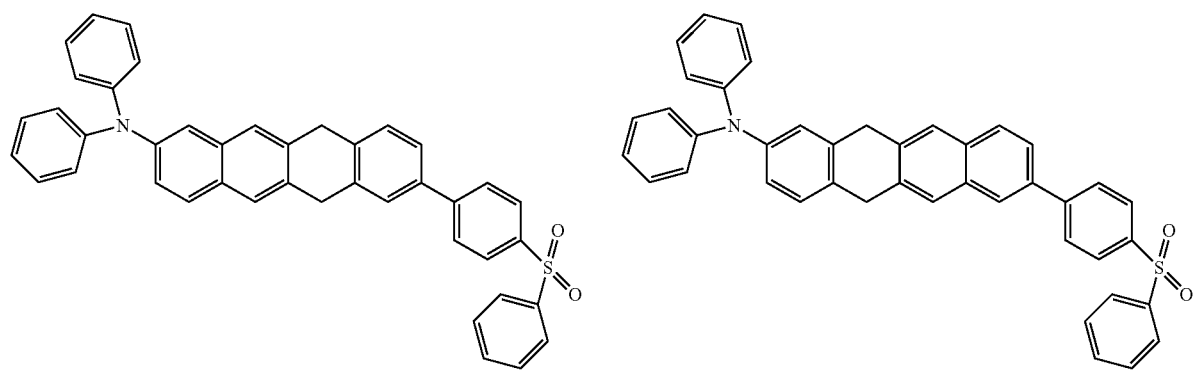

Compound 97
Compound 98
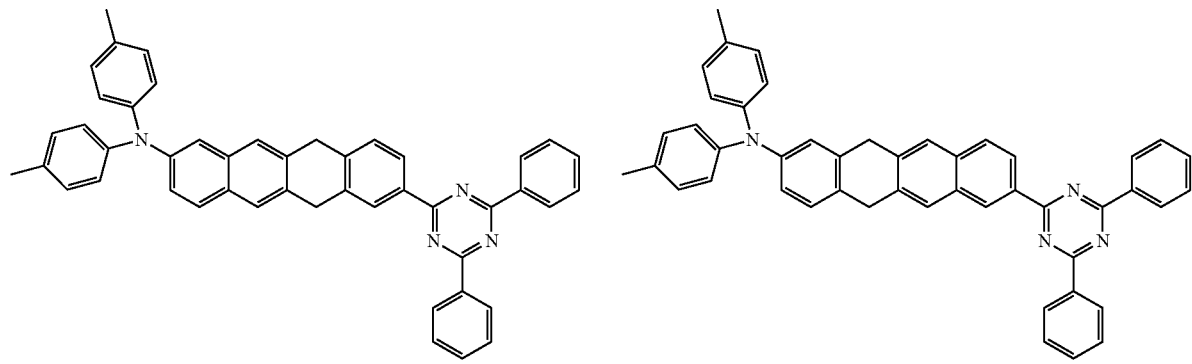
Compound 99
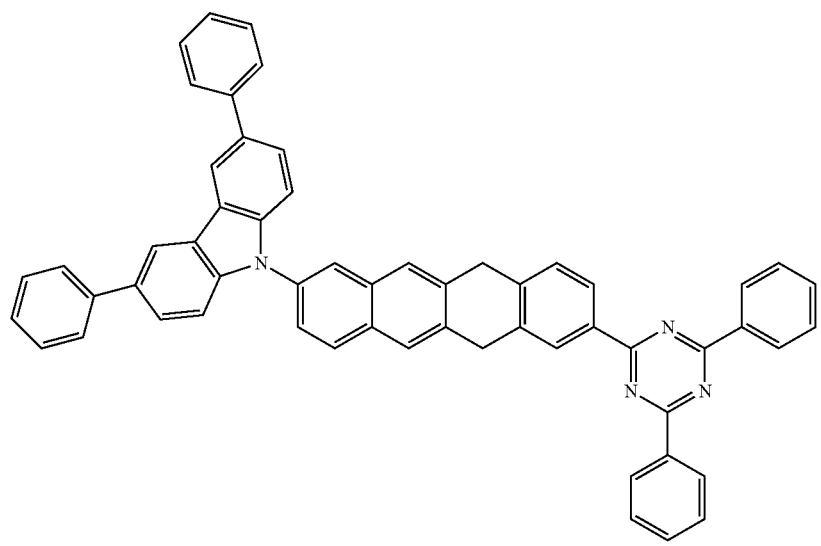
Compound 100
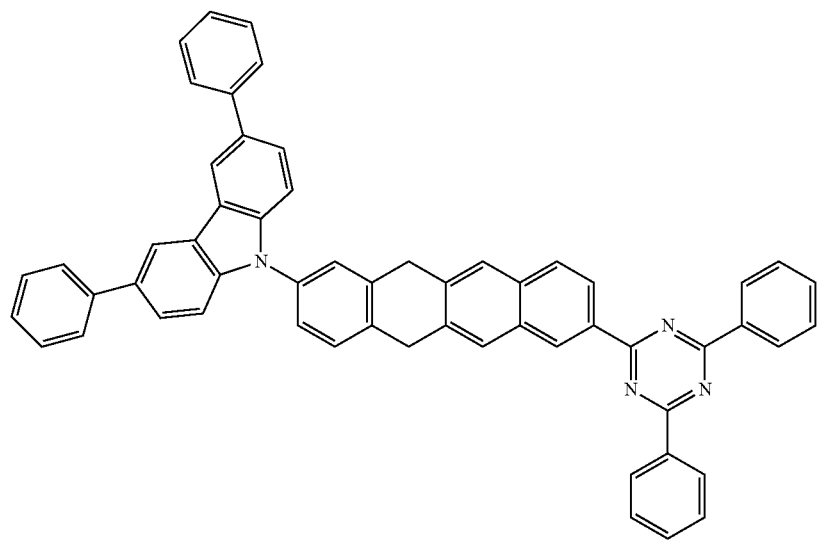

-continued
Compound 101
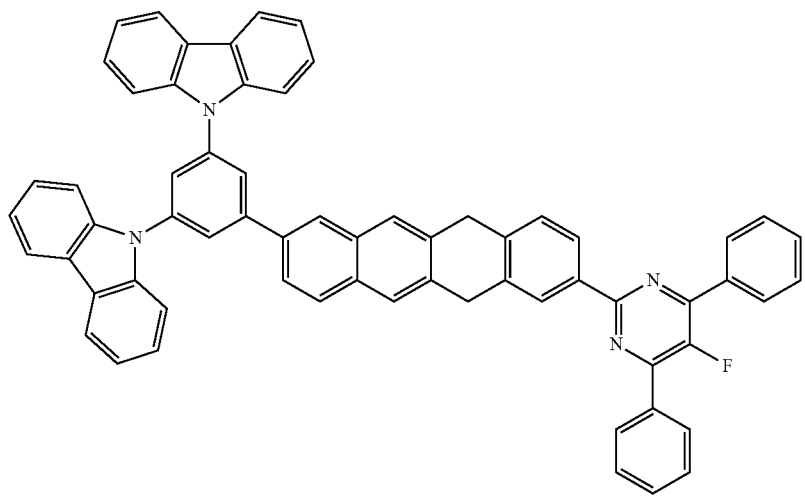
Compound 102
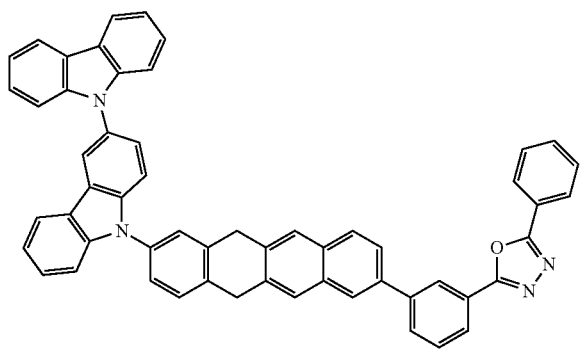
Compound 103
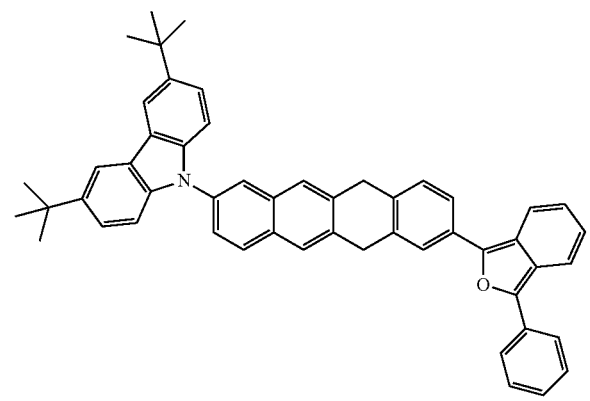
Compound 104
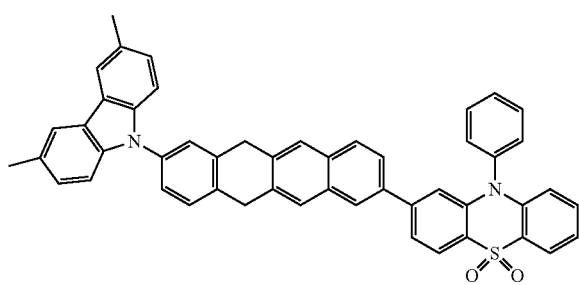
Compound 105
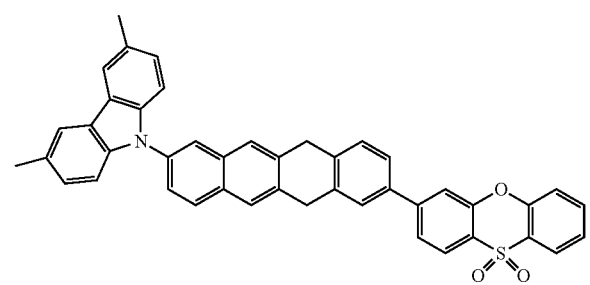
Compound 106
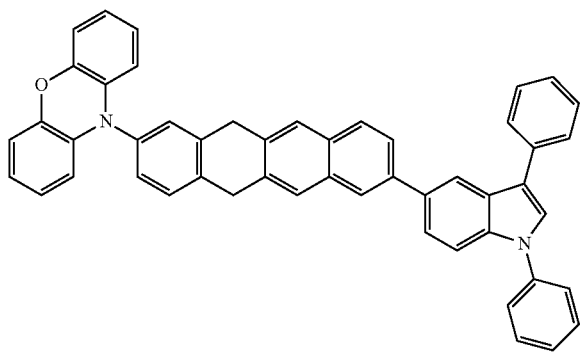

-continued
Compound 108
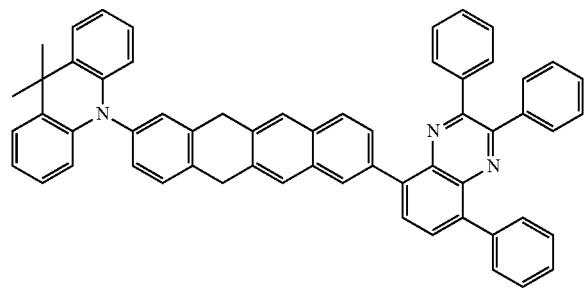
Compound 109
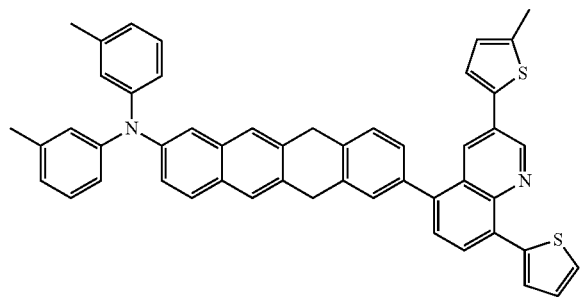
Compound 110
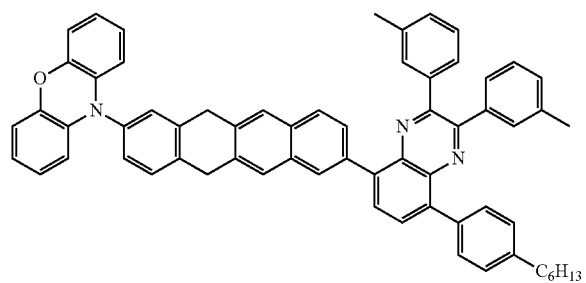
Compound 111
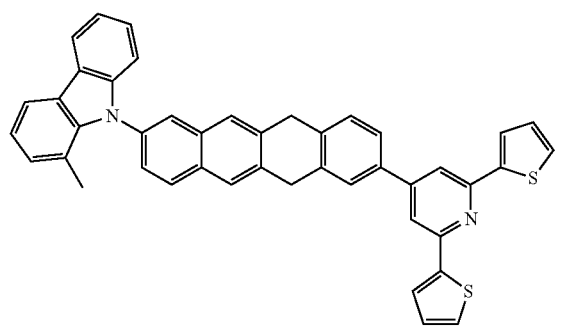
Compound 112
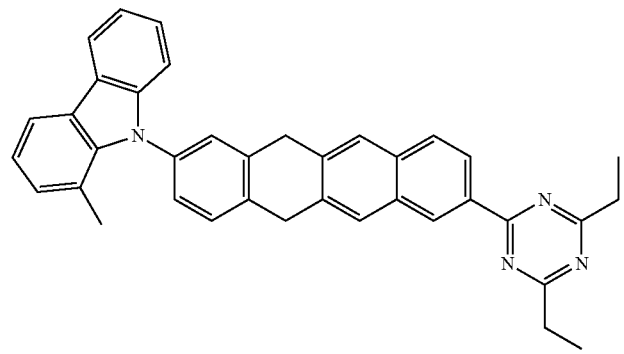
Compound 113
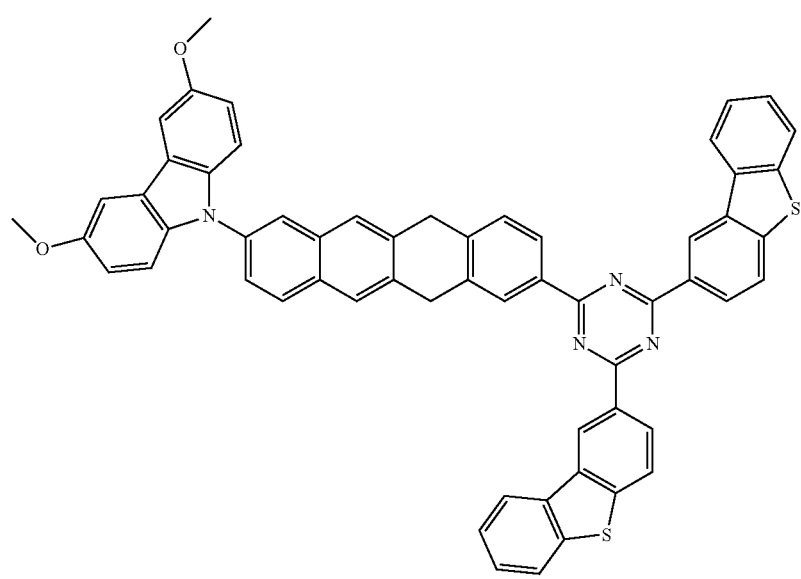

-continued
Compound 114
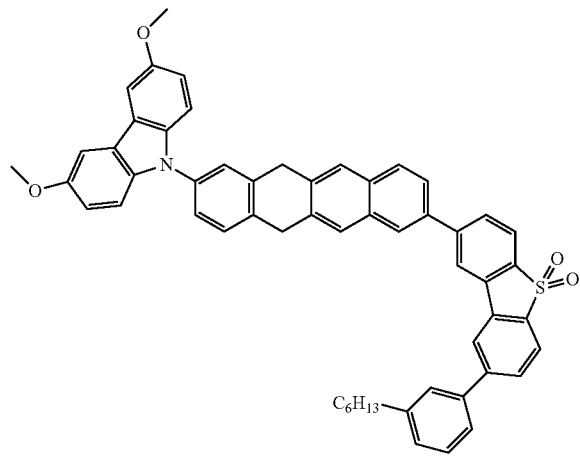
Compound 115
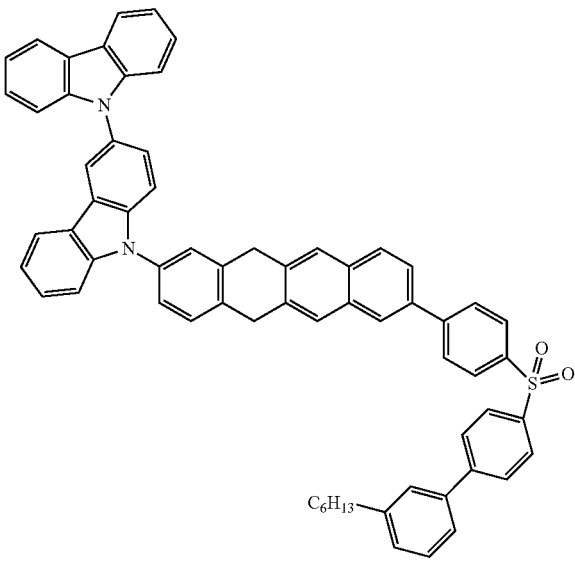
Compound 116
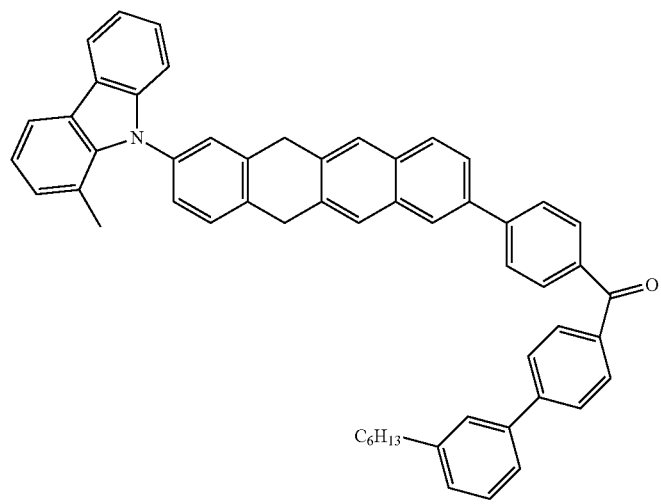
Compound 117
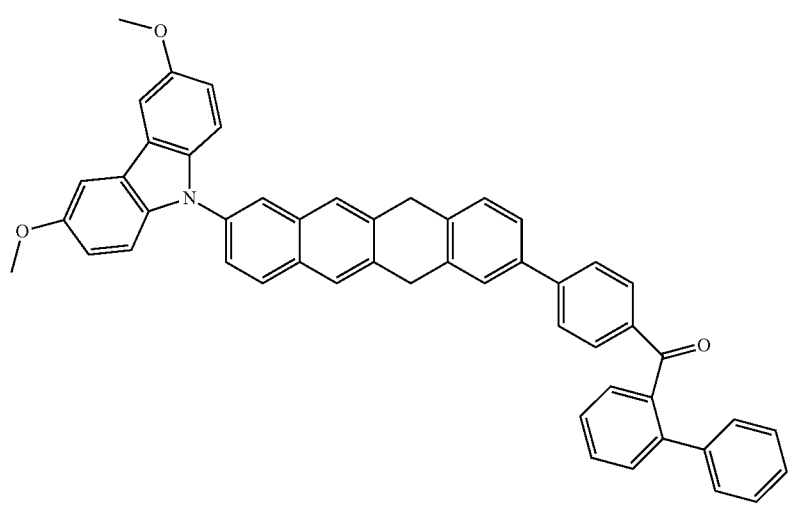

Compound 118
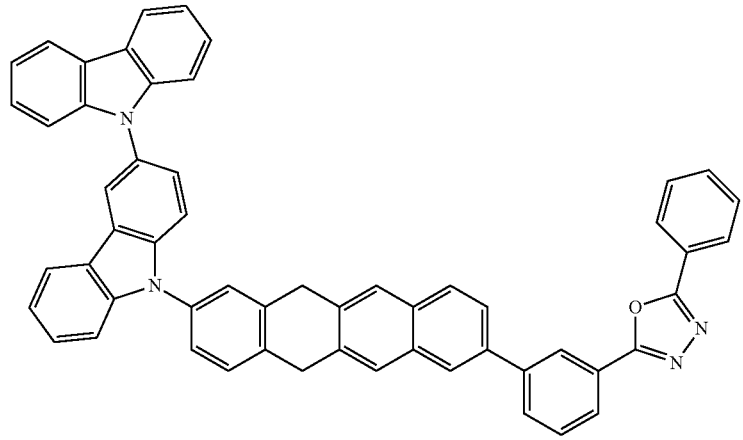
Compound 119
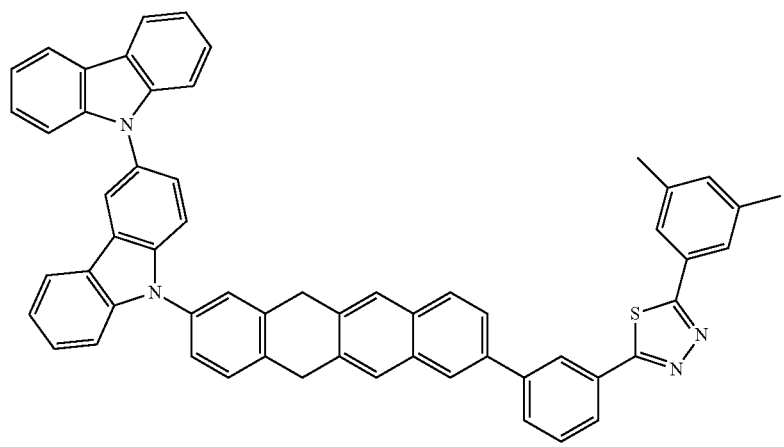
Compound 120
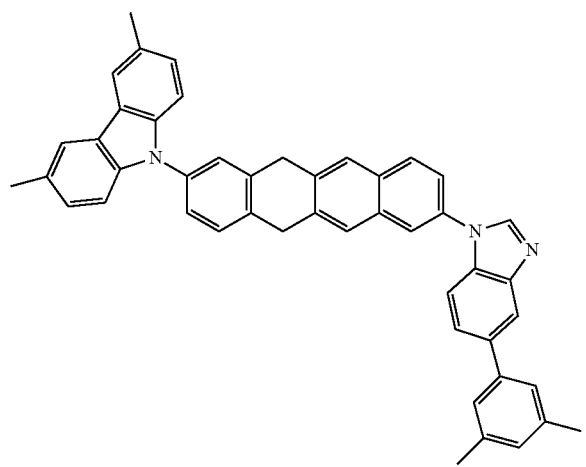
Compound 121
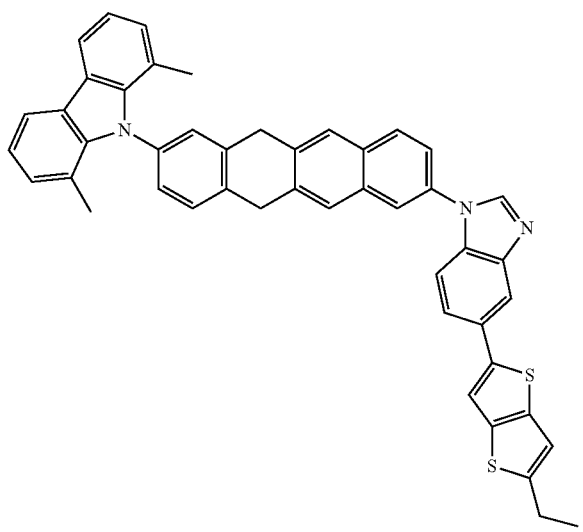

Compound 122
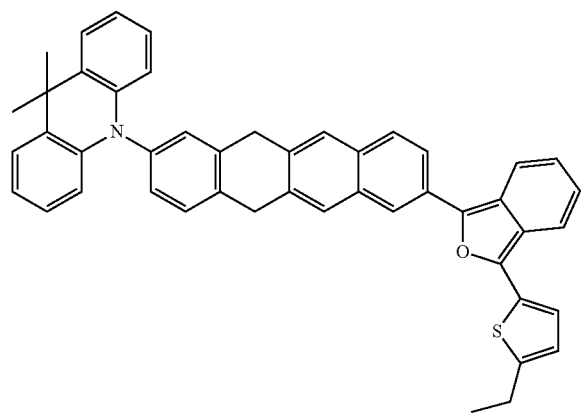
Compound 123
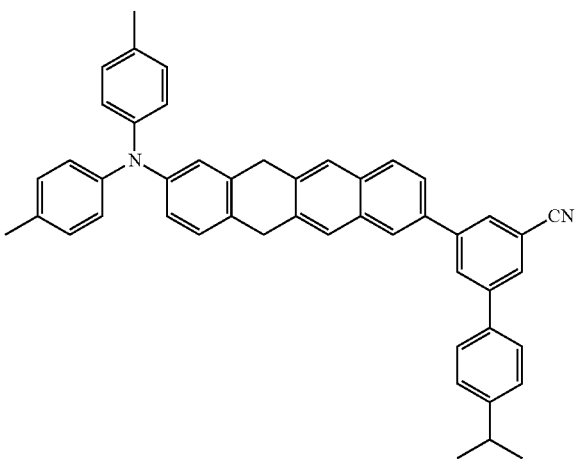
Compound 124
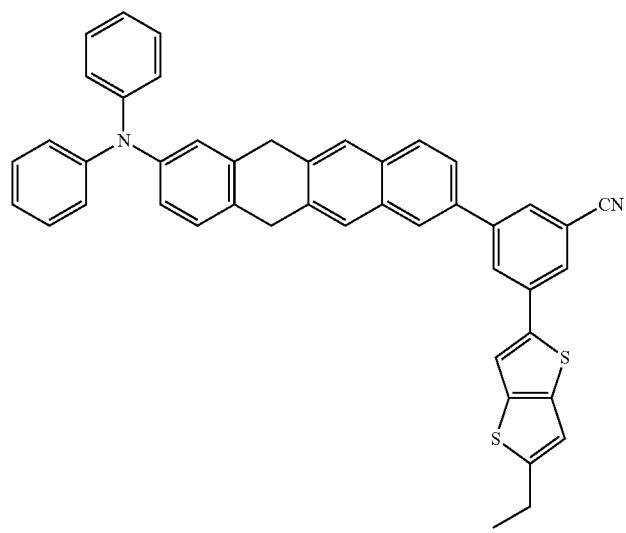
Compound 125
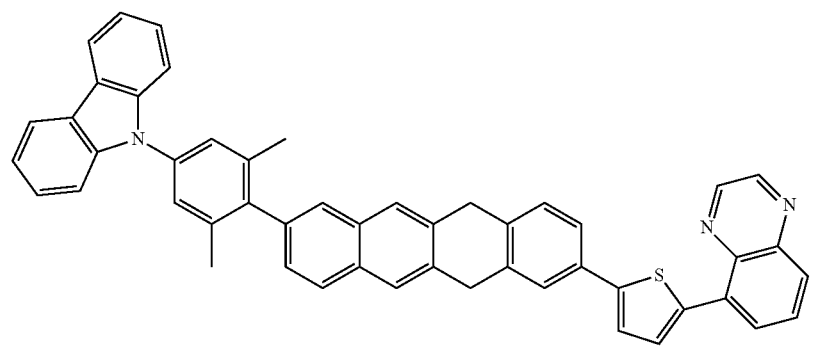

-continued
Compound 126
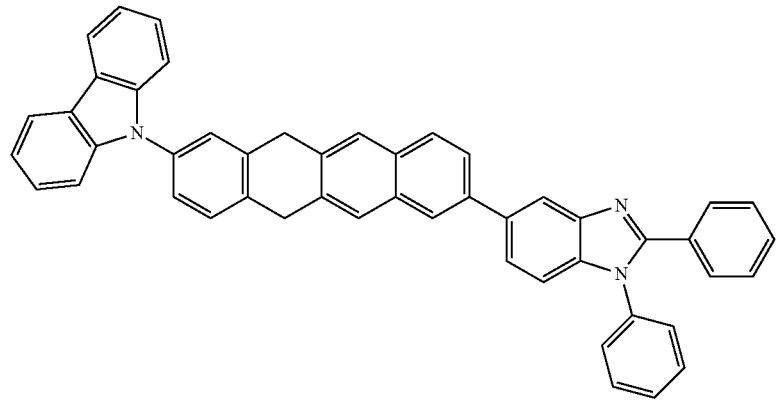
Compound 127
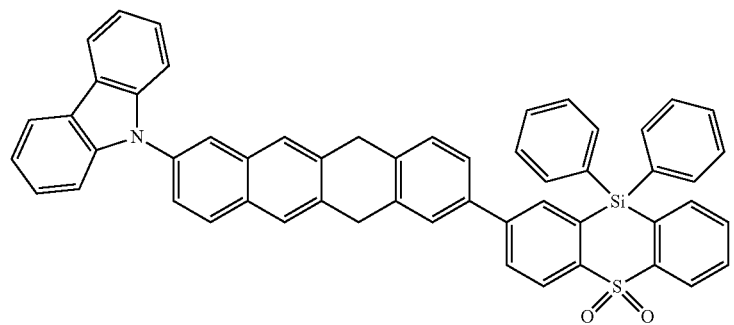
Compound 128
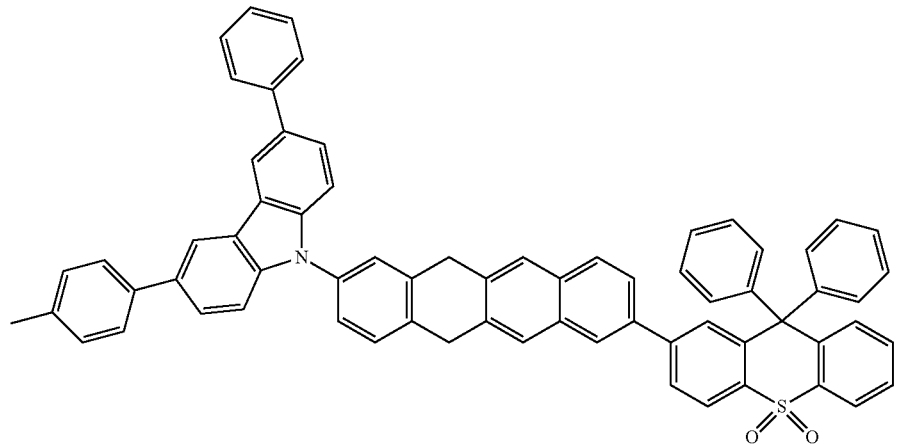
Compound 129
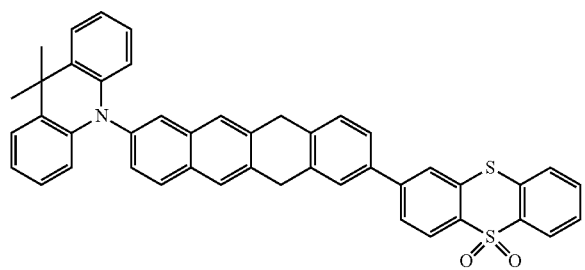
Compound 130
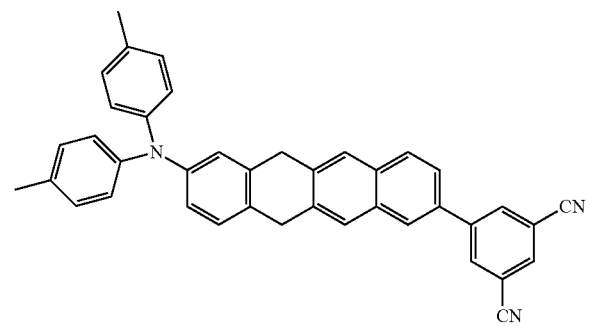

Compound 131
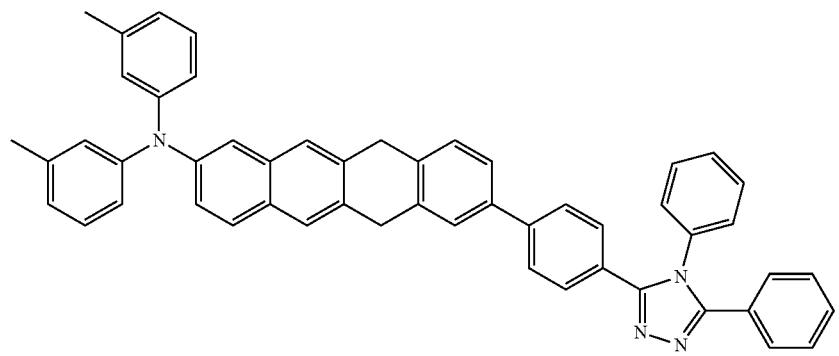
Compound 132
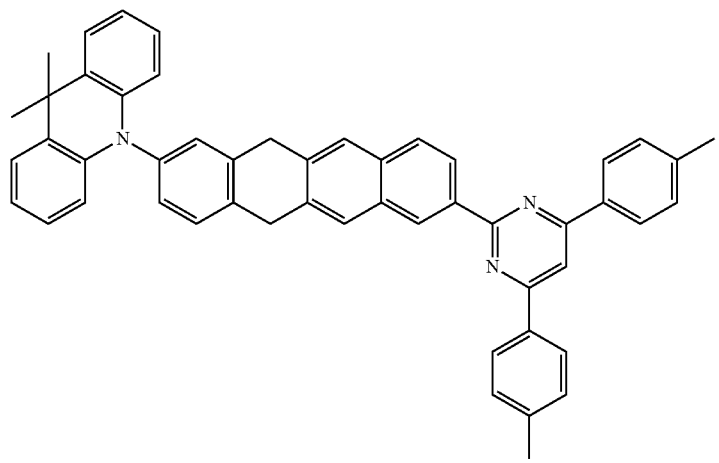
Compound 133
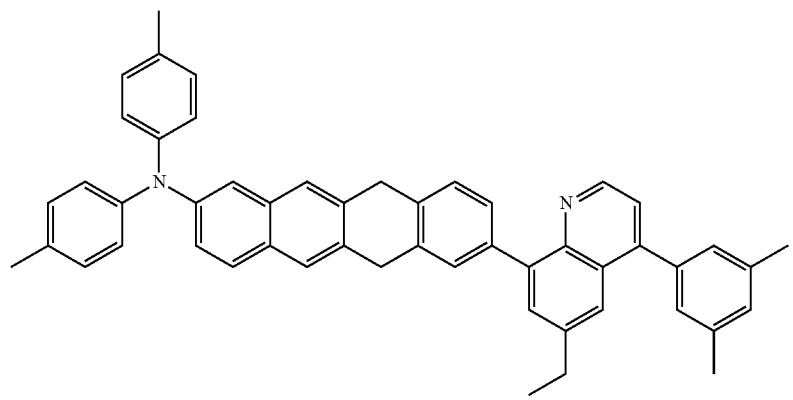
Compound 134
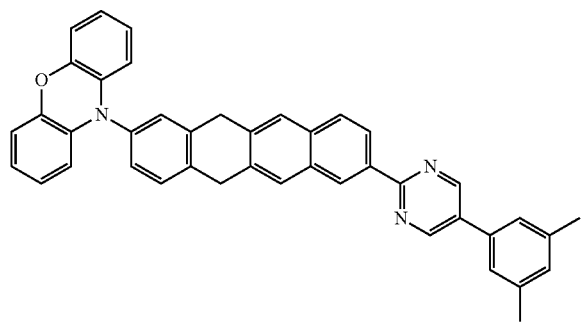
Compound 135
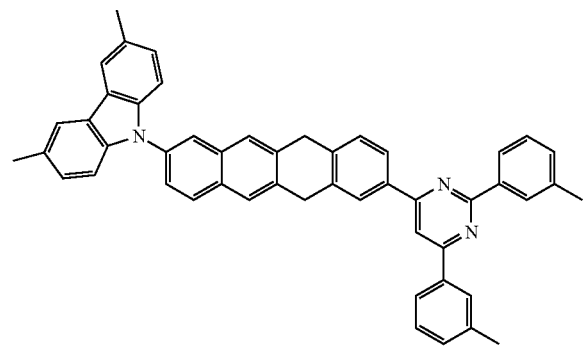

-continued
Compound 136
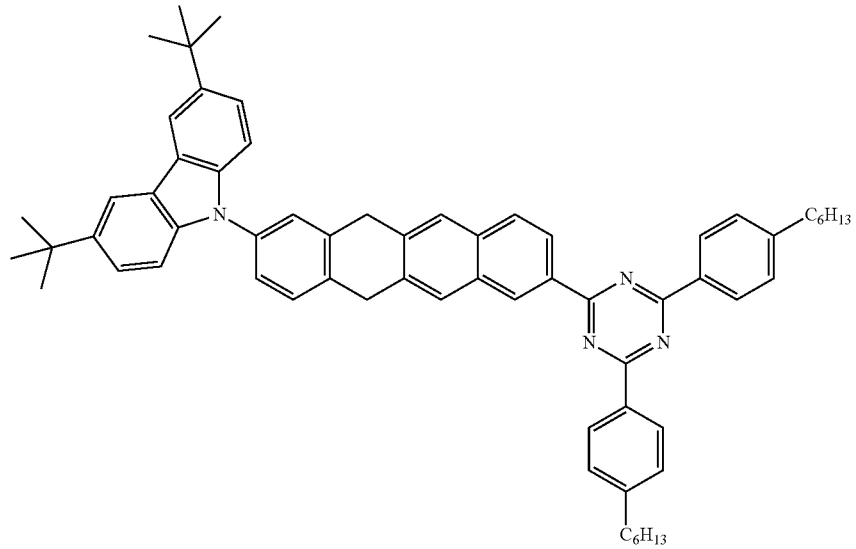
Compound 137
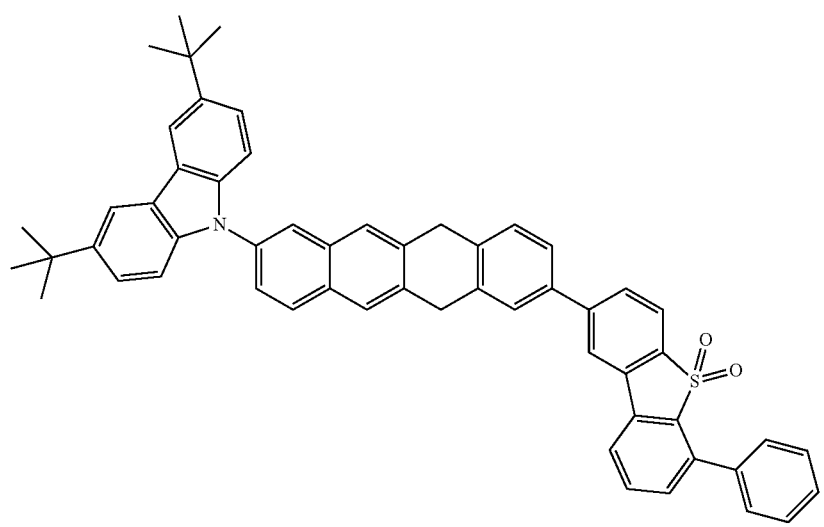
Compound 138
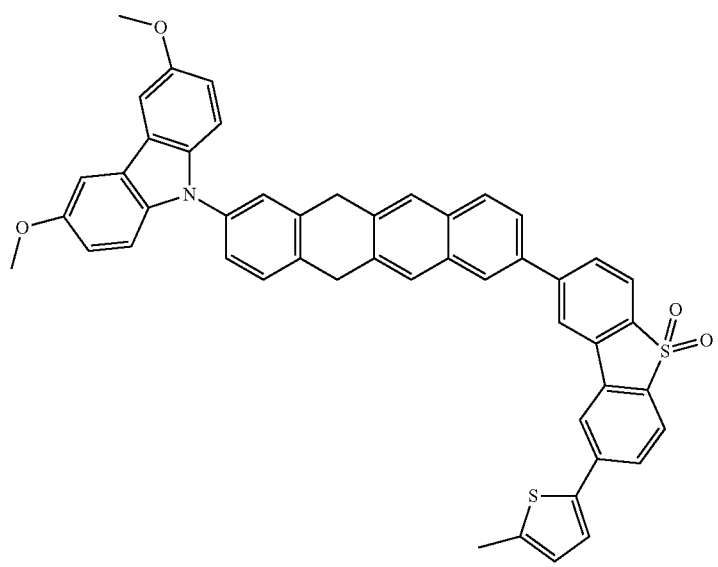

Compound 139
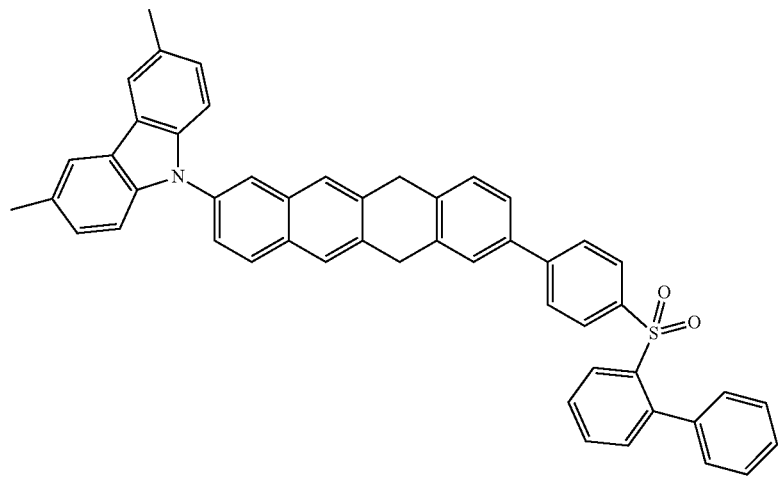
Compound 140
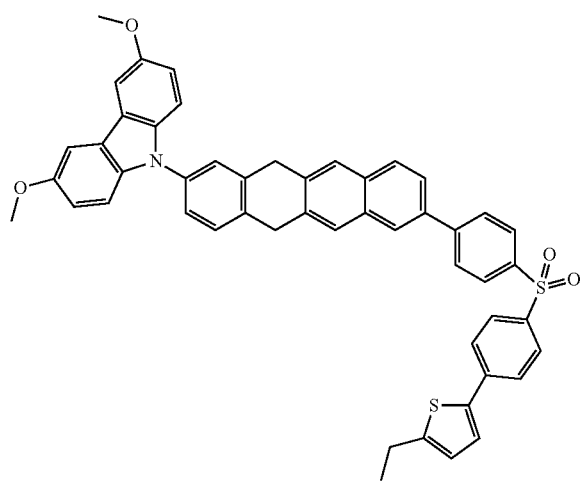
Compound 141
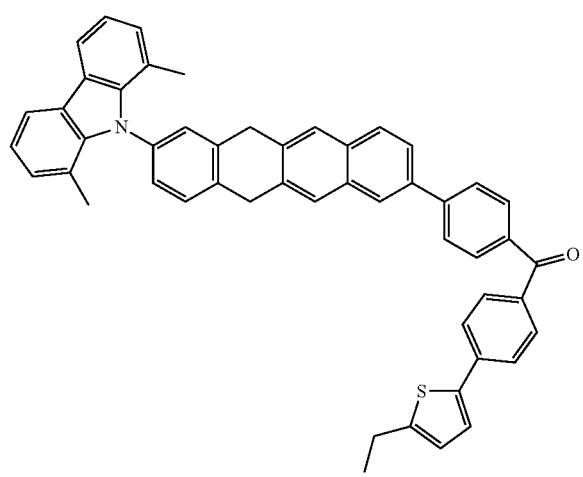
Compound 142
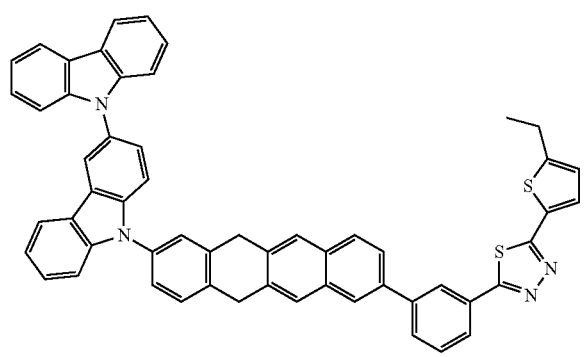
Compound 143
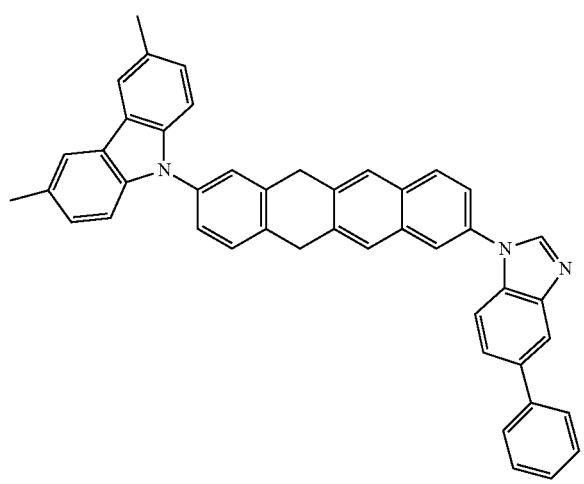

Compound 144

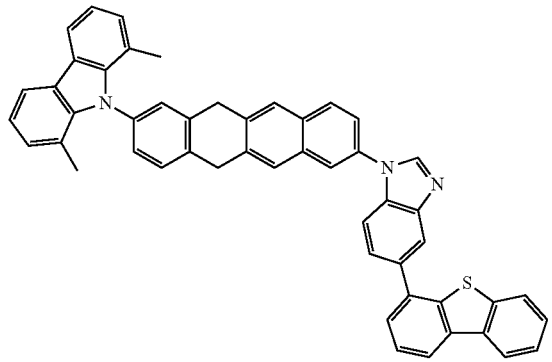

Compound 145

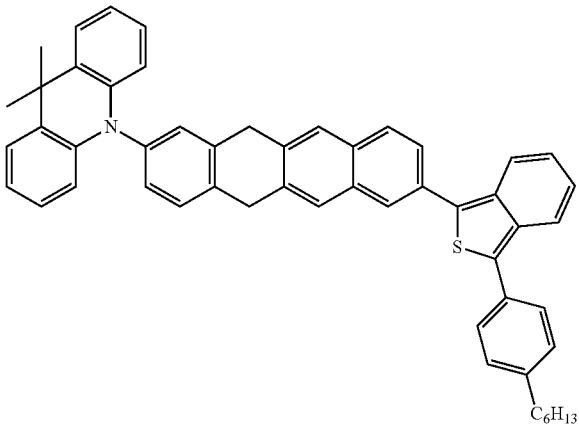

Compound 146

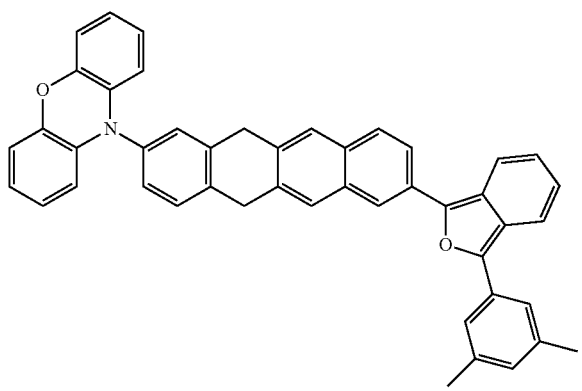

Compound 147

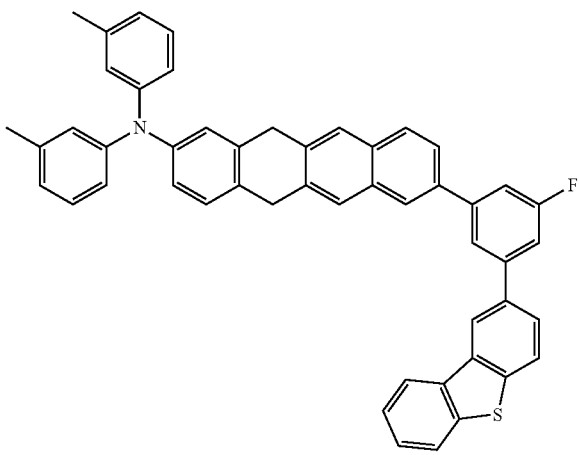

Compound 148

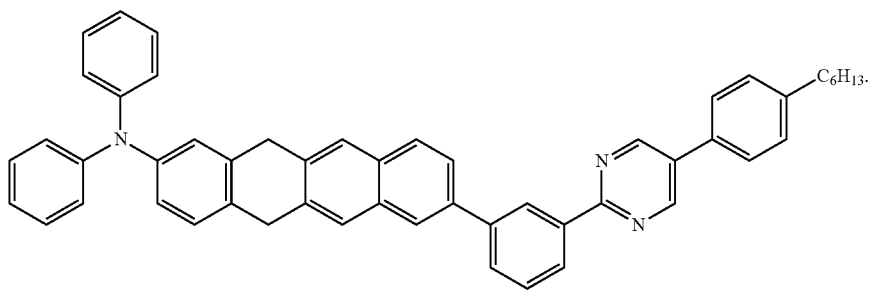

In another embodiment of the present invention, an organic electroluminescence device is disclosed. The organic electroluminescence device comprises a pair of electrodes composed of a cathode and an anode, and a light emitting layer between the pair of electrodes. The light emitting layer comprises the 5,12-dihydrotetracene derivative of formula (1) or formula (2).

In some embodiments, the light emitting layer comprising the 5,12-dihydrotetracene derivative of formula (1) or formula (2) is a thermally activated delayed fluorescence host material. In certain embodiments, the light emitting layer may further comprise a second fluorescence host material.

In some embodiments, the light emitting layer comprising the 5,12-dihydrotetracene derivative of formula (1) or formula (2) is a thermally activated delayed fluorescence dopant material. In certain embodiments, the light emitting layer may further comprise a second fluorescence dopant material.

In a further embodiment of the present invention, the organic electroluminescence device is a lighting panel. In other embodiment of the present invention, the organic electroluminescence device is a backlight panel.

Detailed preparation of the 5,12-dihydrotetracene derivatives of the present invention will be illustrated by exemplary embodiments below, nevertheless, the present invention is not limited thereto. EXAMPLES 1 to 15 show the preparation of the 5,12-dihydrotetracene derivatives of the present invention, and EXAMPLE 16 shows the fabrication and test report of the organic EL devices.

SYNTHESIS EXAMPLES

Synthesis of 6-bromo-1,4-dihydro-1,4-epoxynaphthalene

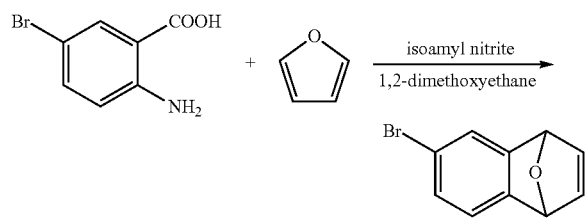

To a three-necked, round bottomed flask equipped with a condenser and two dropping funnels, furan (28.6 g, 417 mmol) and 60 ml of 1,2-dimethoxyethane were added. The two dropping funnels contained isoamyl nitrite (10 g, 84 mmol) diluted with 30 mL of DME and 2-amino-5-bromobenzoic acid (18.1 g, 84 mmol) dissolved in 30 mL of DME, respectively. The reaction mixture was heated to 70° C. in a water bath. While vigorously stirring, the isoamyl nitrite solution and the 2-amino-5-bromobenzoic acid solution were dropped slowly over 10 mins. The reaction temperature was kept at 70° C. for 1 hr, and then cooled down to room temperature. Subsequently, the solvent was removed under reduced pressure, and the crude product was purified by column chromatography, yielding 8.78 g of orange liquid (47%). $^1$H NMR (CDCl$_3$, 400 MHz): chemical shift (ppm) 7.41 (s, 1H), 7.12 (d, 1H), 7.10 (s, 2H), 7.04 (d, 1H), 5.70 (s, 2H).

Synthesis of 2,8-dibromo-5,5a,6,11,11a,12-hexahydro-5,12-epoxynaphthalene

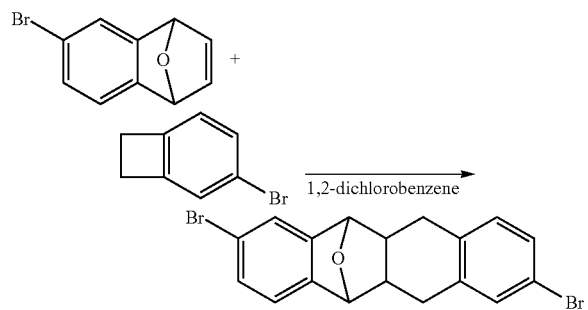

To a sealed tube, 6-bromo-1,4-dihydro-1,4-epoxynaphthalene (8 g, 34.3 mmol), 4-bromo-1,2-dihydrocyclo-butabenzene (6.28 g, 34.3 mmol), and 20 ml of 1,2-dichlorobenzene were added. The sealed tube was placed in a 220° C. preheated bath and vigorously stirred for 6 hrs. After cooling down, the solvent was removed under reduced pressure, and the crude product was purified by column chromatography, yielding 6.55 g of yellow solid (45%). $^1$H NMR (CDCl$_3$, 400 MHz): chemical shift (ppm) 7.41 (d, 1H), 7.31 (m, 1H), 7.28 (s, 1H), 7.26 (d, 1H), 7.14 (d, 1H), 7.02 (d, 1H), 5.11 (s, 2H), 3.02-2.95 (m, 2H), 2.77-2.62 (m, 2H), 2.05-1.94 (m, 2H).

Synthesis of 2,8-dibromo-5,12-dihydrotetracene

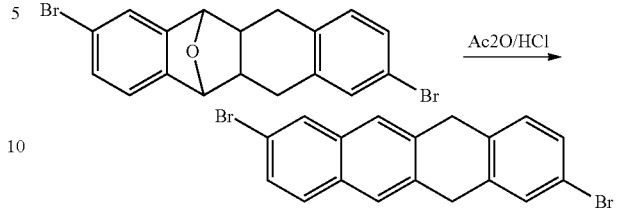

The compound 2,8-dibromo-5,5a,6,11,11a,12-hexahydro-5,12-epoxynaphthalene (6 g, 2.1 mmol) was mixed with 150 ml of acetic anhydride. To the mixture, 35 ml of concentrated HCl was added slowly and the reaction mixture was refluxed for 6 hrs. After cooling down, ice-cold water was added to the reaction mixture to form a white precipitate. The white precipitate was filtered and rinsed with methanol. The crude product was reprecipitated in a solution of CH$_2$Cl$_2$ and methanol, yielding 3.5 g of white solid (61%). $^1$H NMR (CDCl$_3$, 400 MHz): chemical shift (ppm) 7.96 (d, 1H), 7.73 (s, 1H), 7.68 (d, 1H), 7.67 (s, 1H), 7.51 (dd, 1H), 7.50 (s, 1H), 7.36 (dd, 1H), 7.22 (d, 1H), 4.05 (d, 2H), 4.03 (d, 2H).

Example 1

Synthesis of 9-(8-bromo-6,11-dihydrotetracen-2-yl)-9H-carbazole and 9-(8-bromo-5,12-dihydrotetracen-2-yl)-9H-carbazole

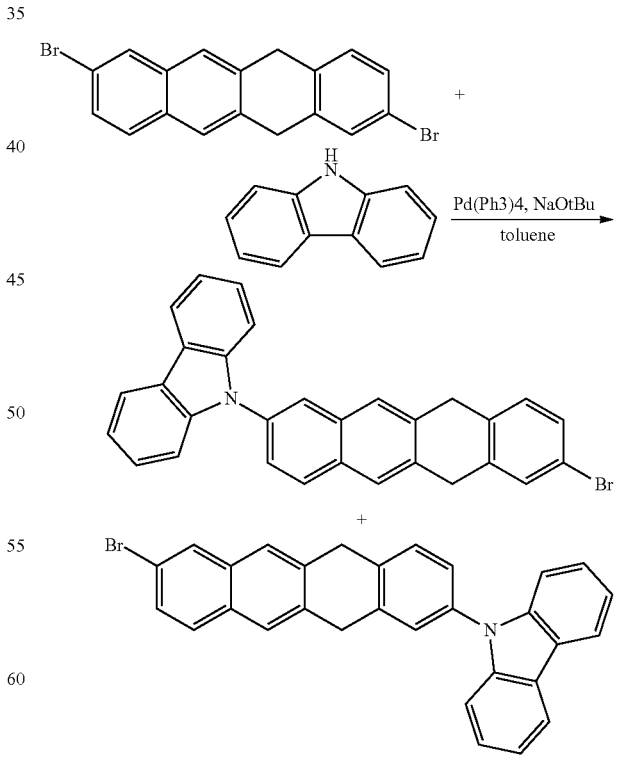

A mixture of 3.5 g (9 mmol) of 2,8-dibromo-5,12-dihydrotetracene, 1.5 g (9 mmol) of carbazole, 0.2 g (0.18 mmol) of Pd(Ph$_3$)$_4$, 1.73 g (18 mmol) of sodium tert-butoxide, and 50 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 1.03 g of 9-(8-bromo-6,11-dihydrotetracen-2-yl)-9H-carbazole as yellow solid (24%), $^1$H NMR (CDCl$_3$, 400 MHz): chemical shift (ppm) 8.56 (d, 1H), 8.13 (d, 1H), 7.99 (d, 1H), 7.94 (d, 1H), 7.78 (s, 1H), 7.65 (d, 1H), 7.49 (m, 2H), 7.41 (s, 2H), 7.35 (d, 1H), 7.32 (m, 2H), 7.28 (dd, 1H) 7.25 (dd, 1H), 7.21 (d, 1H), 4.02 (d, 2H), 3.99 (d, 2H), and yielding 1.84 g of 9-(8-bromo-5,12-dihydrotetracen-2-yl)-9H-carbazole as yellow solid (43%), $^1$H NMR (CDCl$_3$, 400 MHz): chemical shift (ppm) 8.55 (d, 1H), 8.18 (s, 1H), 8.12 (d, 1H), 7.94 (d, 1H), 7.87 (d, 1H), 7.64 (d, 1H), 7.49 (dd, 1H), 7.41 (m, 2H), 7.31 (m, 4H), 7.28 (dd, 1H), 7.25 (dd, 1H), 7.21 (d, 1H), 4.01 (d, 2H), 3.98 (d, 2H).

Synthesis of 9-(8-(4,6-diphenyl-1,3,5-triazin-2-yl)-6,11-dihydro-tetracen-2-yl)-9H-carbazole (Compound 5)

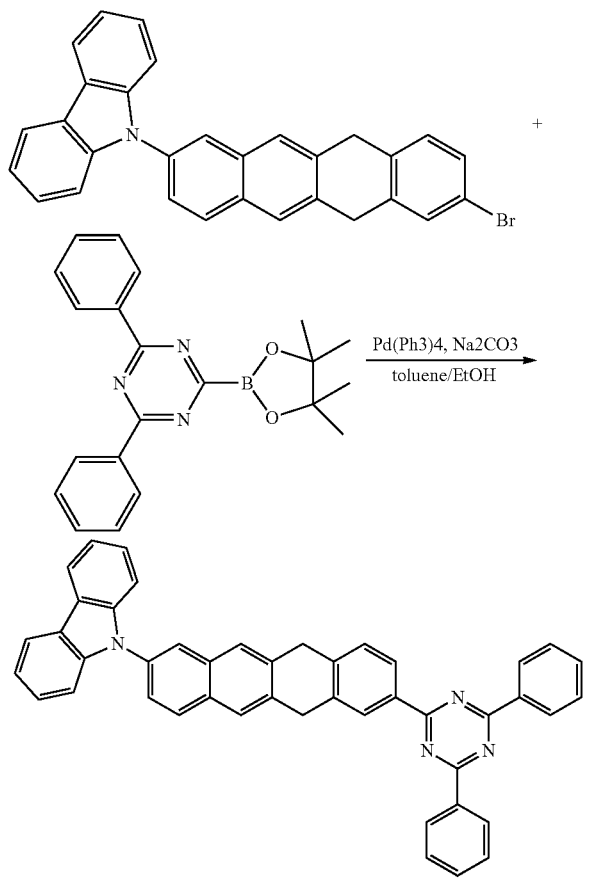

A mixture of 1.03 g (2.17 mmol) of 9-(8-bromo-6,11-dihydrotetracen-2-yl)-9H-carbazole, 0.93 g (2.6 mmol) of 2,4-diphenyl-6-(4,4,5,5-tetramethyl-1,3,2-dioxaborolan-2-yl)-1,3,5-triazine, 0.05 g (0.04 mmol) of Pd(PPh$_3$)$_4$, 2 ml of 2 M Na$_2$CO$_{3(aq)}$, 5 ml of EtOH, and 15 ml of toluene was degassed and placed under nitrogen, and then heated at 100° C. for 12 hrs. After the reaction finished, the mixture was allowed to cool to room temperature. Subsequently, 100 ml of methanol was added, and then the mixture was filtered and washed by methanol to get a white solid. Yield: 0.94 g, 69%. $^1$H NMR (CDCl$_3$, 400 MHz): chemical shift (ppm) 8.57 (d, 1H), 8.28 (d, 4H), 8.23 (d, 1H), 8.11 (d, 1H), 7.96 (d, 1H), 7.92 (d, 1H), 7.80 (s, 1H), 7.71 (s, 1H), 7.64 (d, 1H), 7.57 (m, 1H), 7.48-7.53 (m, 6H), 7.40-7.42 (m, 4H), 7.37 (d, 1H), 7.26-7.32 (m, 2H), 4.01 (d, 2H), 3.98 (d, 2H). MS (m/z, EI$^+$): 626.4.

Example 2

Synthesis of 9-(8-(4,6-diphenyl-1,3,5-triazin-2-yl)-5,12-dihydro-tetracen-2-yl)-9H-carbazole (Compound 6)

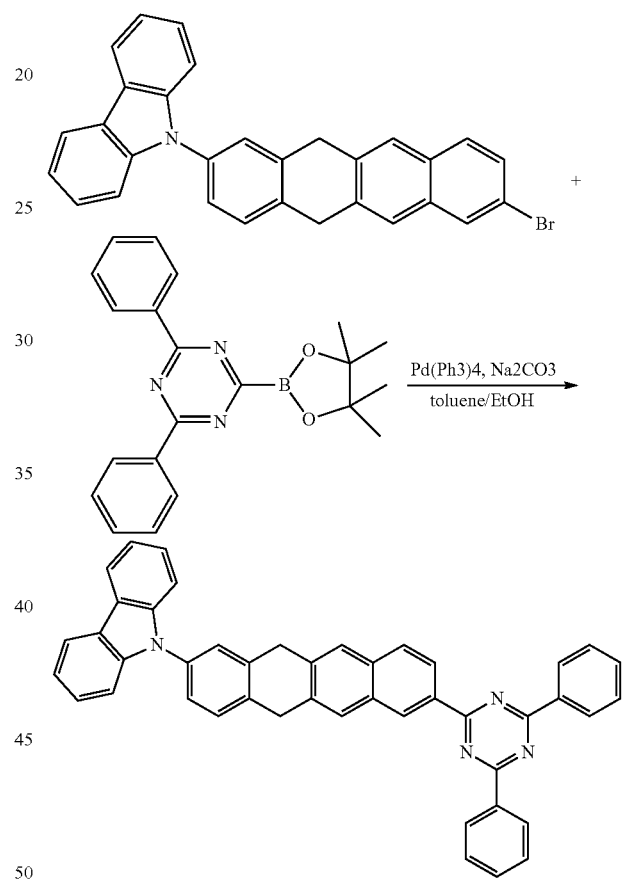

A mixture of 1.84 g (3.88 mmol) of 9-(8-bromo-5,12-dihydrotetracen-2-yl)-9H-carbazole, 1.67 g (4.64 mmol) of 2,4-diphenyl-6-(4,4,5,5-tetramethyl-1,3,2-dioxaborolan-2-yl)-1,3,5-triazine, 0.09 g (0.08 mmol) of Pd(PPh$_3$)$_4$, 4 ml of 2 M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, 150 ml of methanol was added, and then the mixture was filtered and washed by methanol to get a white solid. Yield: 1.51 g, 62%. $^1$H NMR (CDCl$_3$, 400 MHz): chemical shift (ppm) 8.56 (d, 1H), 8.29 (d, 4H), 8.25 (d, 1H), 8.13 (d, 1H), 7.95 (d, 1H), 7.91 (d, 1H), 7.72 (s, 1H), 7.68 (d, 1H), 7.64 (d, 1H), 7.55-7.58 (m, 4H), 7.48-7.50 (m, 2H), 7.39-7.42 (m, 2H), 7.29-7.3 (m, 4H), 7.25 (dd, 1H), 7.19 (d, 1H), 4.03 (d, 2H), 3.99 (d, 2H). MS (m/z, EI$^+$): 626.8.

Example 3

Synthesis of 9-(8-(3-(4,6-diphenyl-1,3,5-triazin-2-yl)phenyl)-6,11-dihydrotetracen-2-yl)-9H-carbazole (Compound 1)

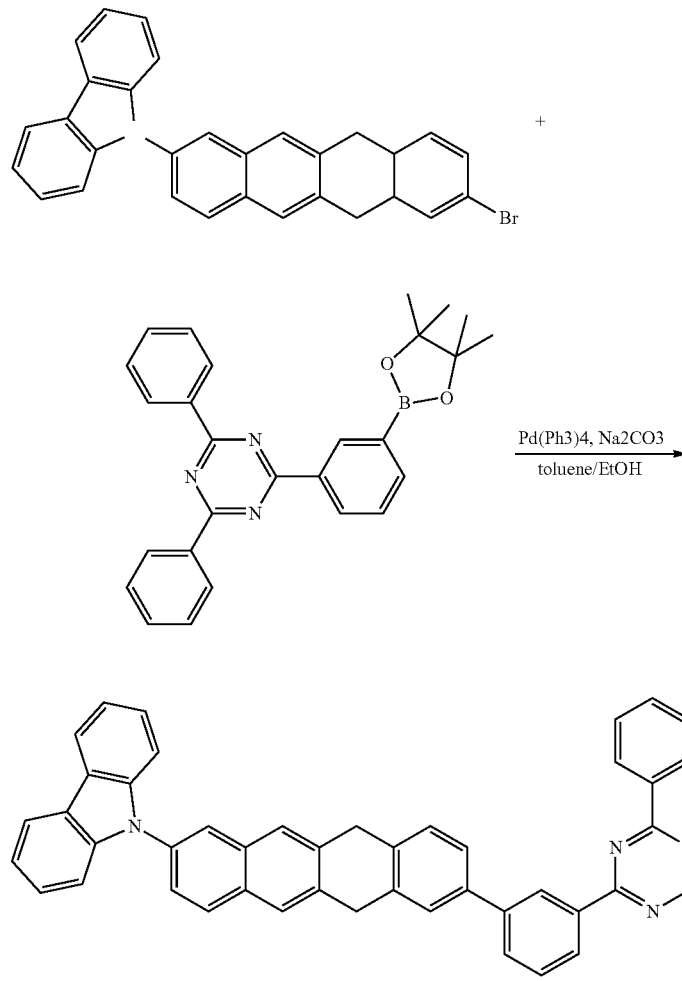

A mixture of 1.33 g (2.8 mmol) of 9-(8-bromo-6,11-dihydrotetracen-2-yl)-9H-carbazole, 1.46 g (3.36 mmol) of 2,4-diphenyl-6-(3-(4,4,5,5-tetramethyl-1,3,2-dioxaborolan-2-yl)phenyl) 1,3,5-triazine, 0.06 g (0.05 mmol) of Pd(PPh$_3$)$_4$, 2 ml of 2 M Na$_2$CO$_{3(aq)}$, 5 ml of EtOH, and 15 ml of toluene was degassed and placed under nitrogen, and then heated at 100° C. for 12 hrs. After the reaction finished, the mixture was allowed to cool to room temperature. Subsequently, 100 ml of methanol was added, and then the mixture was filtered and washed by methanol to get a white solid. Yield: 1.26 g, 64%. MS (m/z, EI$^+$): 702.4.

Example 4

Synthesis of 9-(8-(3-(4,6-diphenyl-1,3,5-triazin-2-yl)phenyl)-5,12-dihydrotetracen-2-yl)-9H-carbazole (Compound 2)

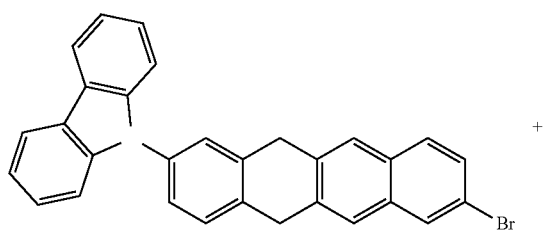

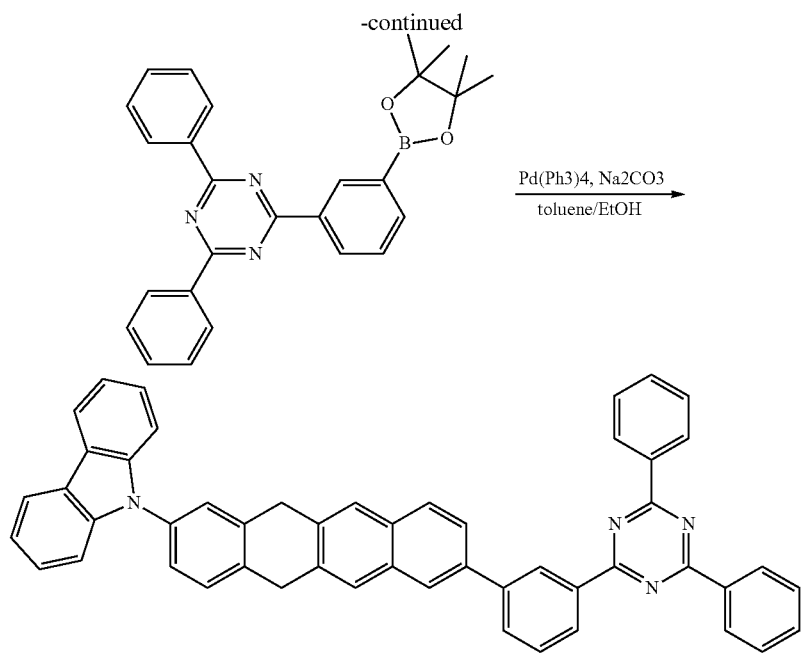

A mixture of 1.73 g (3.63 mmol) of 9-(8-bromo-5,12-dihydrotetracen-2-yl)-9H-carbazole, 1.89 g (4.34 mmol) of 2,4-diphenyl-6-(3-(4,4,5,5-tetramethyl-1,3,2-dioxaborolan-2-yl)phenyl) 1,3,5-triazine, 0.07 g (0.06 mmol) of Pd(PPh$_3$)$_4$, 4 ml of 2 M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, 150 ml of methanol was added, and then the mixture was filtered and washed by methanol to get a white solid. Yield: 1.51 g, 59%. MS (m/z, EI$^+$): 702.6.

Example 5

Synthesis of 10-(8-bromo-6,11-dihydrotetracen-2-yl)-9,9-dimethyl-9,10-dihydroacridine and 10-(8-bromo-5,12-dihydrotetracen-2-yl)-9,9-dimethyl-9,10-dihydroacridine

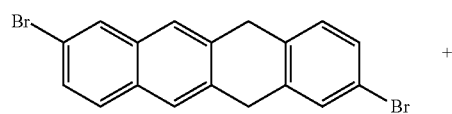

+

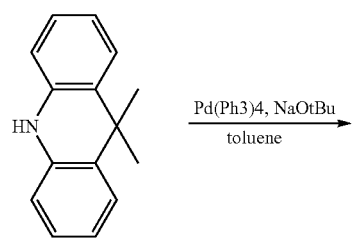

Pd(Ph$_3$)$_4$, NaOtBu / toluene →

-continued

[structure]

+

[structure]

A mixture of 3.5 g (9 mmol) of 2,8-dibromo-5,12-dihydrotetracene, 1.89 g (9 mmol) of 9,9-dimethyl-9,10-dihydroacridine, 0.2 g (0.18 mmol) of Pd(Ph$_3$)$_4$, 1.73 g (18 mmol) of sodium tert-butoxide, and 50 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 0.98 g of 10-(8-bromo-6,11-dihydrotetracen-2-yl)-9,9-dimethyl-9,10-dihydroacridine as yellow solid (21%), $^1$H NMR (CDCl$_3$, 400 MHz): chemical shift (ppm) 7.85 (s, 1H), 7.74 (s, 1H), 7.44-7.25 (m, 6H), 7.11-7.03 (m, 4H), 6.74-6.69 (m, 2H), 6.61-6.54 (m, 2H), 3.94 (d, 2H), 3.91 (d, 2H), 1.73 (s, 6H) and yielding 1.63 g of 10-(8-bromo-5,12-dihydrotetracen-2-yl)-9,9-dimethyl-9,10-dihydroacridine as yellow solid (35%), $^1$H NMR (CDCl$_3$, 400 MHz): chemical shift (ppm) 7.83 (s, 1H), 7.72 (s, 1H), 7.41-7.27 (m, 6H), 7.09-7.02 (m, 4H), 6.74-6.67 (m, 2H), 6.59-6.53 (m, 2H), 3.98 (d, 2H), 3.93 (d, 2H), 1.72 (s, 6H).

Synthesis of 5-(8-(9,9-dimethylacridin-10(9H)-yl)-5,12-dihydro-tetracen-2-yl)isophthalonitrile (Compound 47)

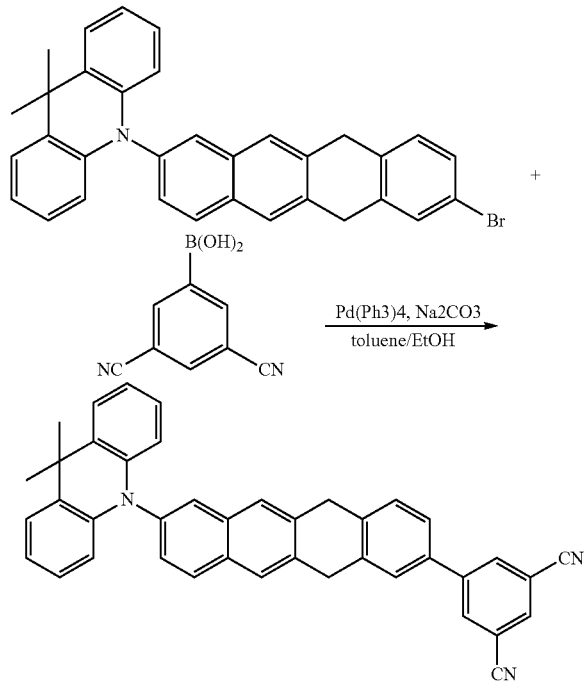

A mixture of 1.1 g (2.13 mmol) of 10-(8-bromo-6,11-dihydrotetracen-2-yl)-9,9-dimethyl-9,10-dihydroacridine, 0.44 g (2.56 mmol) of (3,5-dicyano-phenyl)boronic acid, 0.05 g (0.04 mmol) of Pd(PPh$_3$)$_4$, 2 ml of 2 M Na$_2$CO$_{3(aq)}$, 5 ml of EtOH, and 15 ml of toluene was degassed and placed under nitrogen, and then heated at 100° C. for 12 hrs. After the reaction finished, the mixture was allowed to cool to room temperature. Subsequently, 100 ml of methanol was added, and then the mixture was filtered and washed by methanol to get a pale yellow solid. Yield: 0.8 g, 67%. MS (m/z, EI$^+$): 563.8.

Example 6

Synthesis of 5-(8-(9,9-dimethylacridin-10(9H)-yl)-6,11-dihydro-tetracen-2-yl)isophthalonitrile (Compound 48)

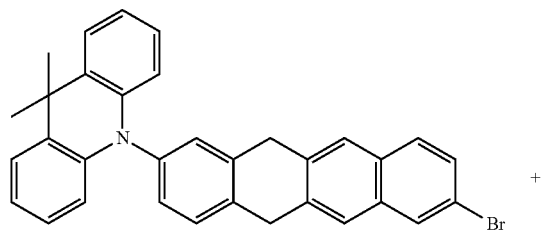

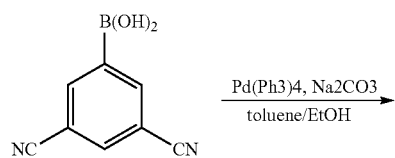

A mixture of 1.3 g (2.52 mmol) of 10-(8-bromo-5,12-dihydrotetracen-2-yl)-9,9-dimethyl-9,10-dihydroacridine, 1.67 g (4.64 mmol) of (3,5-dicyano-phenyl)boronic acid, 0.05 g (0.04 mmol) of Pd(PPh$_3$)$_4$, 4 ml of 2 M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, 150 ml of methanol was added, and then the mixture was filtered and washed by methanol to get a pale yellow solid. Yield: 1 g, 71%. MS (m/z, EI$^+$): 563.9.

Example 7

Synthesis of 10-(8-bromo-6,11-dihydrotetracen-2-yl)-10H-phenoxazine and 10-(8-bromo-5,12-dihydrotetracen-2-yl)-10H-phenoxazine

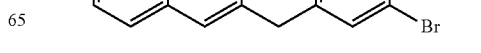

-continued

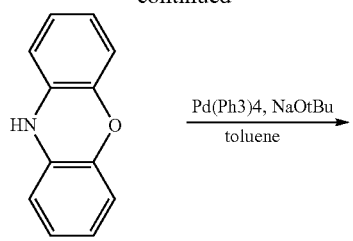

Synthesis of 10-(8-(4-(phenylsulfonyl)phenyl)-6,11-dihydrotetracen-2-yl)-10H-phenoxazine (Compound 69)

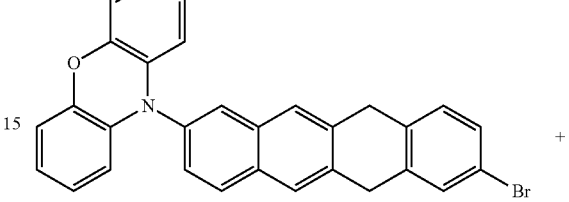

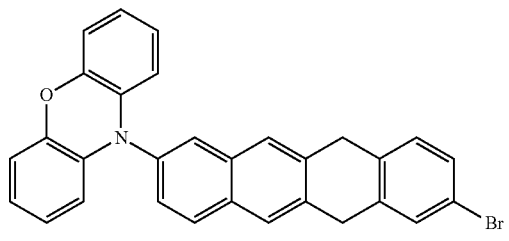

+

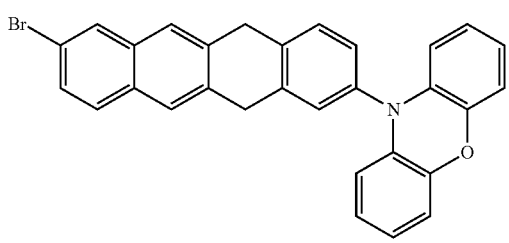

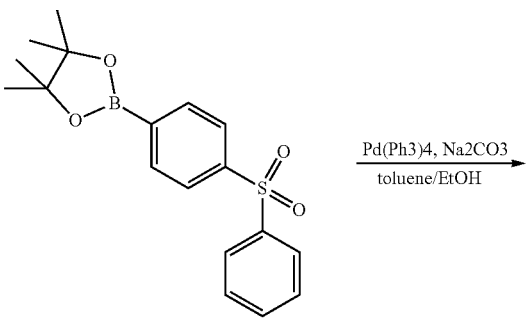

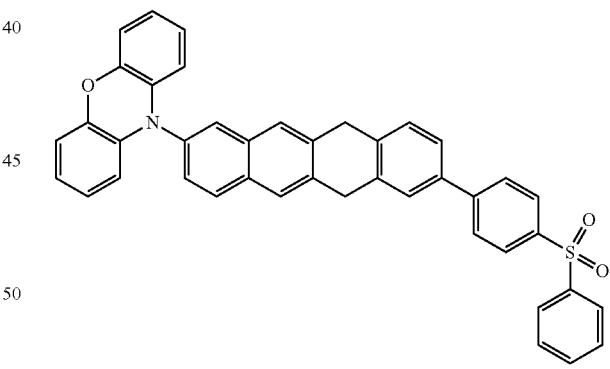

A mixture of 4 g (10.3 mmol) of 2,8-dibromo-5,12-dihydrotetracene, 1.89 g (9 mmol) of 10H-phenoxazine, 0.23 g (0.2 mmol) of Pd(Ph$_3$)$_4$, 1.9 g (20 mmol) of sodium tert-butoxide, and 50 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 1.11 g of 10-(8-bromo-6,11-dihydrotetracen-2-yl)-10H-phenoxazine as yellow solid (22%), $^1$H NMR (CDCl$_3$, 400 MHz): chemical shift (ppm) 7.91 (s, 1H), 7.82 (s, 1H), 7.52-7.33 (m, 6H), 7.17-7.09 (m, 4H), 6.82-6.71 (m, 2H), 6.63-6.56 (m, 2H), 3.95 (d, 2H), 3.92 (d, 2H) and yielding 1.92 g of 10-(8-bromo-5,12-dihydrotetracen-2-yl)-10H-phenoxazine as yellow solid (38%), $^1$H NMR (CDCl$_3$, 400 MHz): chemical shift (ppm) 7.93 (s, 1H), 7.85 (s, 1H), 7.61-7.41 (m, 6H), 7.18-7.09 (m, 4H), 6.84-6.72 (m, 2H), 6.67-6.59 (m, 2H), 4.01 (d, 2H), 3.96 (d, 2H).

A mixture of 1.2 g (2.45 mmol) of 10-(8-bromo-6,11-dihydrotetracen-2-yl)-10H-phenoxazine, 1.01 g (2.94 mmol) of 4,4,5,5-tetramethyl-2-(4-(phenylsulfonyl)phenyl)-1,3,2-dioxaborolane, 0.05 g (0.04 mmol) of Pd(PPh$_3$)$_4$, 2 ml of 2 M Na$_2$CO$_{3(aq)}$, 5 ml of EtOH, and 15 ml of toluene was degassed and placed under nitrogen, and then heated at 100° C. for 12 hrs. After the reaction finished, the mixture was allowed to cool to room temperature. Subsequently, 100 ml of methanol was added, and then the mixture was filtered and washed by methanol to get a pale yellow solid. Yield: 0.88 g, 58%. MS (m/z, EI$^+$): 627.9.

Example 8

Synthesis of 10-(8-(4-(phenylsulfonyl)phenyl)-5,12-dihydrotetracen-2-yl)-10H-phenoxazine (Compound 70)

Example 9

Synthesis of (4-(8-(1-methyl-9H-carbazol-9-yl)-5,12-dihydro-tetracen-2-yl)phenyl)(phenyl)methanone (Compound 51)

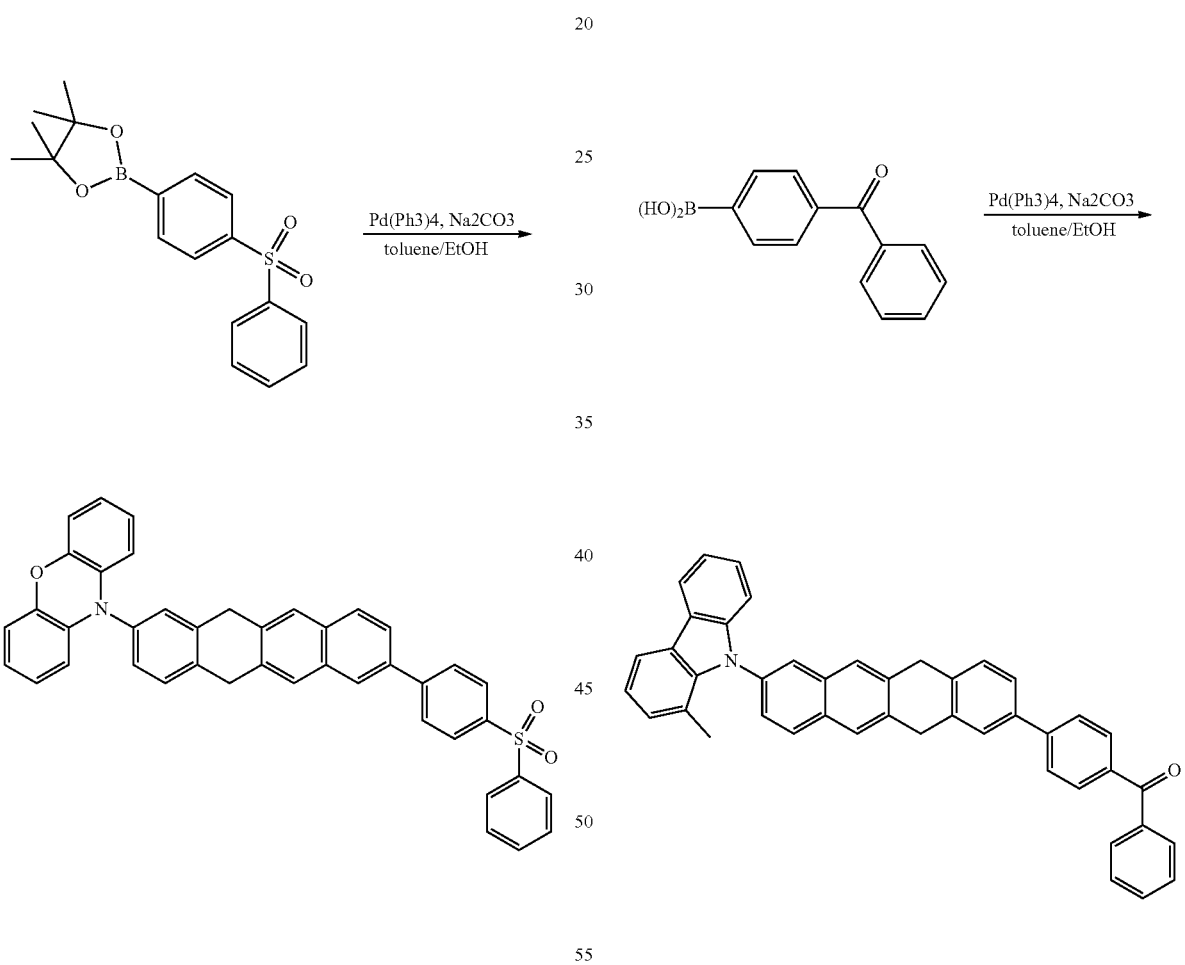

A mixture of 1.5 g (3.06 mmol) of 10-(8-bromo-5,12-dihydrotetracen-2-yl)-10H-phenoxazine, 1.26 g (3.67 mmol) of 4,4,5,5-tetramethyl-2-(4-(phenylsulfonyl)phenyl)-1,3,2-dioxaborolane, 0.05 g (0.04 mmol) of Pd(PPh$_3$)$_4$, 4 ml of 2 M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, 150 ml of methanol was added, and then the mixture was filtered and washed by methanol to get a pale yellow solid. Yield: 1.19 g, 62%. MS (m/z, EI$^+$): 627.8.

The same synthesis procedure as in EXAMPLE 1 was used, except that 9-(8-bromo-6,11-dihydrotetracen-2-yl)-1-methyl-9H-carbazole was used instead of 9-(8-bromo-6,11-dihydrotetracen-2-yl)-9H-carbazole and (4-benzoylphenyl)boronic acid was used instead of 2,4-diphenyl-6-(4,4,5,5-tetramethyl-1,3,2-dioxaborolan-2-yl)-1,3,5-triazine to obtain the desired compound of (4-(8-(1-methyl-9H-carbazol-9-yl)-5,12-dihydro-tetracen-2-yl)phenyl)(phenyl)methanone. MS (m/z, EI$^+$): 589.4.

Example 10

Synthesis of 9-(8-(4-(4,5-diphenyl-4H-1,2,4-triazol-3-yl)phenyl)-6,11-dihydrotetracen-2-yl)-3,6-dimethoxy-9H-carbazole (Compound 53)

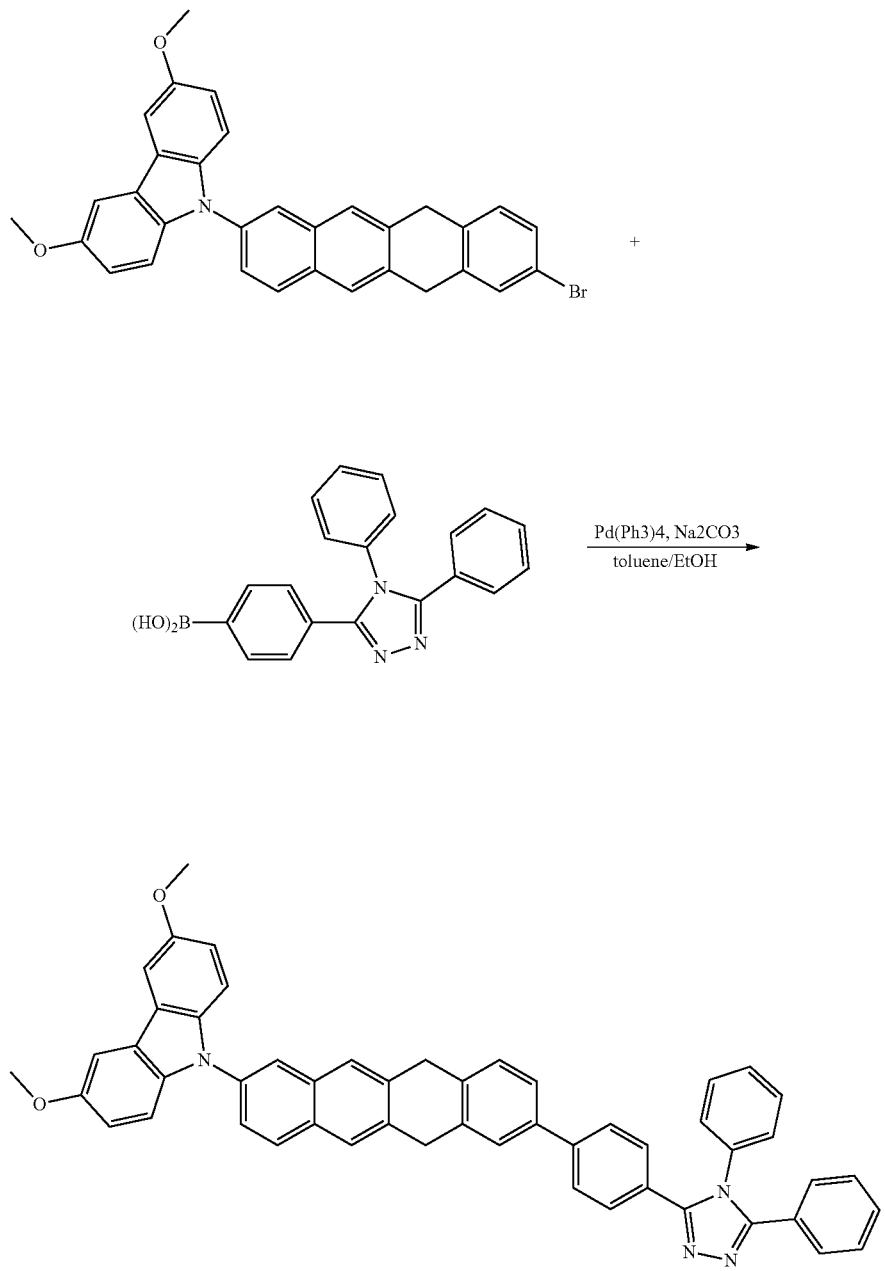

The same synthesis procedure as in EXAMPLE 1 was used, except that 9-(8-bromo-6,11-dihydrotetracen-2-yl)-3,6-dimethoxy-9H-carbazole was used instead of 9-(8-bromo-6,11-dihydrotetracen-2-yl)-9H-carbazole and (4-(4,5-diphenyl-4H-1,2,4-triazol-3-yl)phenyl)boronic acid was used instead of 2,4-diphenyl-6-(4,4,5,5-tetramethyl-1,3,2-dioxaborolan-2-yl)-1,3,5-triazine to obtain the desired compound of 9-(8-(4-(4,5-diphenyl-4H-1,2,4-triazol-3-yl)-phenyl)-6,11-dihydrotetracen-2-yl)-3,6-dimethoxy-9H-carbazole. MS (m/z, EI$^+$): 750.6.

Example 11

Synthesis of N,N-diphenyl-8-(3-phenylbenzo[c]thiophen-1-yl)-6,11-dihydrotetracen-2-amine (Compound 75)

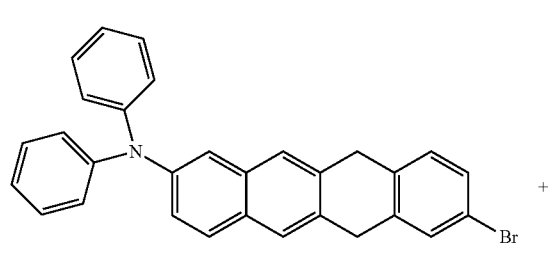
+

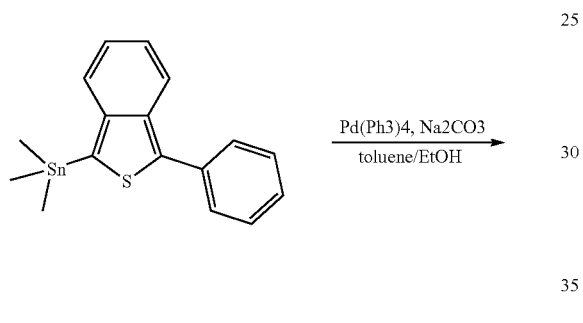

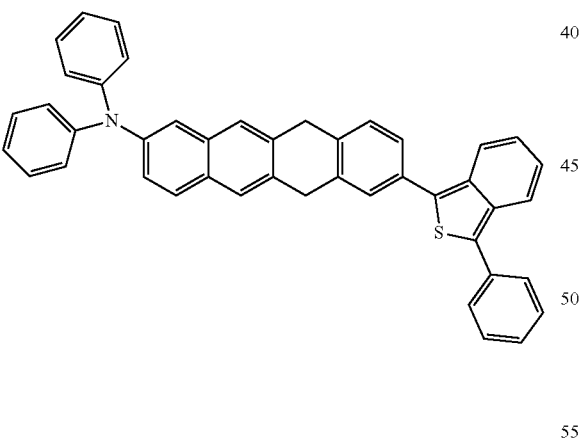

The same synthesis procedure as in EXAMPLE 1 was used, except that 8-bromo-N,N-diphenyl-6,11-dihydrotetracen-2-amine was used instead of 9-(8-bromo-6,11-dihydrotetracen-2-yl)-9H-carbazole and trimethyl(3-phenylbenzo[c]thiophen-1-yl)stannane was used instead of 2,4-diphenyl-6-(4,4,5,5-tetramethyl-1,3,2-dioxaborolan-2-yl)-1,3,5-triazine to obtain the desired compound of N,N-diphenyl-8-(3-phenylbenzo[c]thiophen-1-yl)-6,11-dihydrotetracen-2-amine. MS (m/z, EI⁻): 605.6.

Example 12

Synthesis of 10-(8-(di-m-tolylamino)-5,12-dihydrotetracen-2-yl)-10H-phenothiazine 5,5-dioxide (Compound 77)

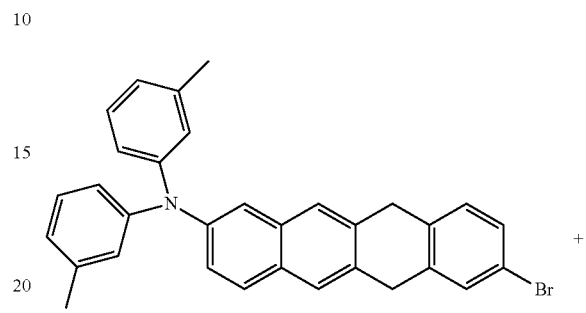
+

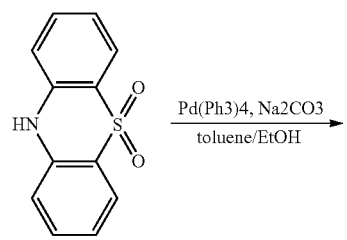

The same synthesis procedure as in EXAMPLE 1 was used, except that 8-bromo-N,N-di-m-tolyl-6,11-dihydrotetracen-2-amine was used instead of 9-(8-bromo-6,11-dihydrotetracen-2-yl)-9H-carbazole and 10H-phenothiazine 5,5-dioxide was used instead of 2,4-diphenyl-6-(4,4,5,5-tetramethyl-1,3,2-dioxaborolan-2-yl)-1,3,5-triazine to obtain the desired compound of 10-(8-(di-m-tolylamino)-5,12-dihydrotetracen-2-yl)-10H-phenothiazine 5,5-dioxide. MS (m/z, EI⁺): 654.5.

Example 13

Synthesis of 2-(8-(9'H-[9,3': 6',9''-tercarbazol]-9'-yl)-5,12-dihydro-tetracen-2-yl)dibenzo[b,d]thiophene 5,5-dioxide (Compound 79)

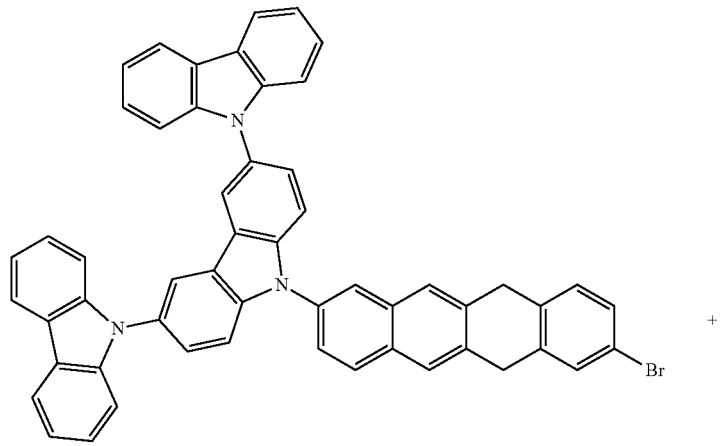

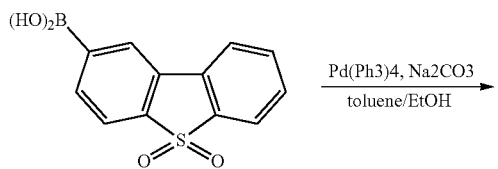

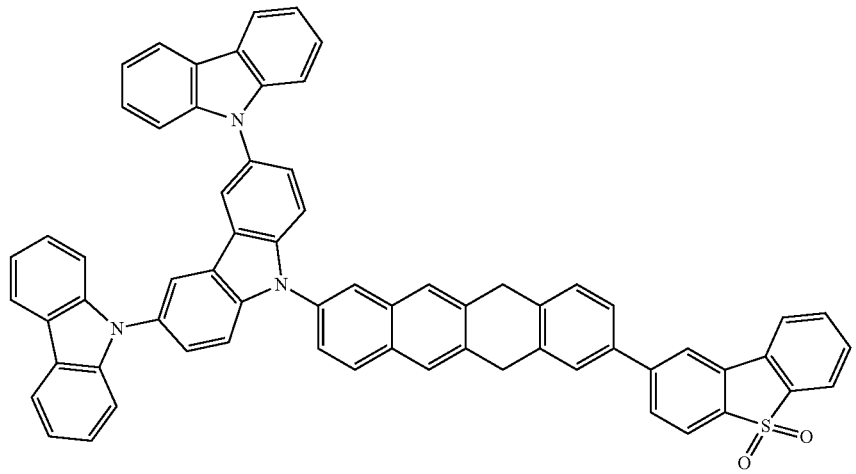

The same synthesis procedure as in EXAMPLE 1 was used, except that 9'(8-bromo-6,11-dihydrotetracen-2-yl)-9'H-9,3':6',9''-terbenzo[b]indole was used instead of 9-(8-bromo-6,11-dihydrotetracen-2-yl)-9H-carbazole and (5,5-dioxidodibenzo[b,d]thiophen-2-yl)boronic acid was used instead of 2,4-diphenyl-6-(4,4,5,5-tetramethyl-1,3,2-dioxaborolan-2-yl)-1,3,5-triazine to obtain the desired compound of 2-(8-(9'H-[9,3': 6',9''-tercarbazol]-9'-yl)-5,12-dihydrotetracen-2-yl)dibenzo[b,d]thiophene 5,5-dioxide. MS (m/z, EI$^+$): 940.4.

Example 14

Synthesis of 9-(8-(8-phenylquinoxalin-5-yl)-6,11-dihydrotetracen-2-yl)-9H-carbazole (Compound 81)

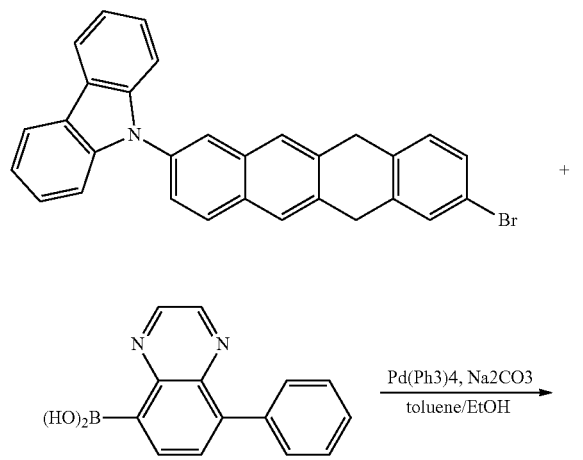

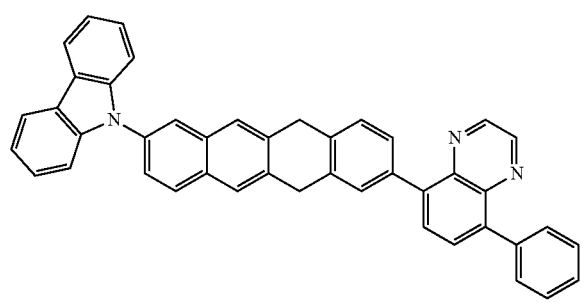

The same synthesis procedure as in EXAMPLE 1 was used, except that (8-phenylquinoxalin-5-yl)boronic acid was used instead of 2,4-diphenyl-6-(4,4,5,5-tetramethyl-1,3,2-dioxaborolan-2-yl)-1,3,5-triazine to obtain the desired compound of 9-(8-(8-phenylquinoxalin-5-yl)-6,11-dihydrotetracen-2-yl)-9H-carbazole. MS (m/z, EI⁺): 599.4.

Example 15

Synthesis of 10-(8-(1,3-diphenyl-1H-indol-5-yl)-5,12-dihydro-tetracen-2-yl)-10H-phenoxazine (Compound 106)

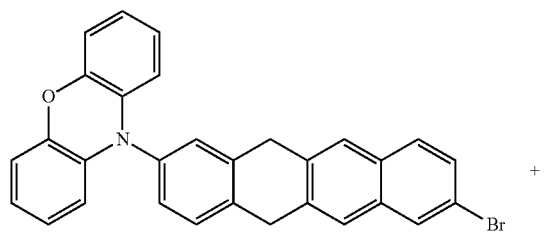

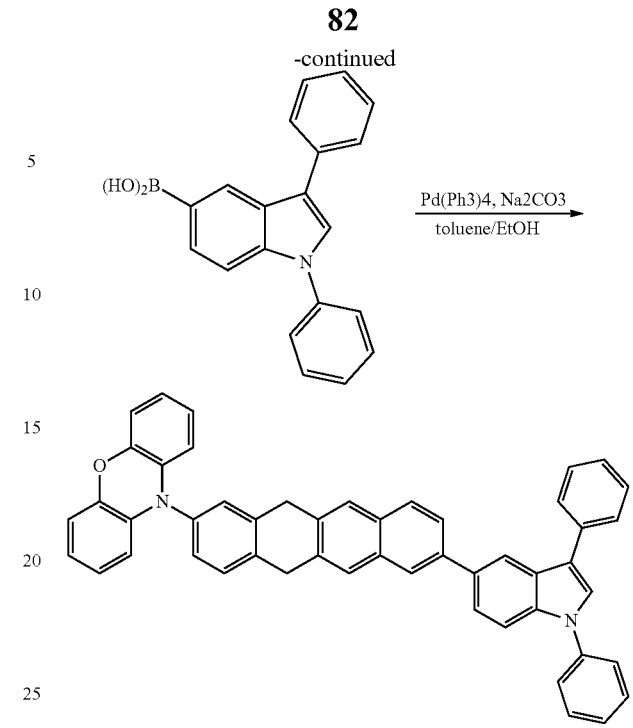

The same synthesis procedure as in EXAMPLE 2 was used, except that 10-(8-bromo-5,12-dihydrotetracen-2-yl)-10H-phenoxazine was used instead of 9-(8-bromo-5,12-dihydrotetracen-2-yl)-9H-carbazole and (1,3-diphenyl-1H-indol-5-yl)boronic acid was used instead of 2,4-diphenyl-6-(4,4,5,5-tetramethyl-1,3,2-dioxaborolan-2-yl)-1,3,5-triazine to obtain the desired compound of 10-(8-(1,3-diphenyl-1H-indol-5-yl)-5,12-dihydro-tetracen-2-yl)-10H-phenoxazine. MS (m/z: EI⁺): 678.5.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10⁻⁷ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is successfully achieved by co-vaporization from two or more sources, which means the 5,12-dihydrotetracene derivatives of the present invention are thermally stable.

Dipyrazino[2,3-f:2,3-]quinoxaline-2,3,6,7,10,11-hexacarbonitrile (HAT-CN) is used to form the hole injection layer of the organic EL device. N,N-bis(naphthalene-1-yl)-N,N-bis(phenyl)-benzidine (NPB) is used to form the hole transporting layer. Dibenzo[b,d]thiophene-2,8-diylbis(diphenylphosphine oxide) (H2) is used as the TADF host material.

2-(10,10-dimethyl-10H-indeno[2,1-b]triphenylen-13-yl)-9-phenyl-1,10-phenanthroline (ET1) is used as the electron transporting material. Compounds 1, 2, 5, 6, 47, 48, 51, 53, 75, 77, 79, 81, and 106 are used as the TADF dopant material to compare with Compound A. Compounds 69 and 70 are used as the TADF host material to compare with compound H2. The chemical structures of conventional OLED materials and the exemplary 5,12-dihydrotetracene derivatives of the present invention for producing control and exemplary organic EL devices in this invention are shown as follows:

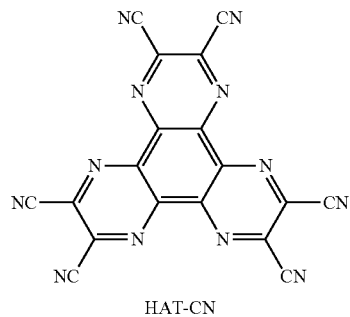

HAT-CN

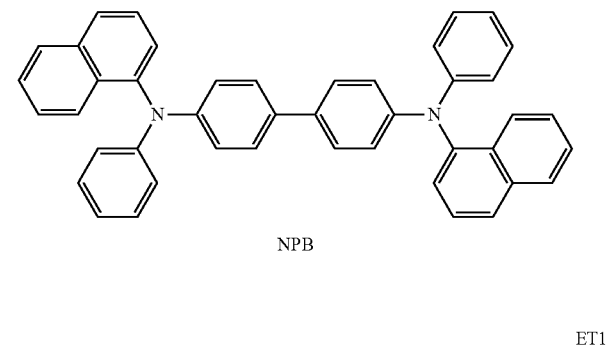

NPB

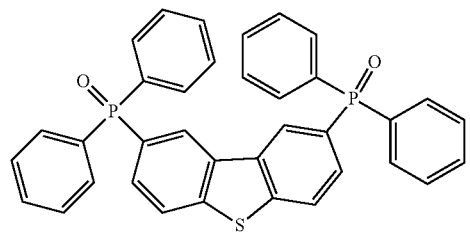

H2

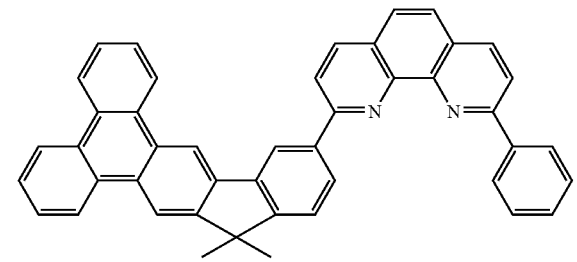

ET1

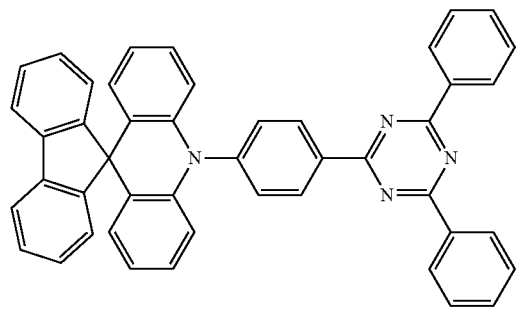

Compound A

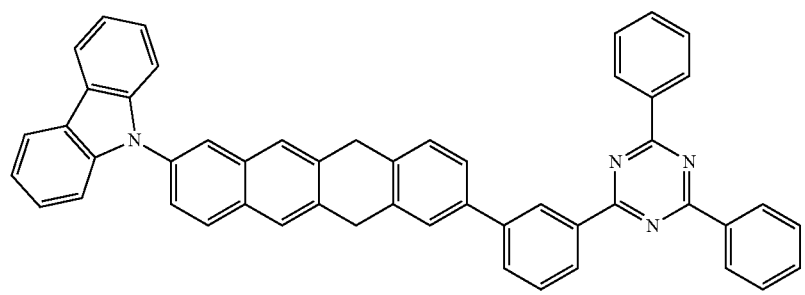

Compound 1

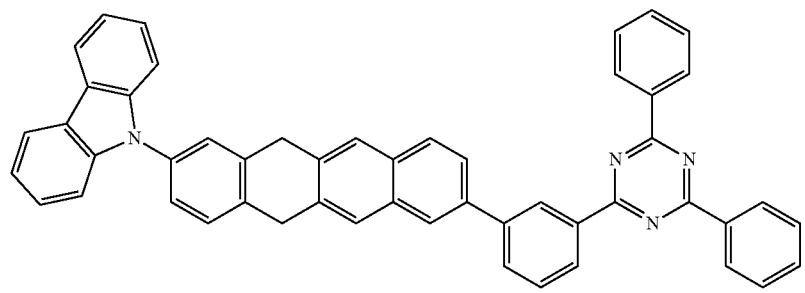

Compound 2

-continued
Compound 5
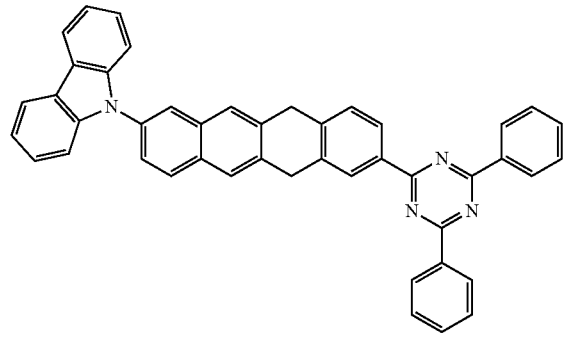
Compound 6
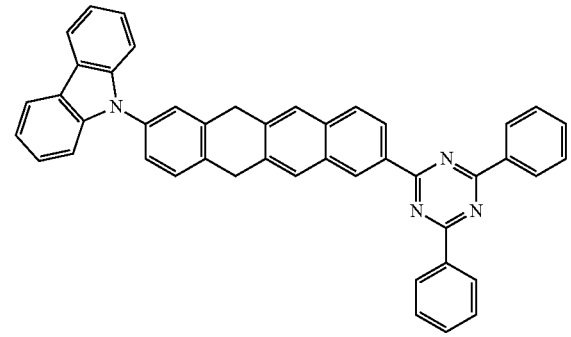
Compound 47
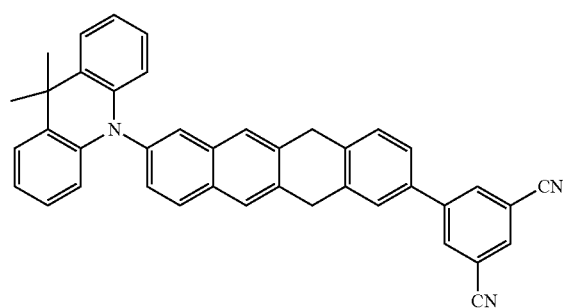
Compound 48
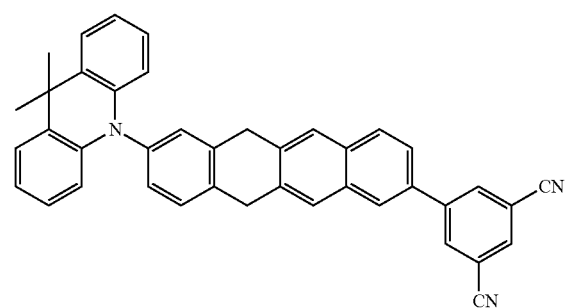
Compound 51
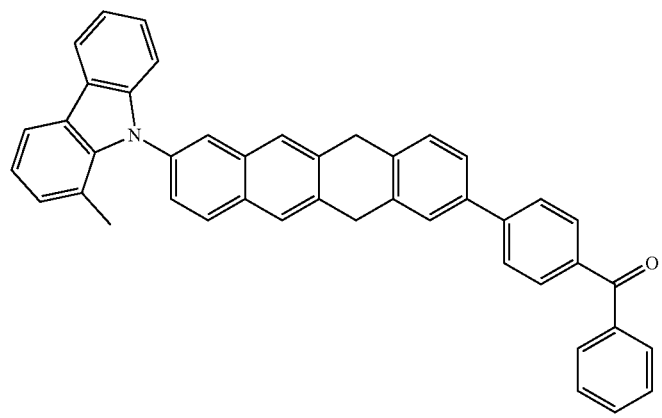
Compound 53
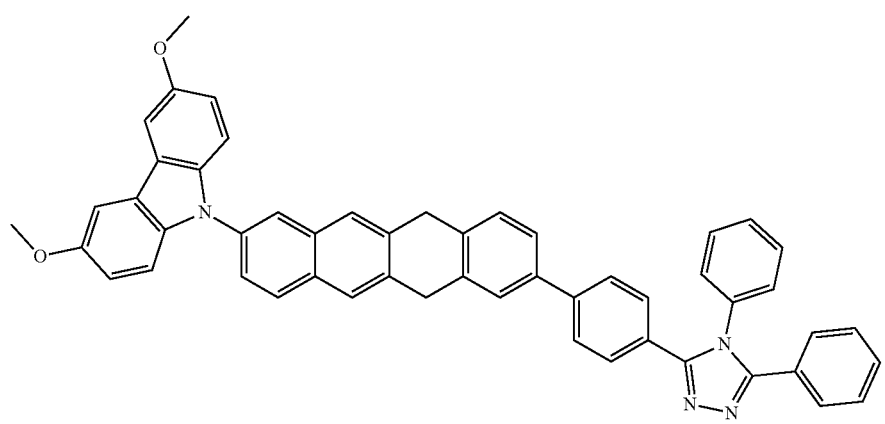

-continued
Compound 69
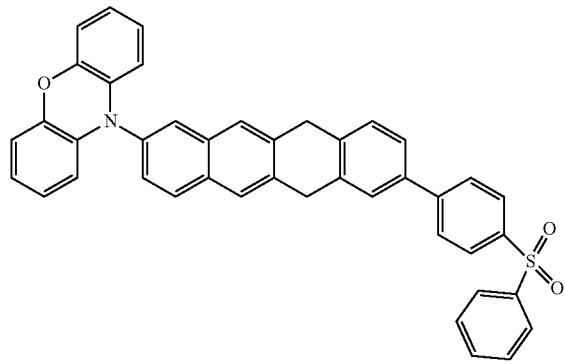
Compound 70
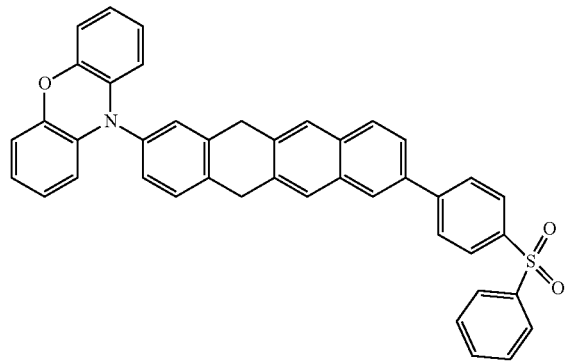
Compound 75
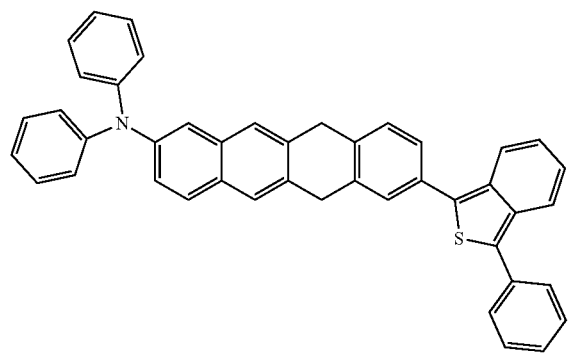
Compound 77
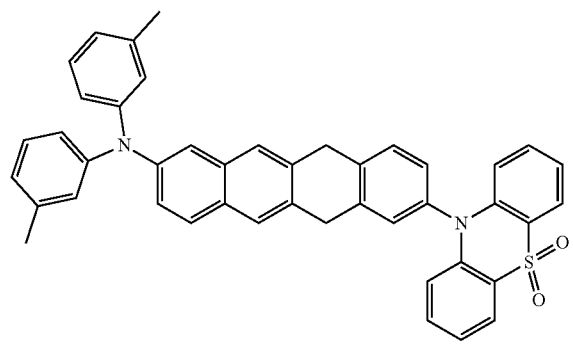
Compound 79
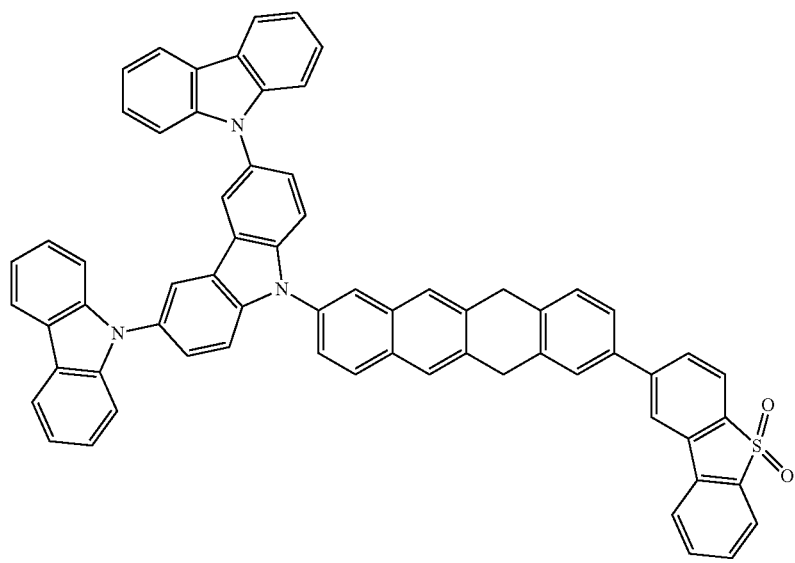

Compound 81

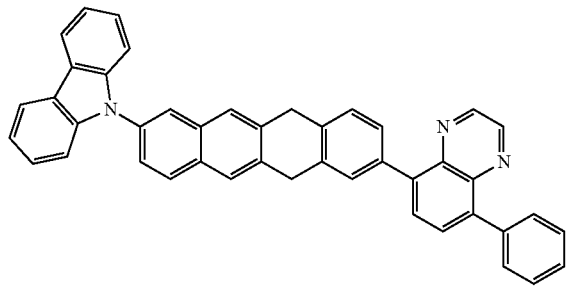

Compound 106

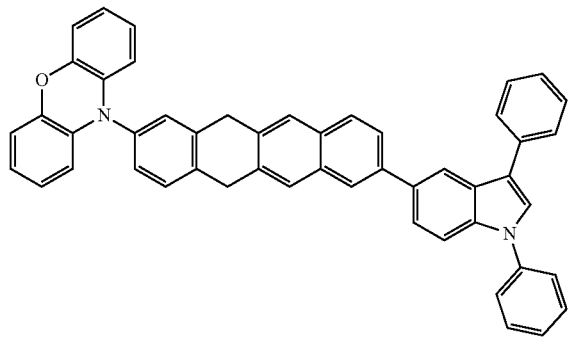

A typical organic EL device consists of thermally evaporated low work function metals, such as Al, Mg, Ca, Li and K, as the cathode, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ (as shown below), MgO, or $Li_2O$. On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

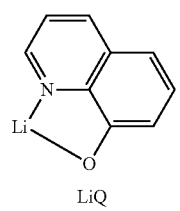

LiQ

Example 16

Using a procedure analogous to the above mentioned general method, organic EL devices emitting blue light and having the following device structure as shown in the FIGURE were produced: ITO/HAT-CN(20 nm)/NPB(130 nm)/Host doped with Dopant (30 nm)/ETM/LiQ/Al (160 nm). The I-V-B (at 1000 nits) test reports of these organic EL devices are summarized in Table 1 below.

TABLE 1

| Dopant(%) | Host | ETM | Voltage (V) | Efficiency (cd/A) |
|---|---|---|---|---|
| A(20%) | H2 | ET1 | 5 | 10 |
| Compound 5(20%) | H2 | ET1 | 4.8 | 20 |
| Compound 6(20%) | H2 | ET1 | 4.9 | 19 |
| Compound 1(20%) | H2 | ET1 | 4.5 | 18 |
| Compound 2(20%) | H2 | ET1 | 4.4 | 17 |

TABLE 1-continued

| Dopant(%) | Host | ETM | Voltage (V) | Efficiency (cd/A) |
|---|---|---|---|---|
| Compound 47(20%) | H2 | ET1 | 4.4 | 16 |
| Compound 48(20%) | H2 | ET1 | 4.4 | 17 |
| Compound 51(20%) | H2 | ET1 | 4.9 | 13 |
| Compound 53(20%) | H2 | ET1 | 4.9 | 13 |
| Compound 75(20%) | H2 | ET1 | 4.7 | 12 |
| Compound 77(20%) | H2 | ET1 | 4.8 | 11 |
| Compound 79(20%) | H2 | ET1 | 4.8 | 12 |
| Compound 81(20%) | H2 | ET1 | 4.9 | 14 |
| Compound 106(20%) | H2 | ET1 | 4.7 | 11 |
| A(20%) | Compound 69 | ET1 | 4.8 | 16 |
| A(20%) | Compound 70 | ET1 | 4.8 | 15 |

From the above test report summary of the organic EL devices, it is obvious that the 5,12-dihydrotetracene derivative of formula (1) or formula (2) used as the TADF host material or TADF dopant material of the organic EL device exhibits better performance than the prior art materials. In particular, the organic EL devices of the present invention employing the 5,12-dihydrotetracene derivative of formula (1) or formula (2) as the TADF host material or TADF dopant material to collocate with the host material H2 or the dopant material Compound A have lower power consumption and higher current efficiency.

To sum up, the present invention discloses a 5,12-dihydrotetracene derivative, which can be used as the thermally activated delayed fluorescence host material or the thermally activated delayed fluorescence dopant material in the light emitting layer of the organic EL device. The mentioned 5,12-dihydrotetracene derivative is represented by the following formula (1) or formula (2):

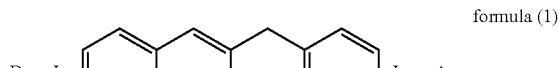

formula (1)

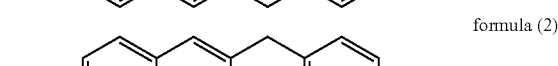

formula (2)

wherein L represents a single bond, a substituted or unsubstituted divalent arylene group having 6 to 30 ring carbon atoms, or a substituted or unsubstituted divalent heteroarylene group having 6 to 30 ring carbon atoms; D is an electron donor moiety selected from the group consisting of a substituted or unsubstituted carbazolyl group, a substituted or unsubstituted biscarbazolyl group, a substituted or unsubstituted dihydroacridine group, a substituted or unsubstituted phenoxazine group, and a substituted or unsubstituted diarylamine group; and A is an electron acceptor moiety selected from the following formulas:

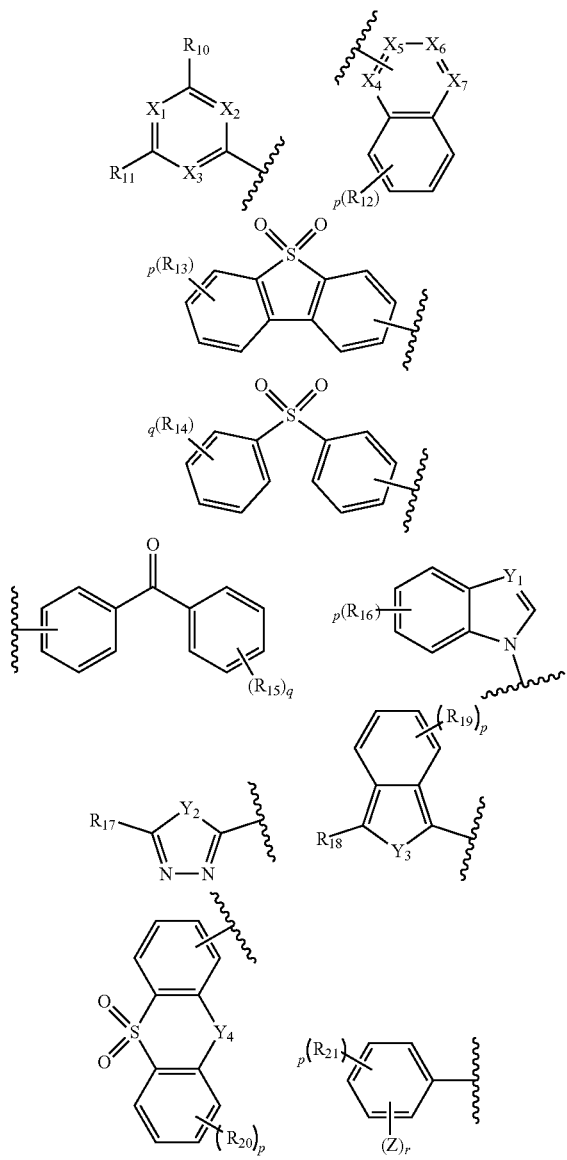

wherein p represents an integer of 0 to 4; q represents an integer of 0 to 5; r represents an integer of 1 to 4; $Y_1$ to $Y_4$ are each independently a divalent bridge selected from the group consisting of O, S, $C(R_{22})(R_{23})$, $NR_{24}$, and $Si(R_{25})(R_{26})$; $X_1$ to $X_7$ independently represent a nitrogen atom or $C(R_s)$, and each $R_s$ represents a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms; Z represents a cyano group or a fluorine atom; and $R_{10}$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. A 5,12-dihydrotetracene derivative of formula (1) or formula (2) below:

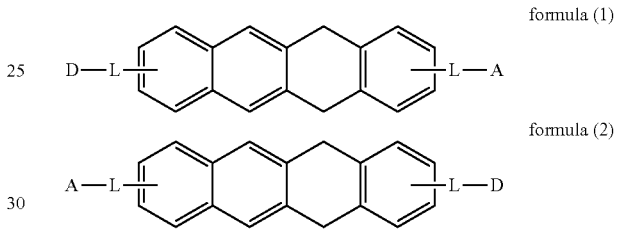

wherein L represents a single bond, a substituted or unsubstituted divalent arylene group having 6 to 30 ring carbon atoms, or a substituted or unsubstituted divalent heteroarylene group having 6 to 30 ring carbon atoms; D is an electron donor moiety selected from the group consisting of a substituted or unsubstituted carbazolyl group, a substituted or unsubstituted biscarbazolyl group, a substituted or unsubstituted dihydroacridine group, a substituted or unsubstituted phenoxazine group, and a substituted or unsubstituted diarylamine group; and A is an electron acceptor moiety selected from the following formulas:

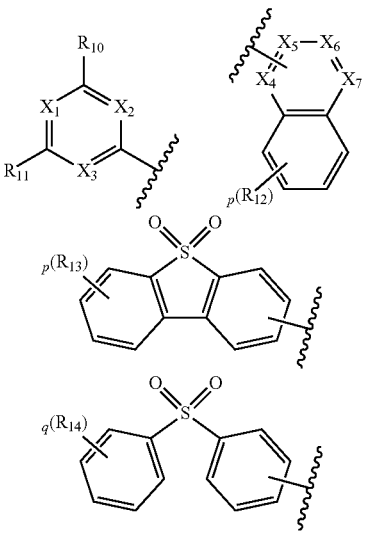

-continued

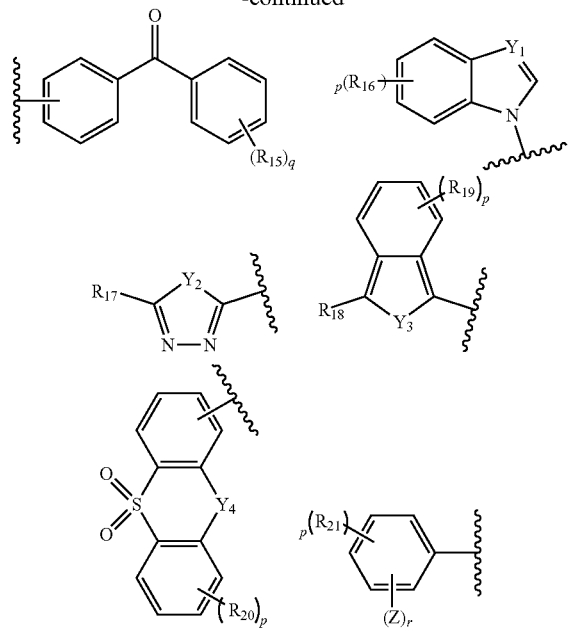

wherein p represents an integer of 0 to 4; q represents an integer of 0 to 5; r represents an integer of 1 to 4; $Y_1$ to $Y_4$ are each independently a divalent bridge selected from the group consisting of O, S, $C(R_{22})(R_{23})$, $NR_{24}$, and $Si(R_{25})(R_{26})$; $X_1$ to $X_7$ independently represent a nitrogen atom or $C(R_s)$, and each $R_s$ represents a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms; Z represents a cyano group or a fluorine atom; and $R_{10}$ to $R_{26}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

2. The 5,12-dihydrotetracene derivative according to claim 1, wherein the 5,12-dihydrotetracene derivative is one of the following compounds:

Compound 1

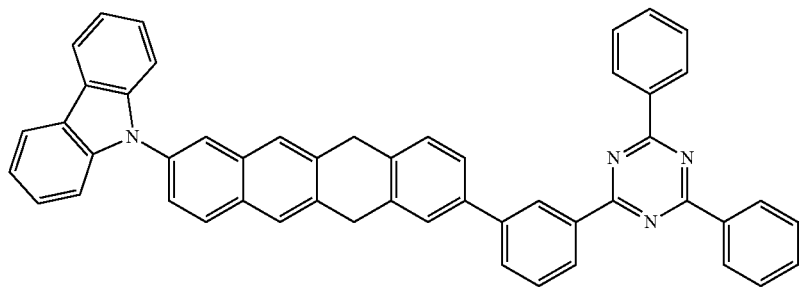

Compound 2

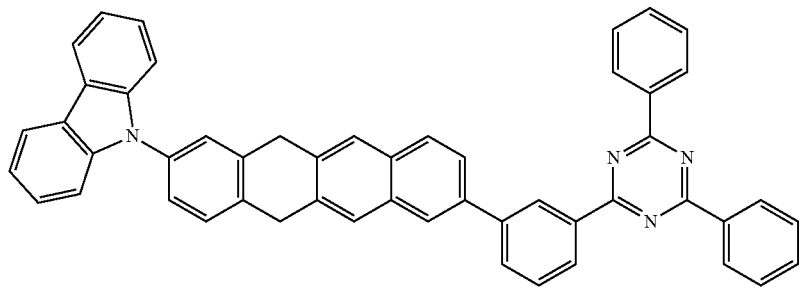

Compound 3
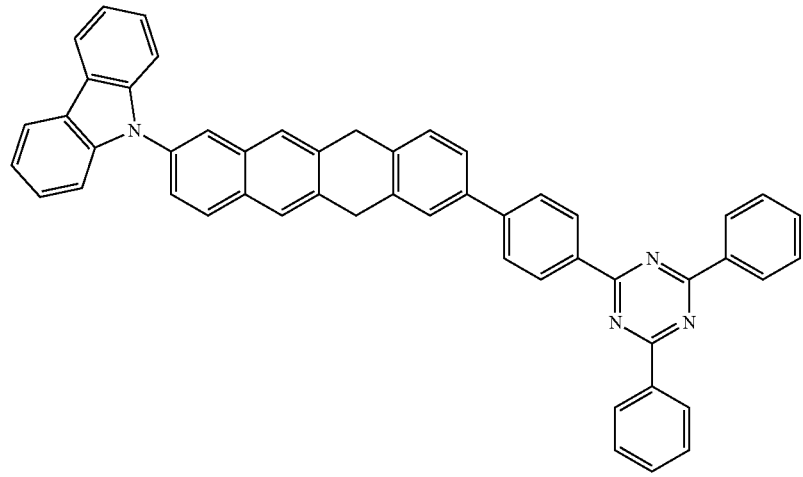
Compound 4
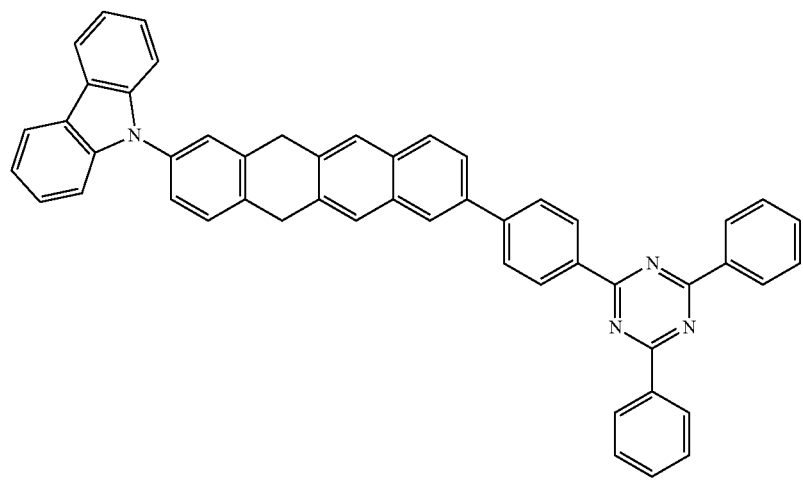
Compound 5
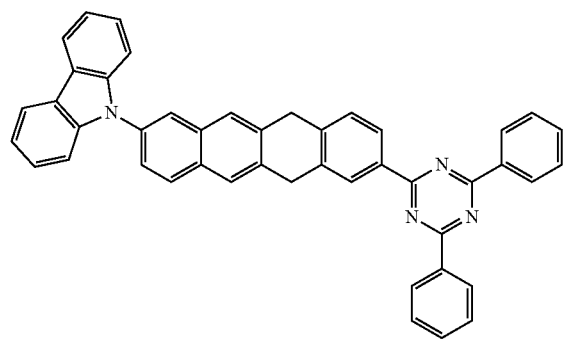
Compound 6
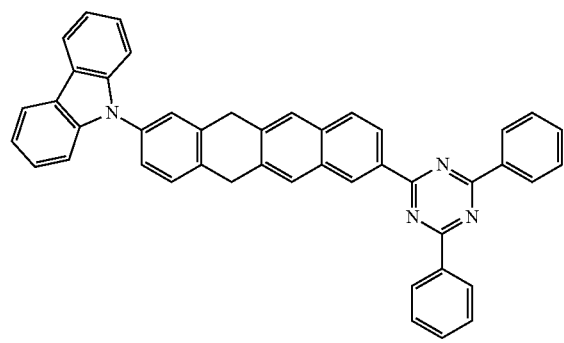

-continued
Compound 7
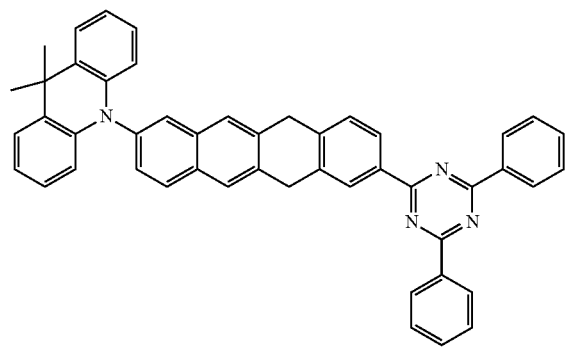
Compound 8
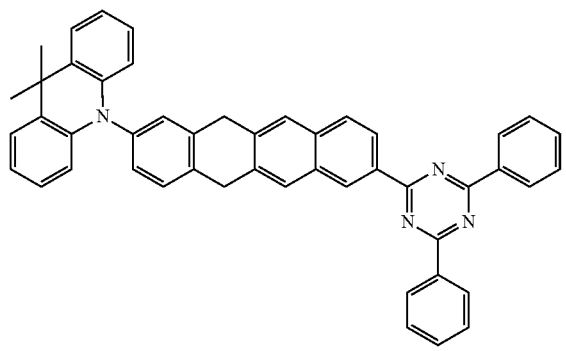
Compound 9
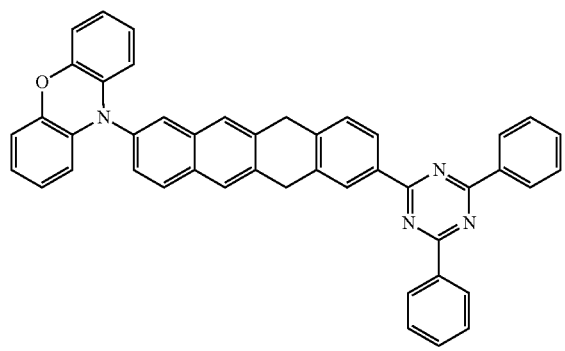
Compound 10
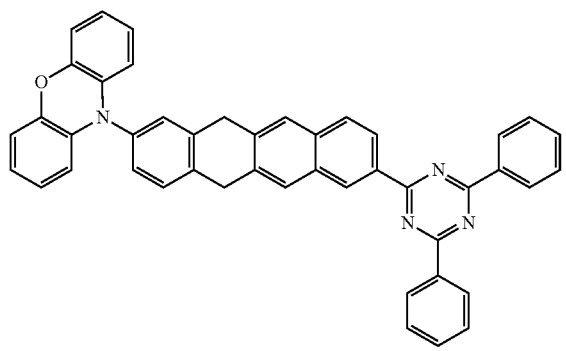
Compound 11
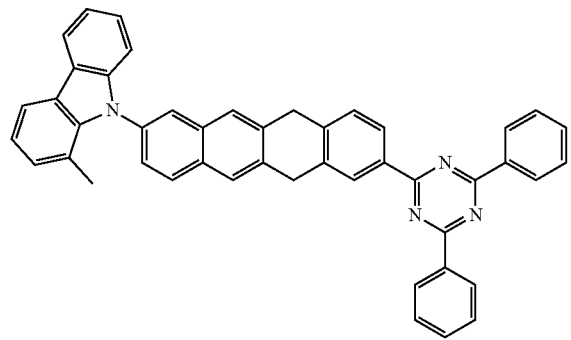
Compound 12
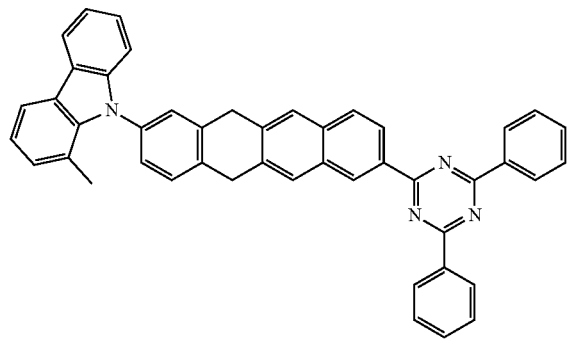
Compound 13
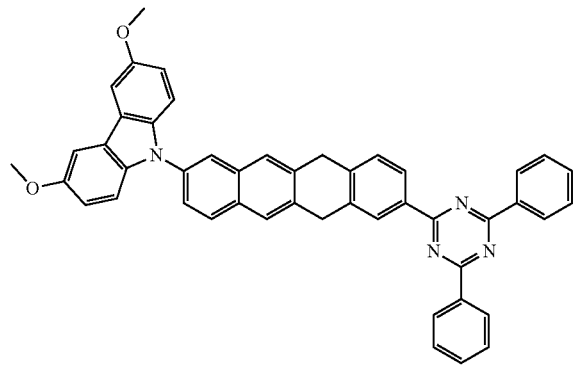
Compound 14
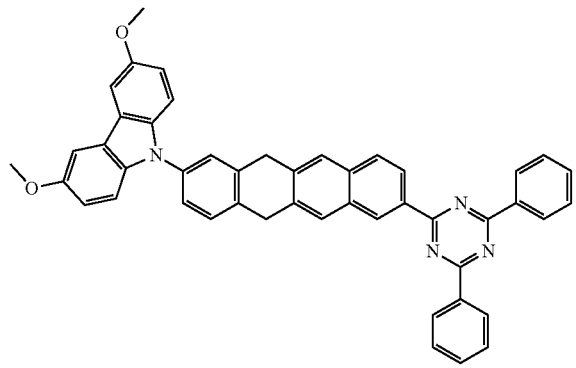

-continued
Compound 15
Compound 16
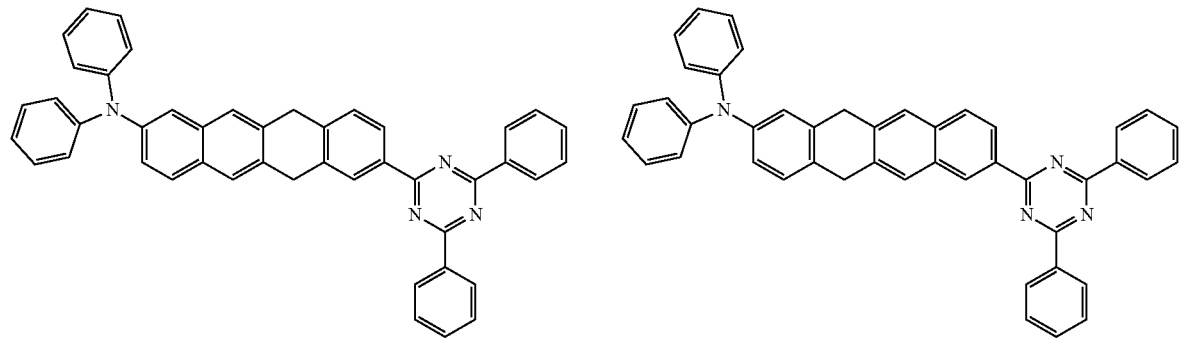
Compound 17
Compound 18
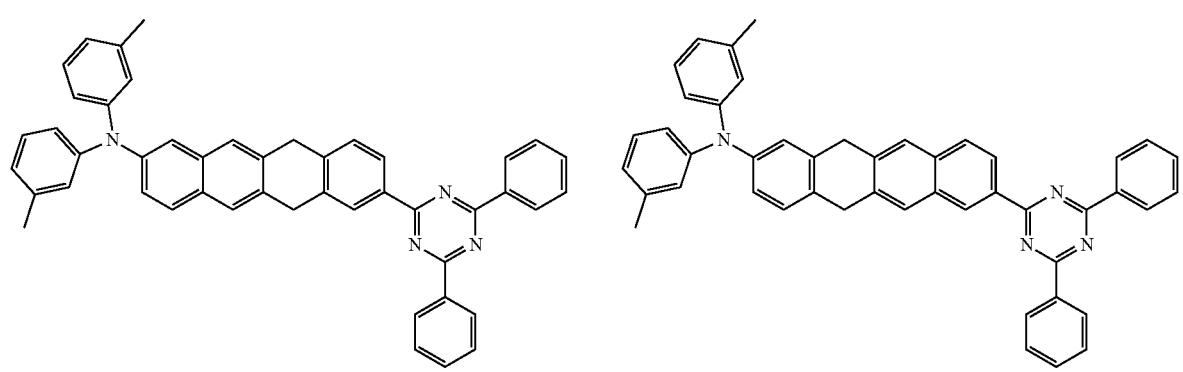
Compound 19
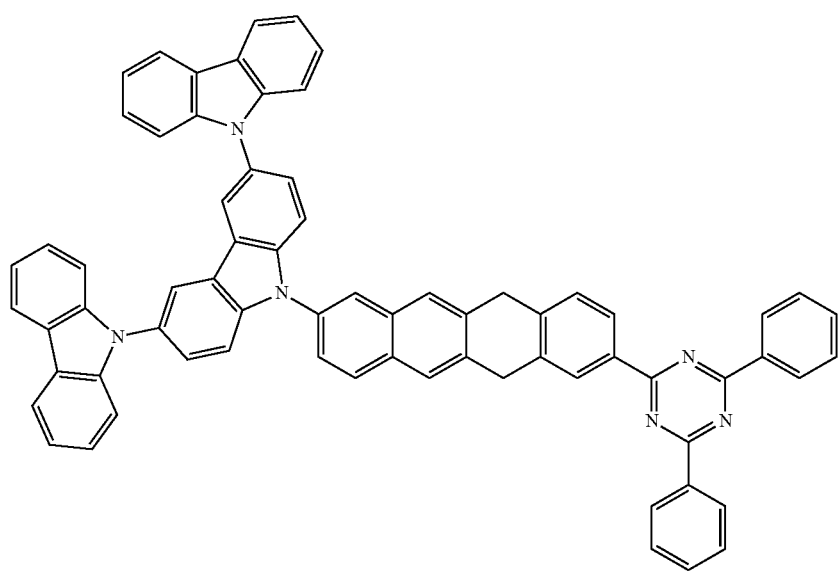

-continued
Compound 20
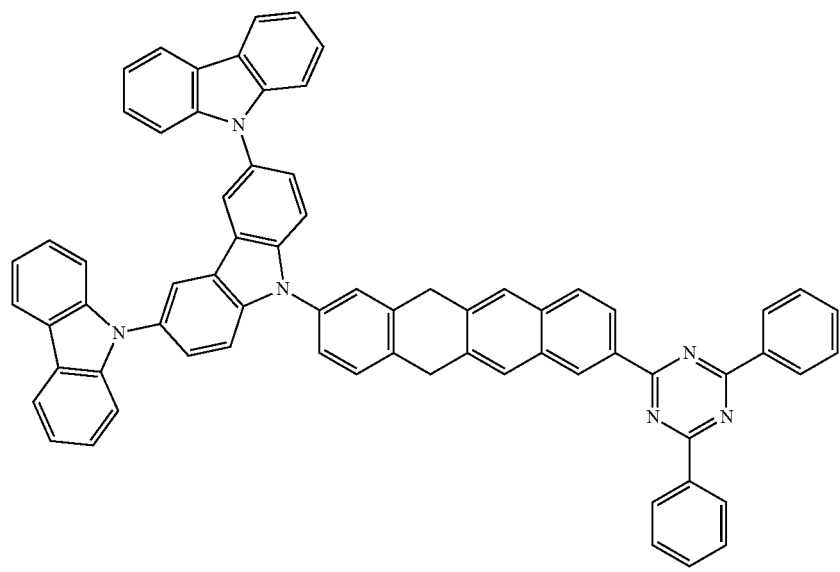
Compound 21
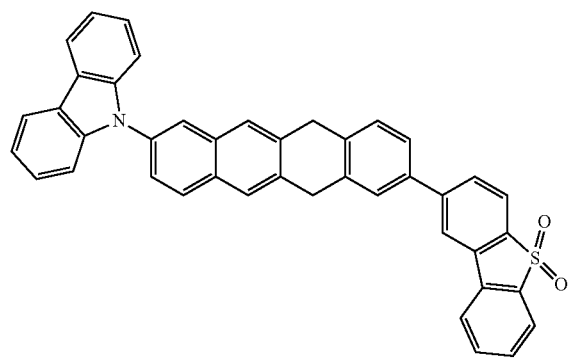
Compound 22
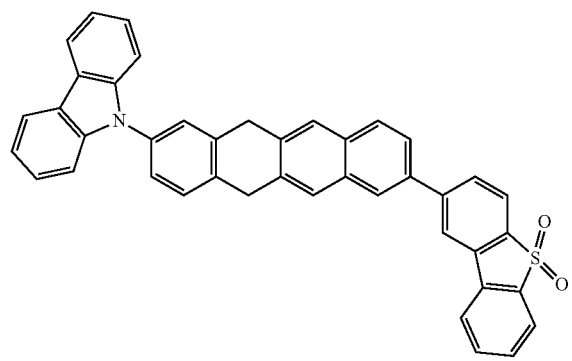
Compound 23
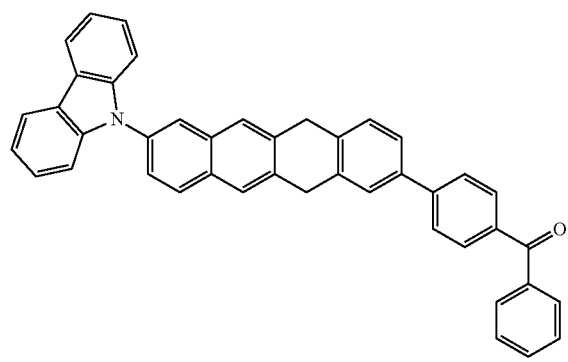
Compound 24
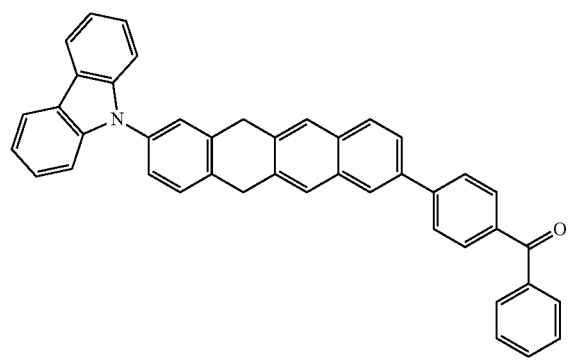

-continued
Compound 25
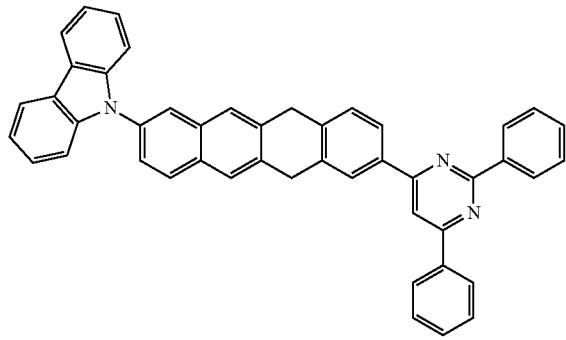
Compound 26
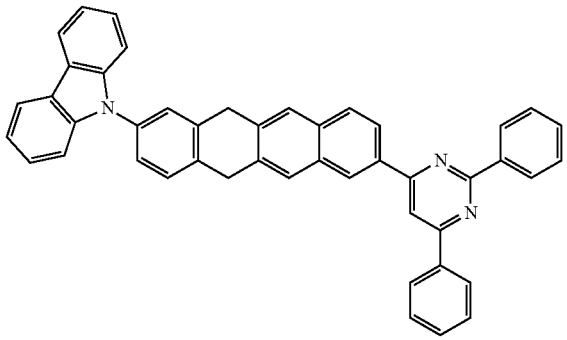
Compound 27
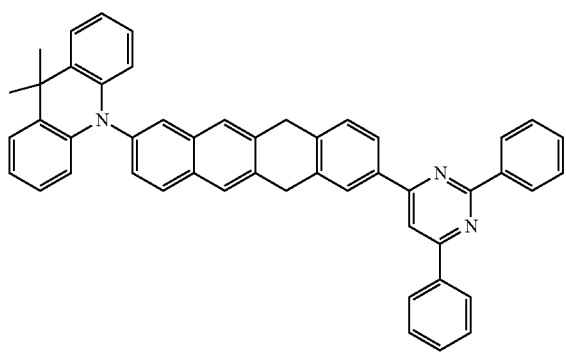
Compound 28
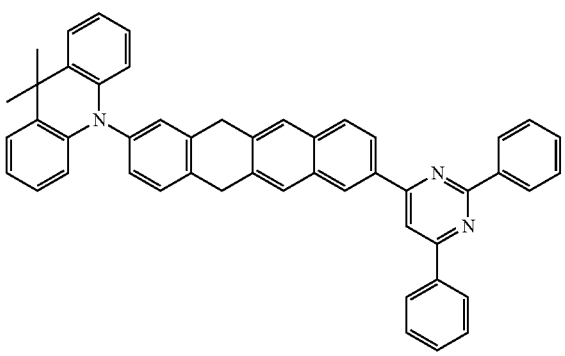
Compound 29
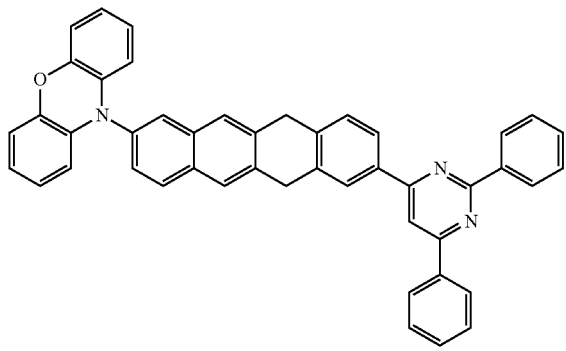
Compound 30
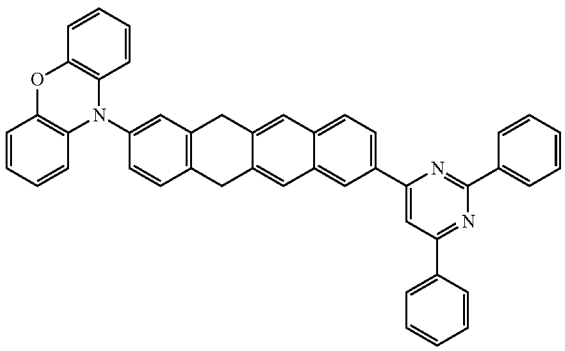
Compound 31
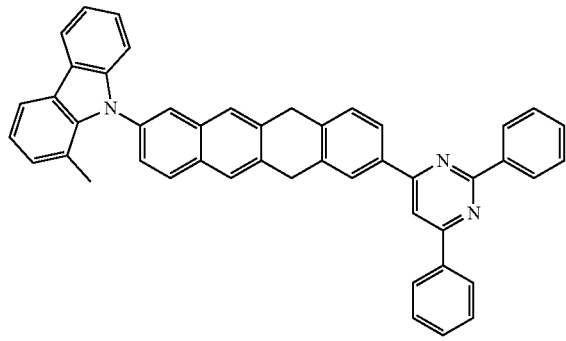
Compound 32
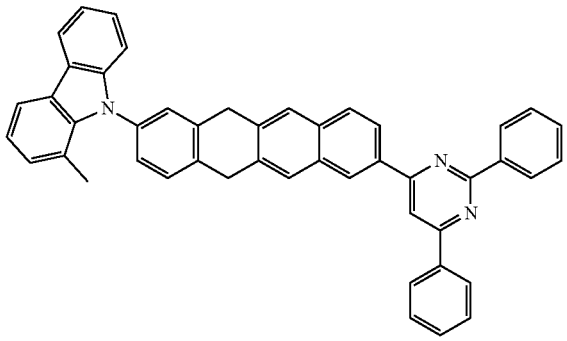

Compound 33
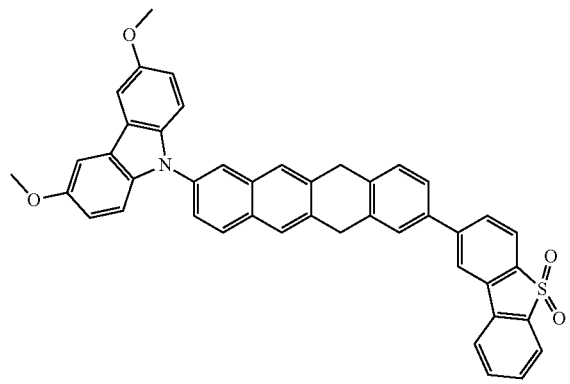
Compound 34
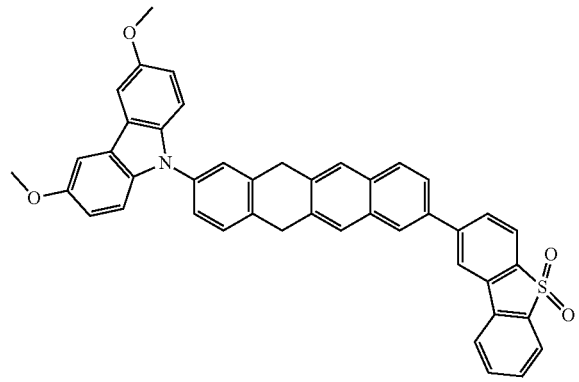
Compound 35
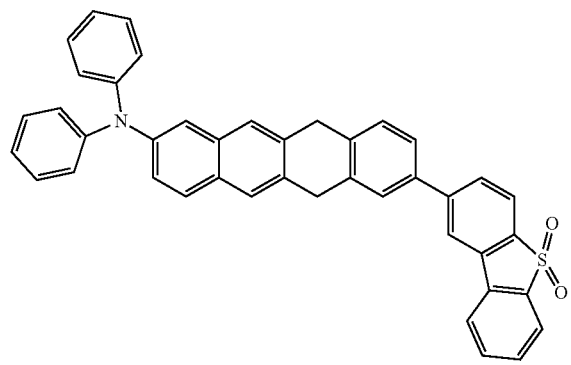
Compound 36
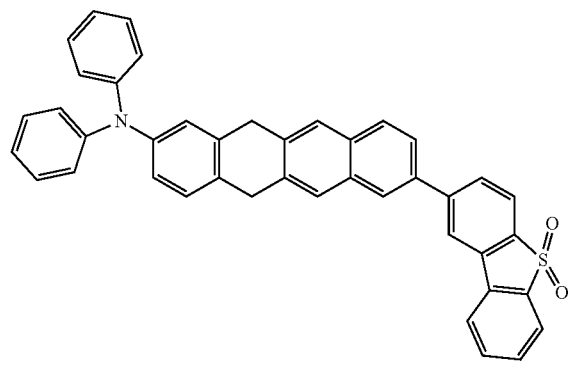
Compound 37
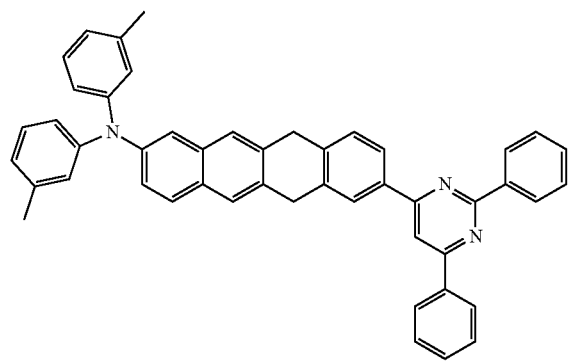
Compound 38
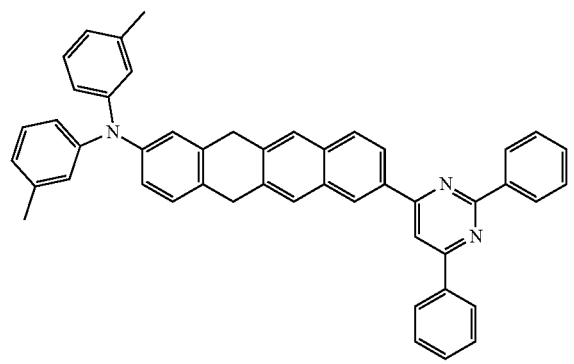

-continued
Compound 39
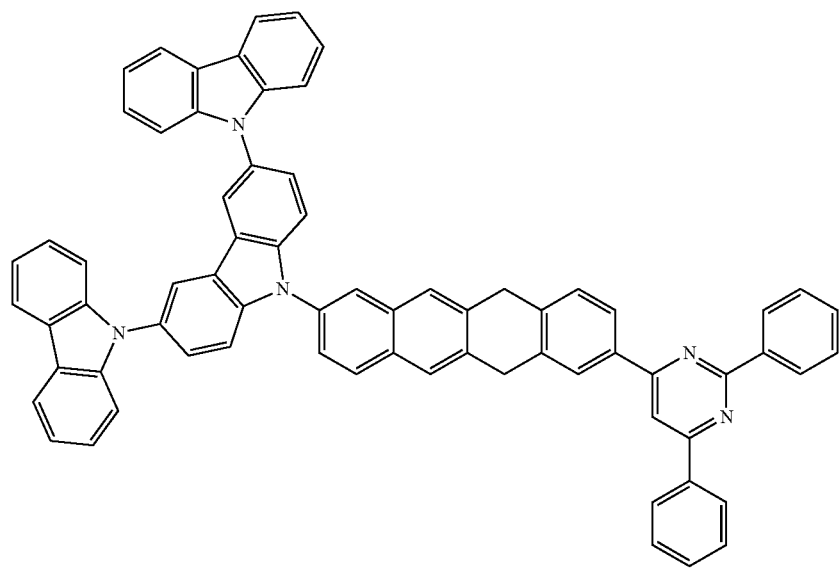
Compound 40
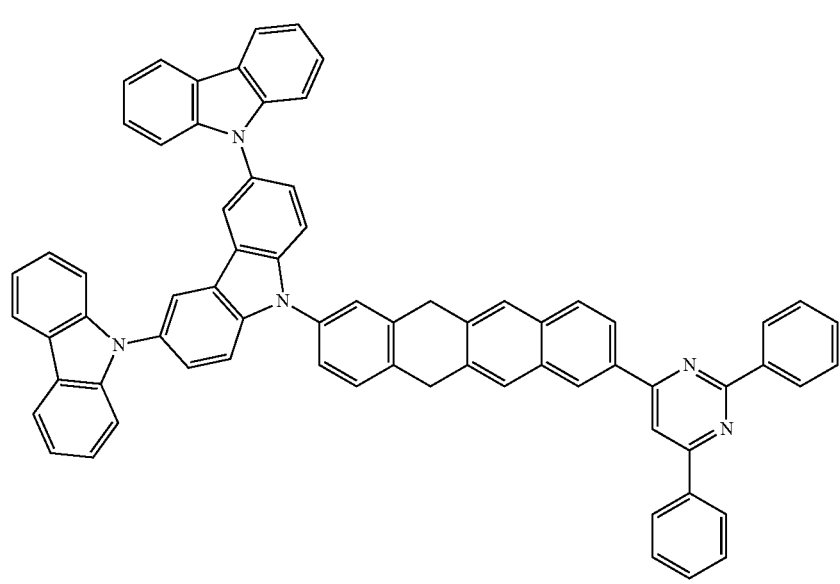
Compound 41
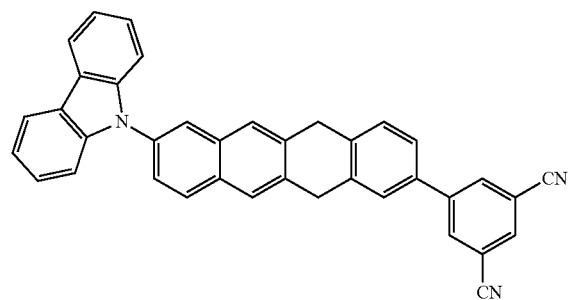
Compound 42
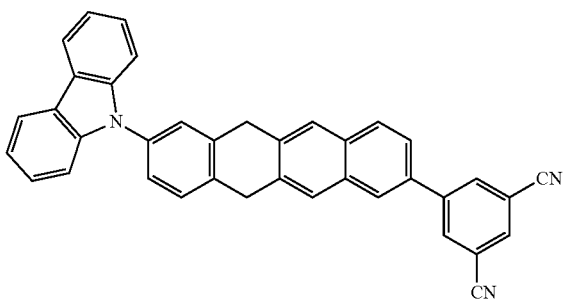

-continued
Compound 43
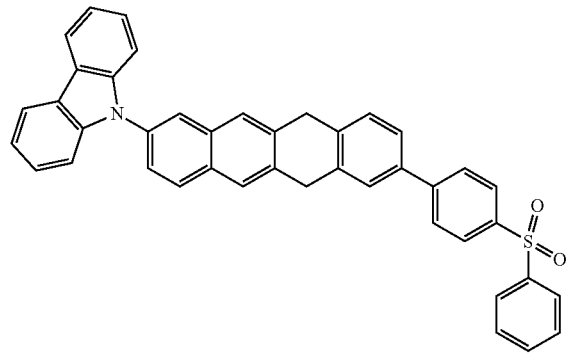
Compound 44
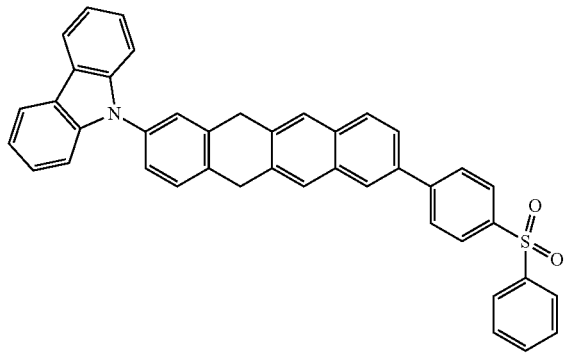
Compound 45
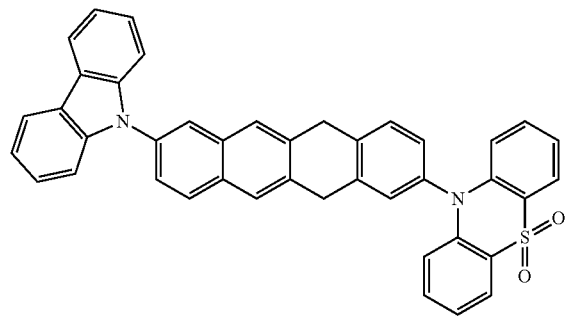
Compound 46
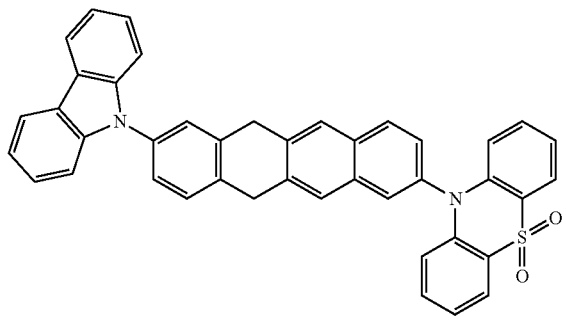
Compound 47
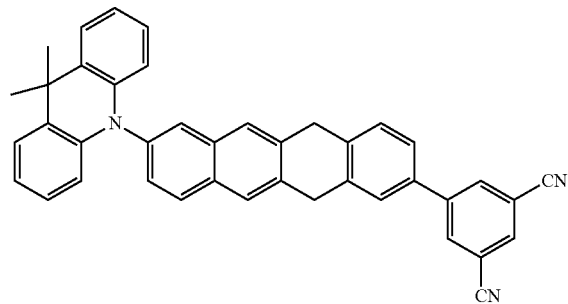
Compound 48
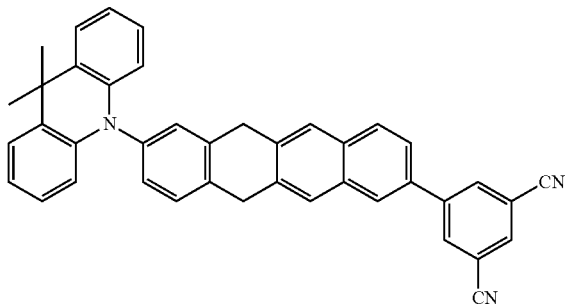
Compound 49
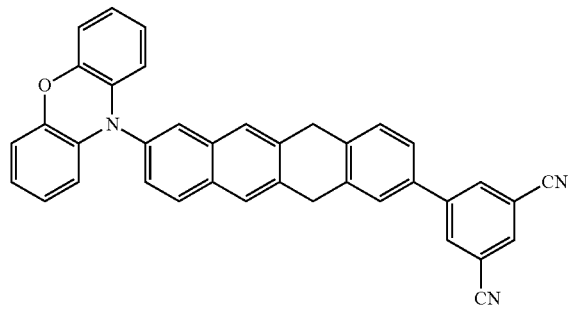
Compound 50
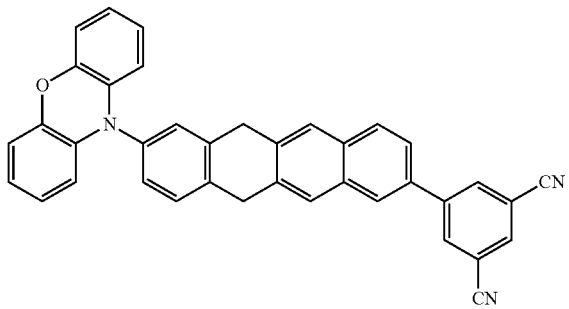

-continued
Compound 51
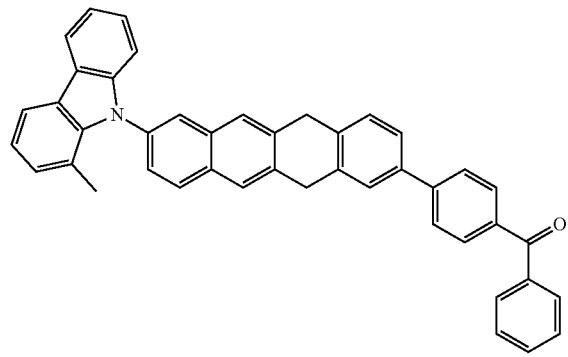
Compound 52
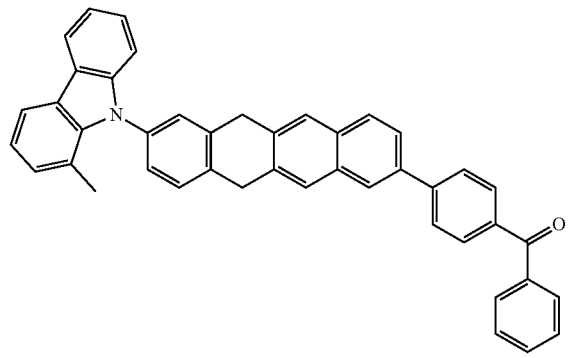
Compound 53
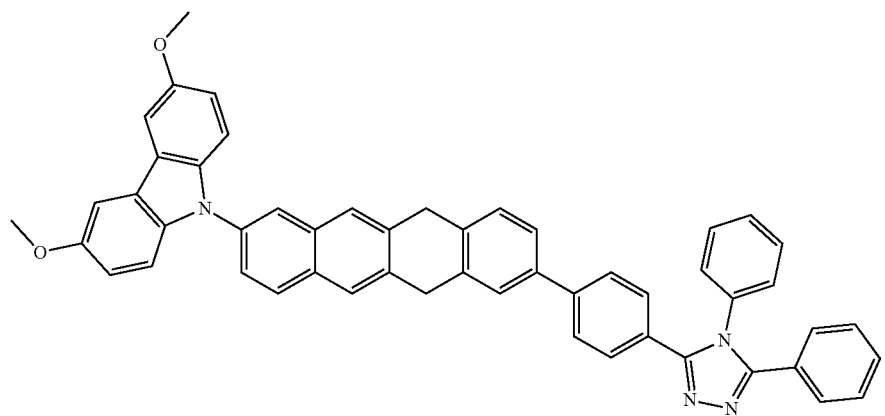
Compound 54
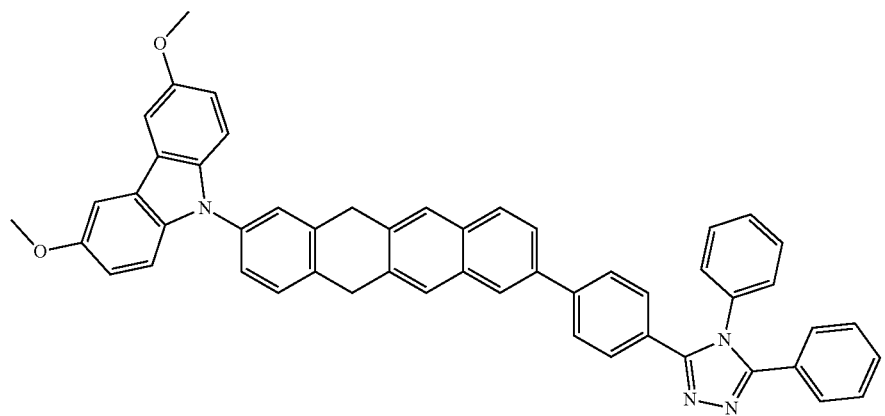
Compound 55
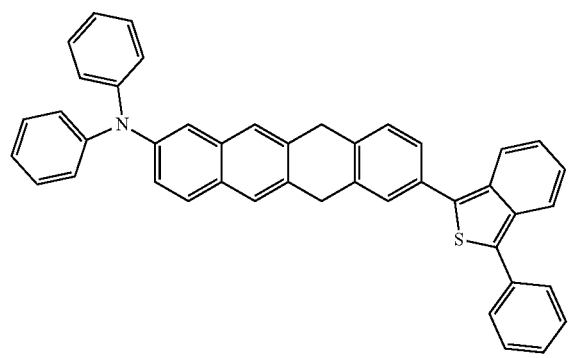
Compound 56
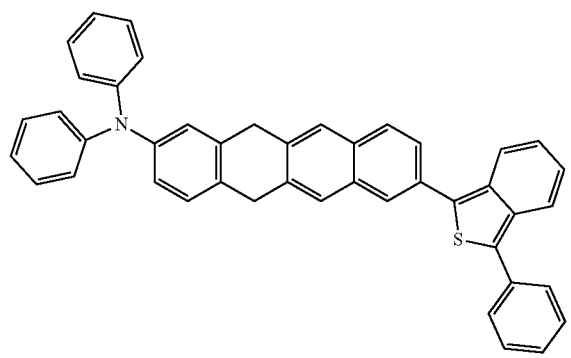

-continued
Compound 57
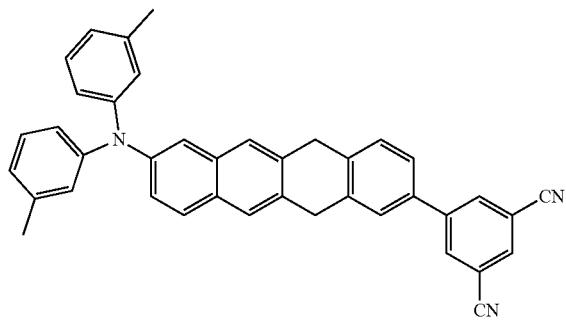
Compound 58
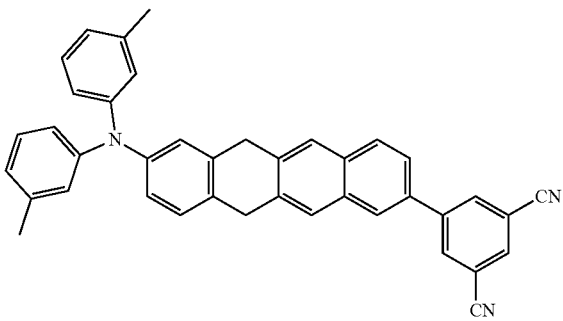
Compound 59
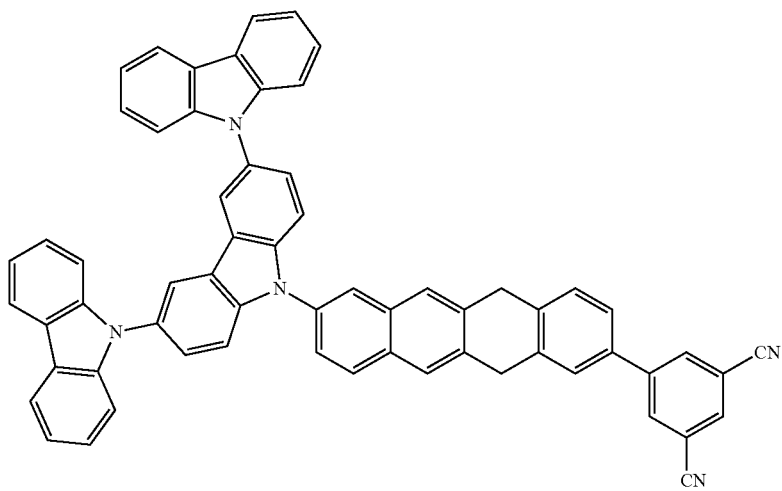
Compound 60
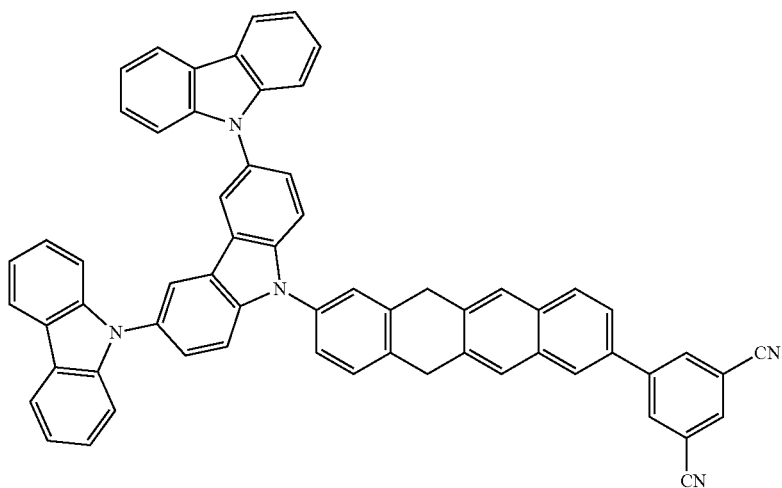

Compound 61
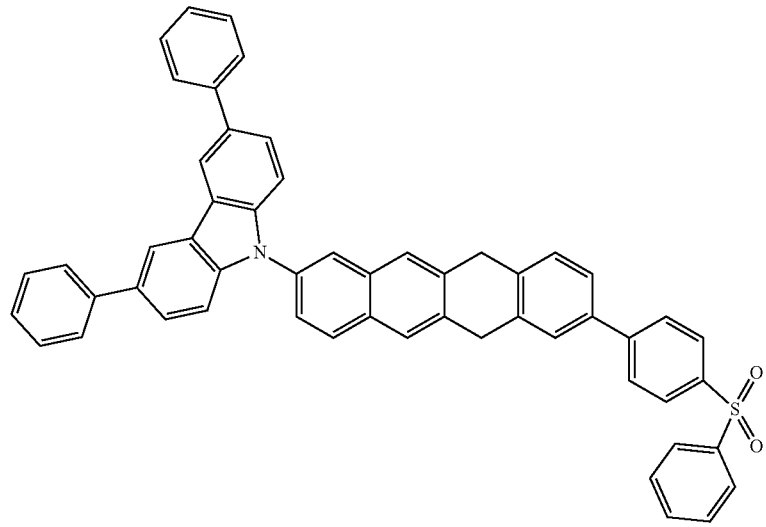
Compound 62
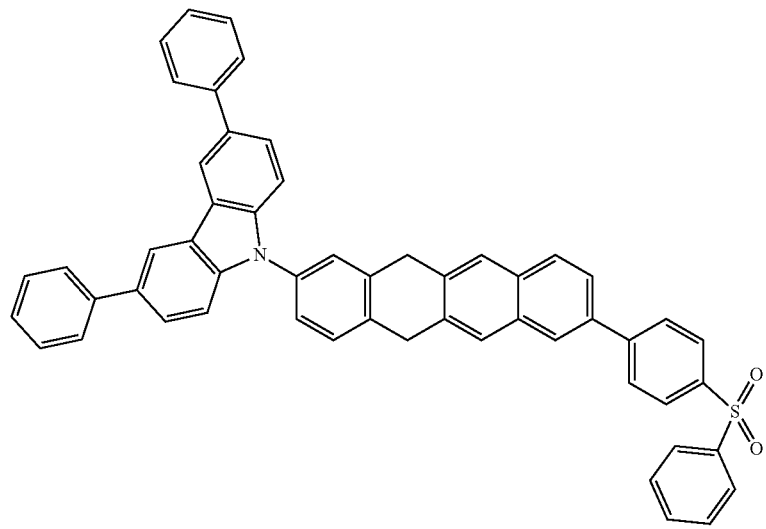
Compound 63
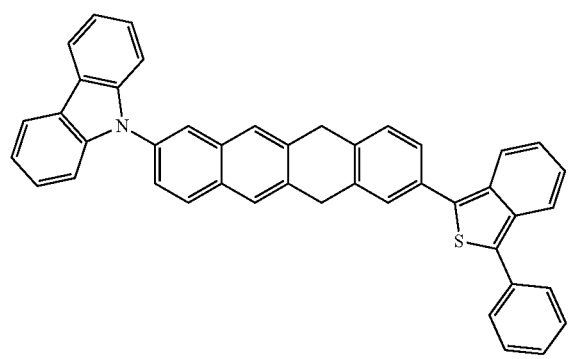
Compound 64
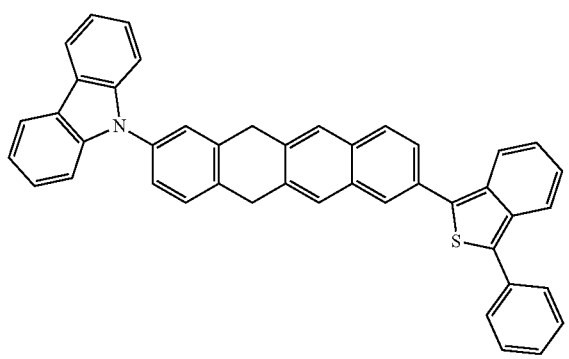

-continued
Compound 65
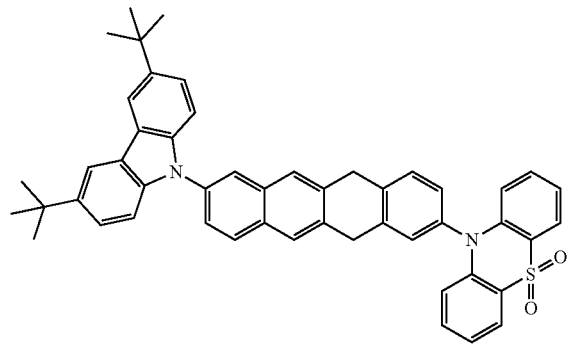
Compound 66
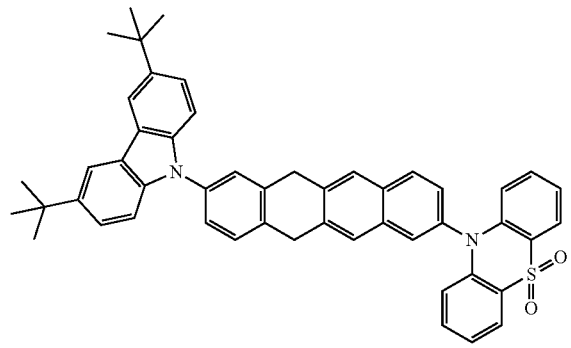
Compound 67
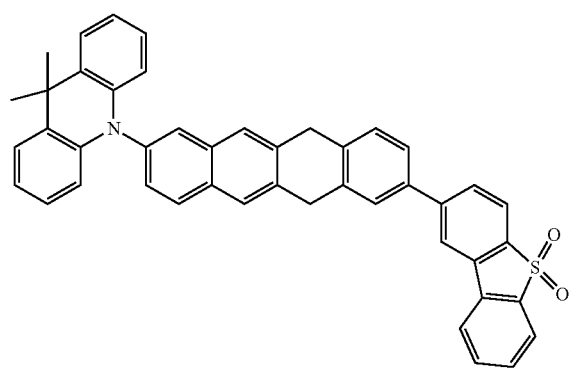
Compound 68
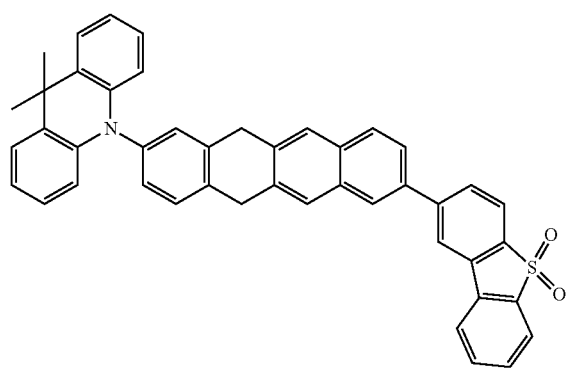
Compound 69
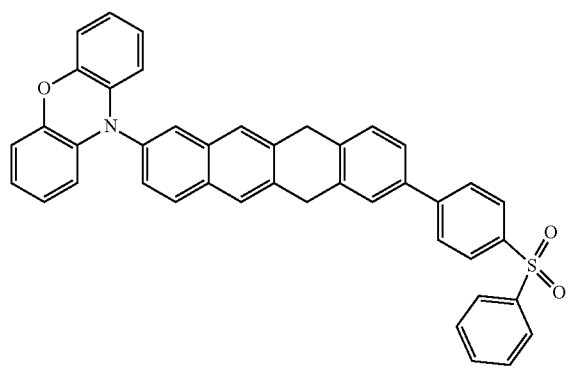
Compound 70
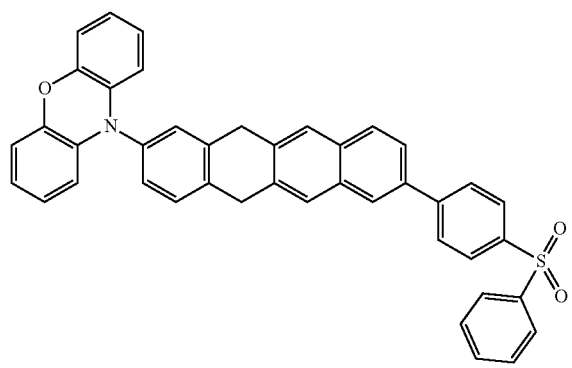
Compound 71
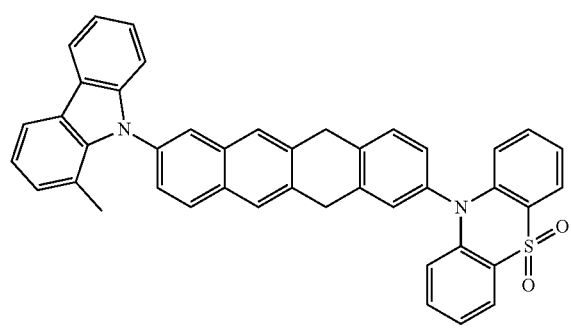
Compound 72
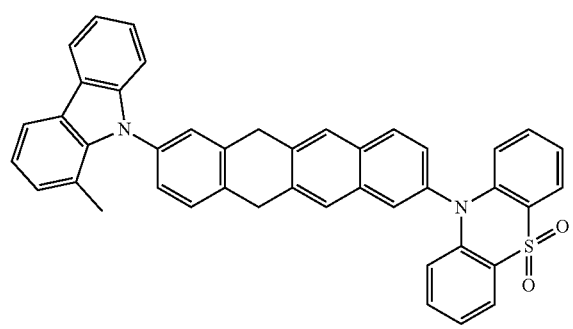

-continued
Compound 73
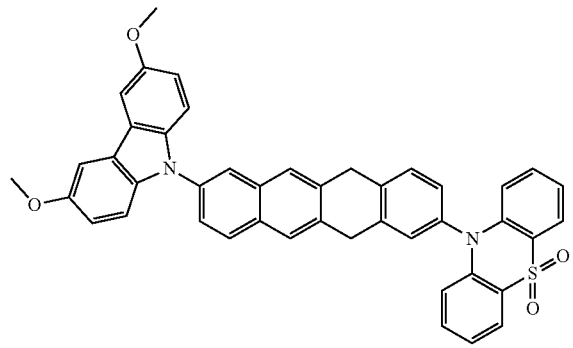
Compound 75
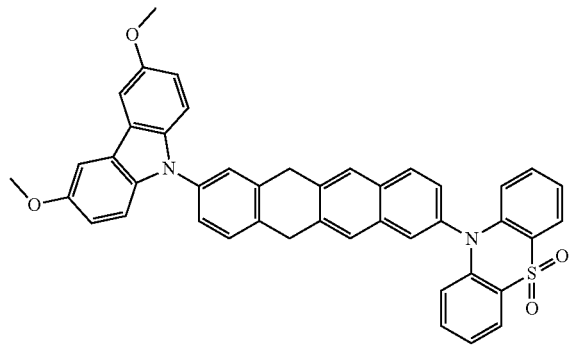
Compound 76
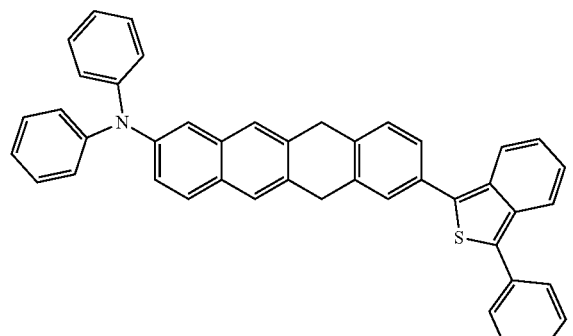
Compound 77
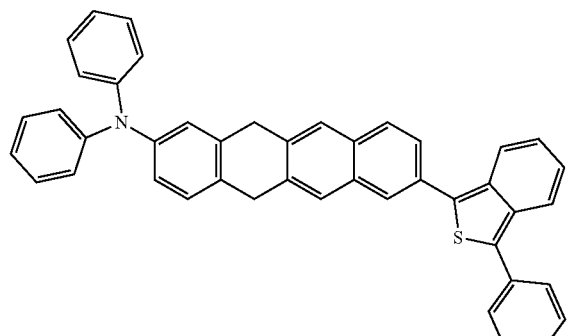
Compound 78
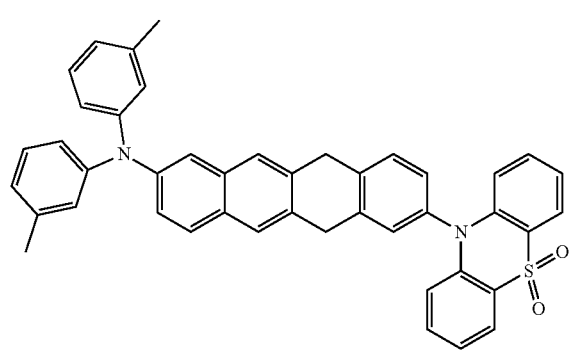
Compound 79
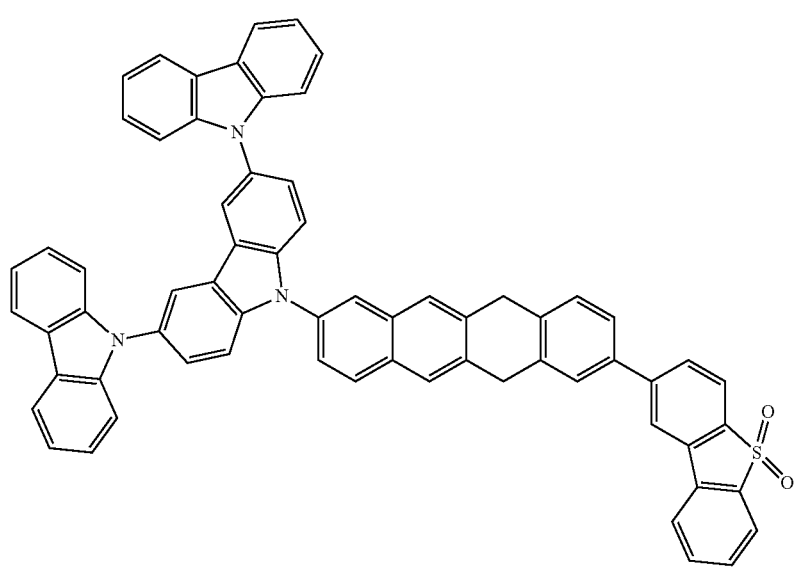

-continued
Compound 80
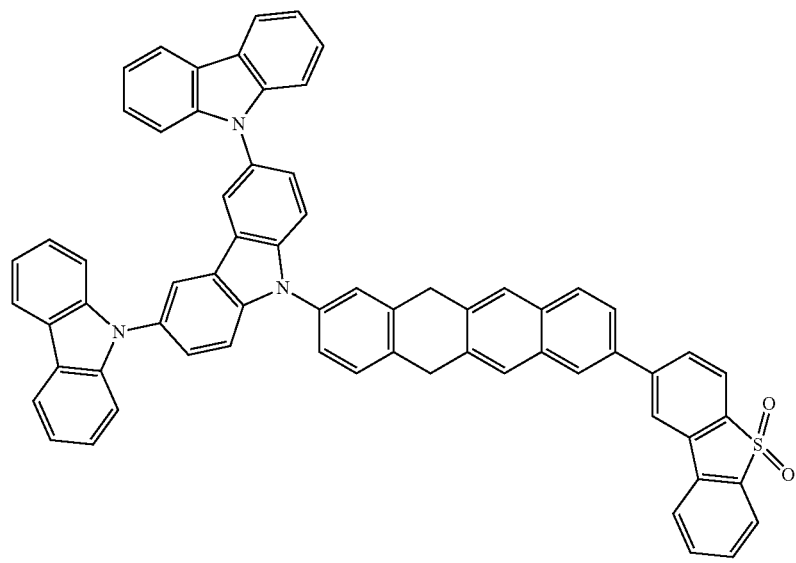
Compound 81
Compound 82
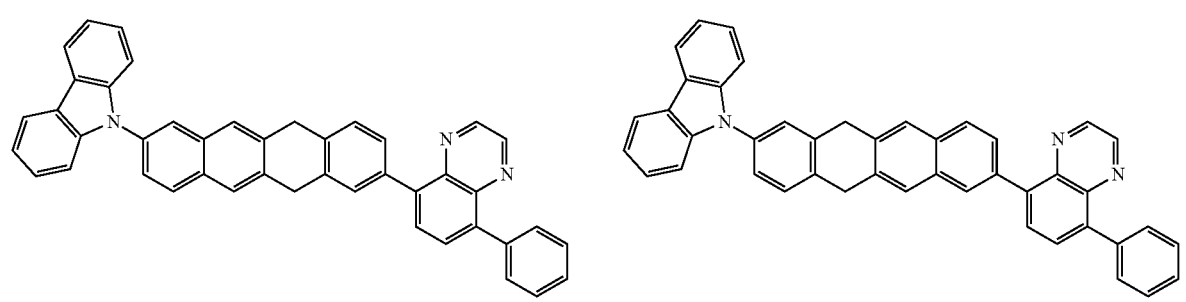
Compound 83
Compound 84
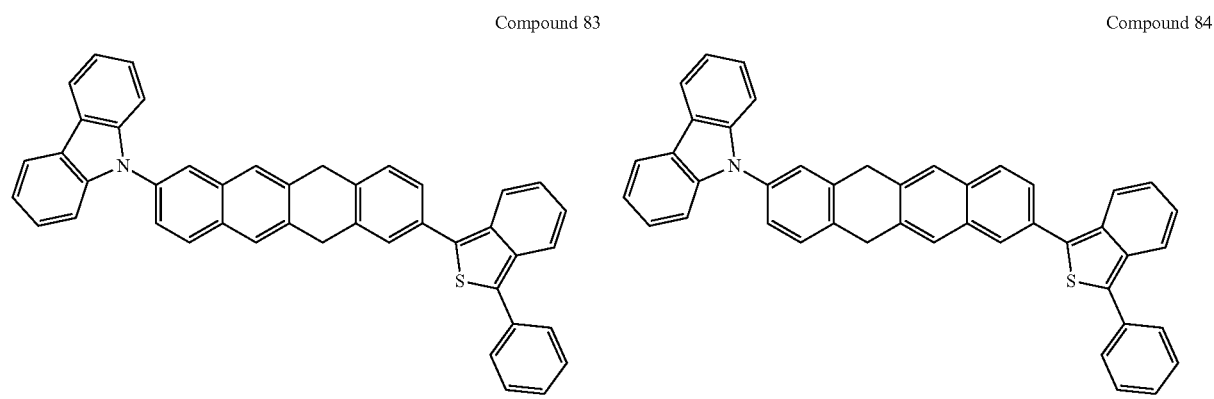
Compound 85
Compound 86
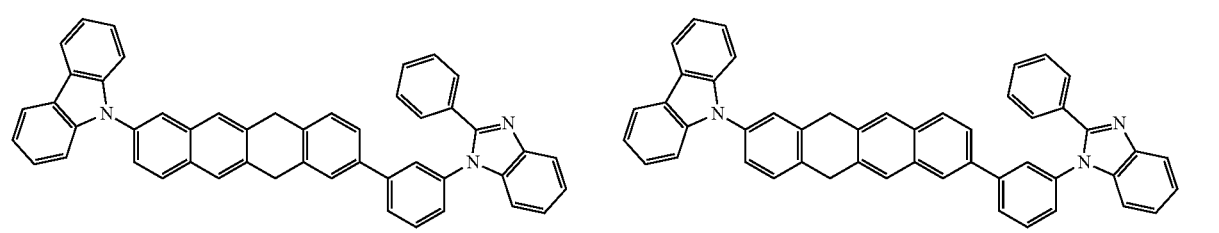

Compound 87
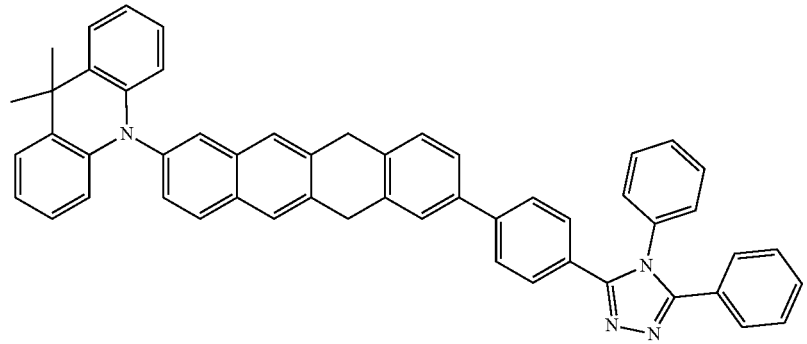
Compound 88
Compound 89
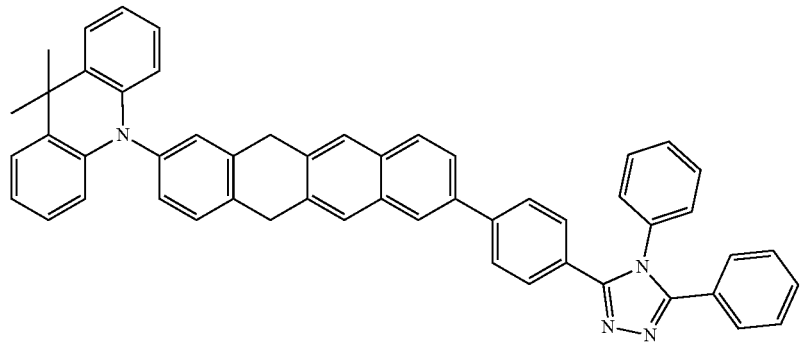
Compound 90
Compound 89
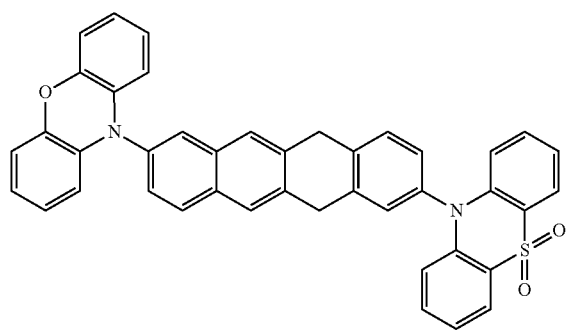
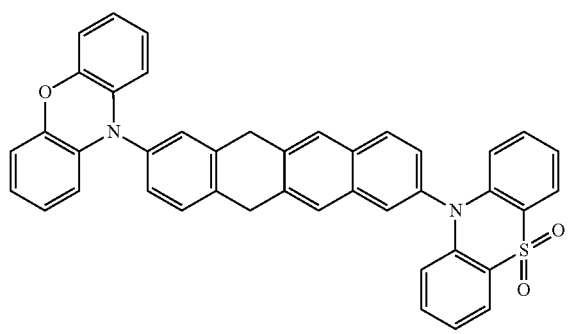
Compound 91
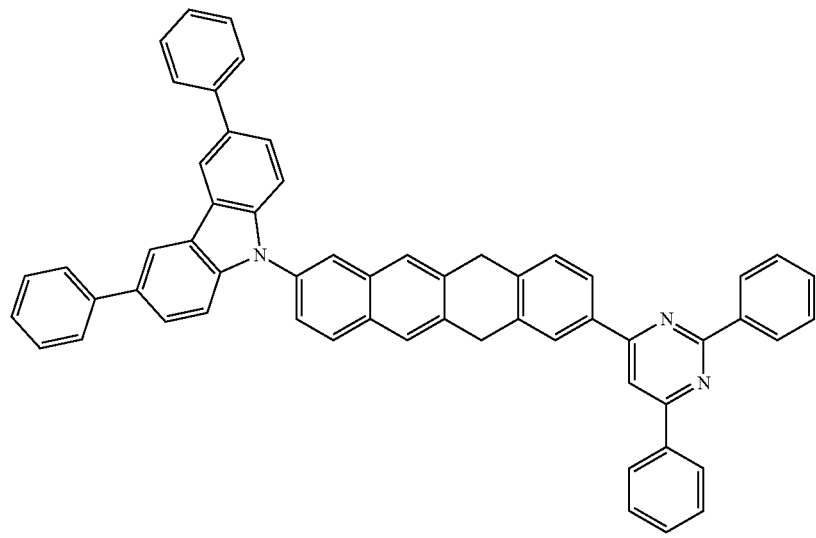

-continued
Compound 92
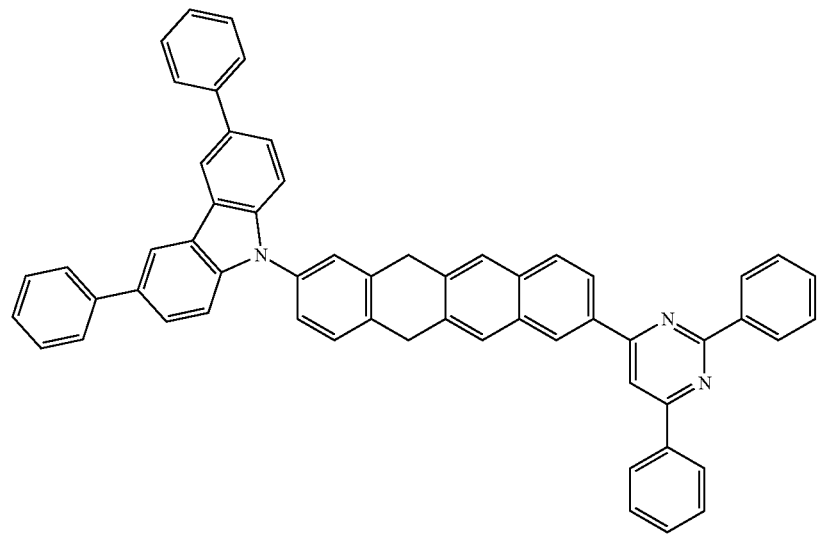
Compound 93
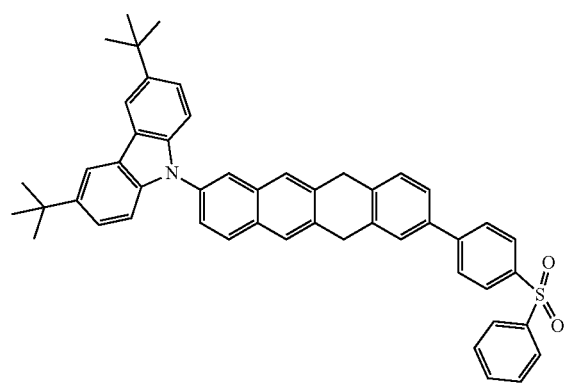
Compound 94
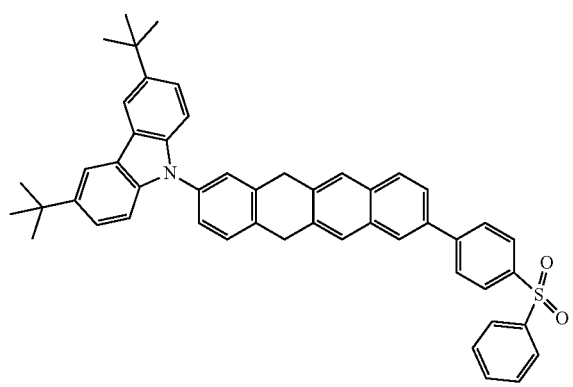
Compound 95
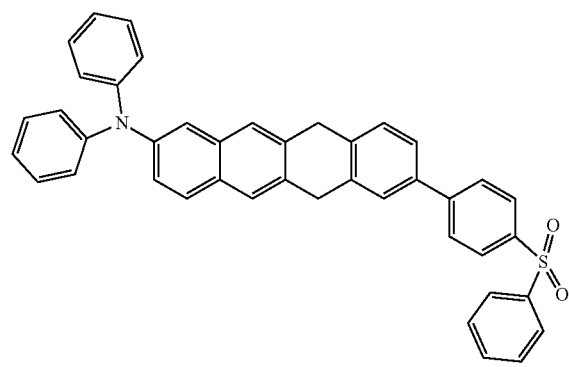
Compound 96
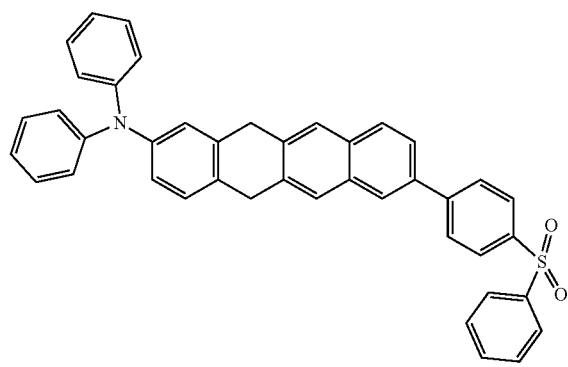

Compound 97
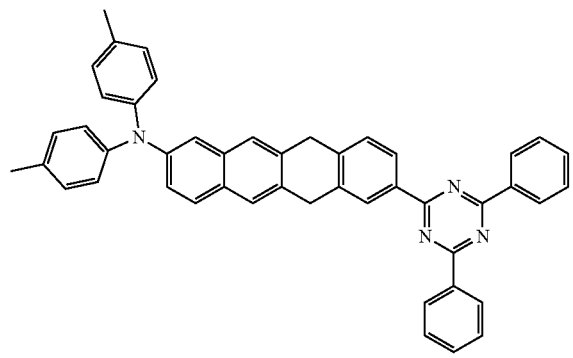
Compound 98
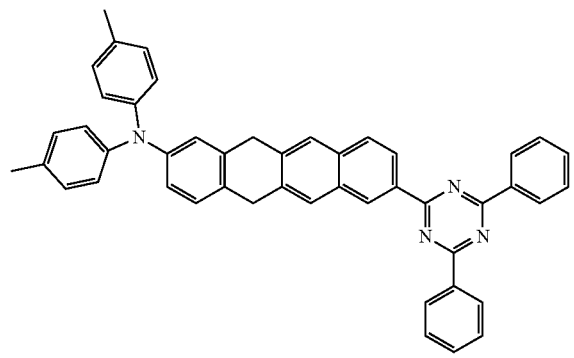
Compound 99
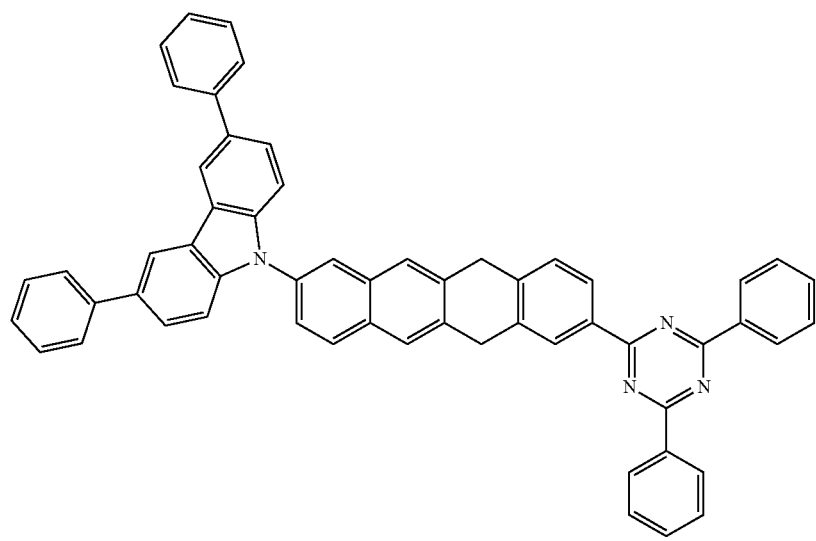
Compound 100
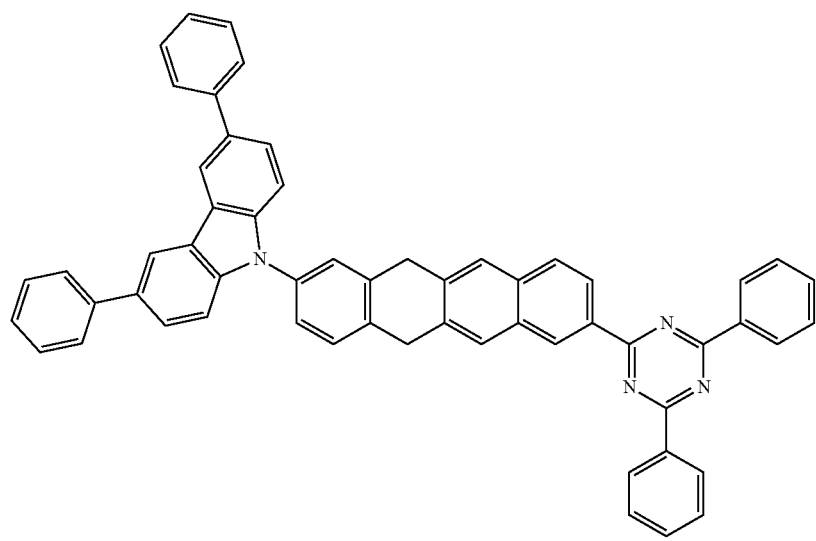

-continued
Compound 101
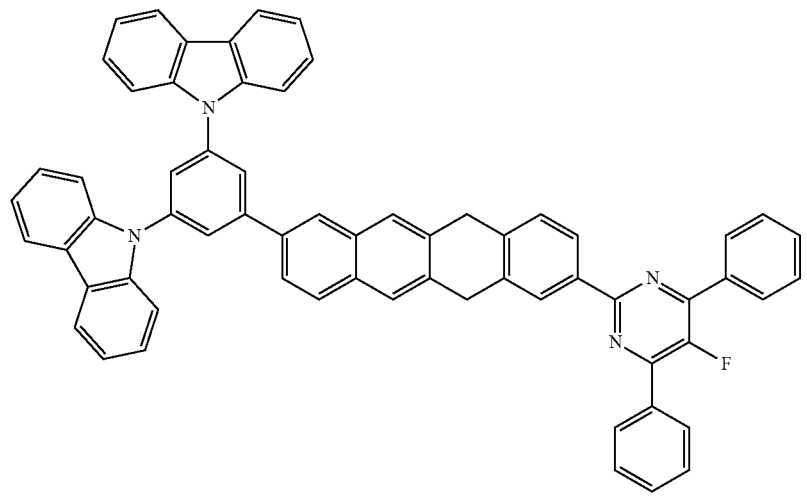
Compound 102
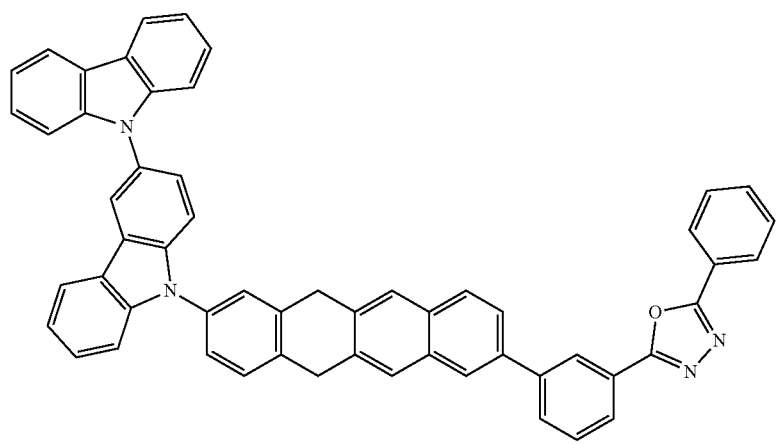
Compound 103
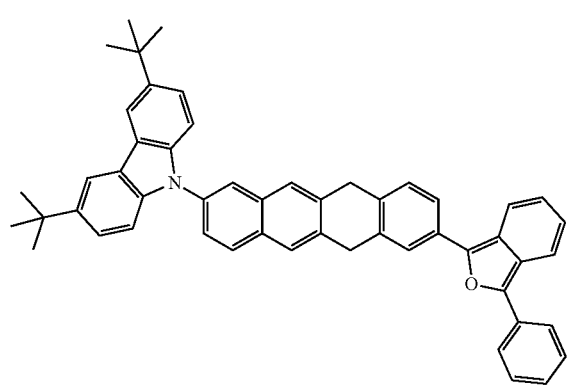
Compound 104
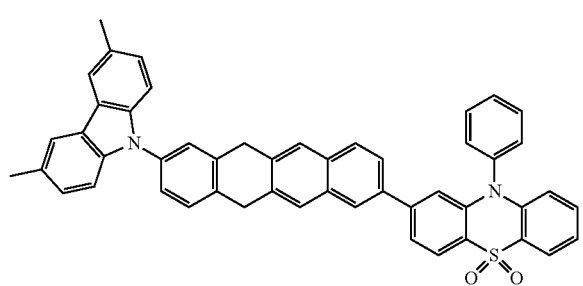

-continued
Compound 105
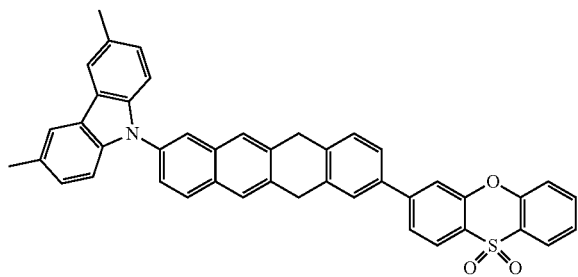
Compound 106
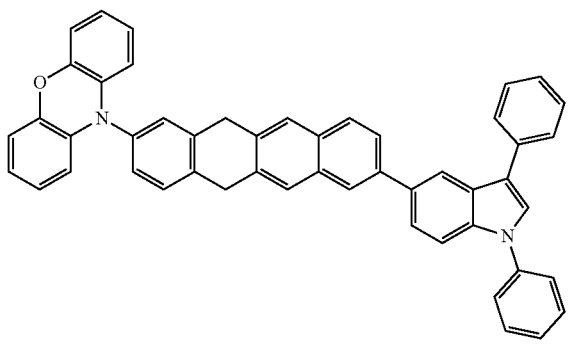
Compound 107
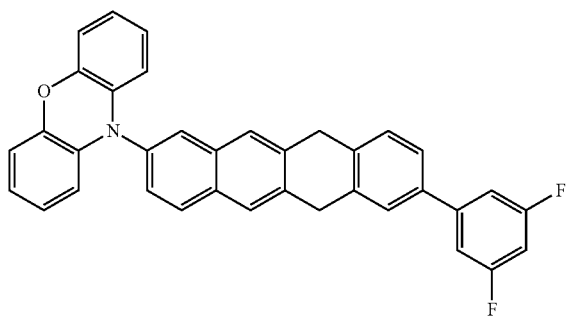
Compound 108
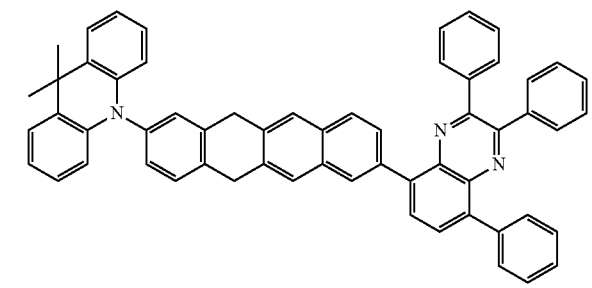
Compound 109
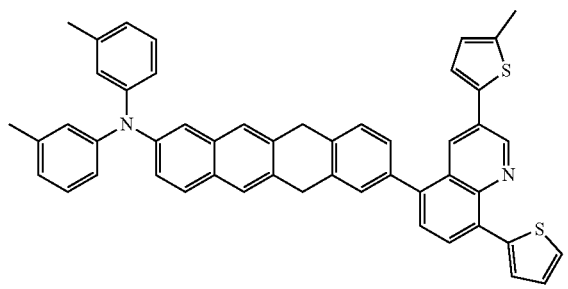
Compound 110
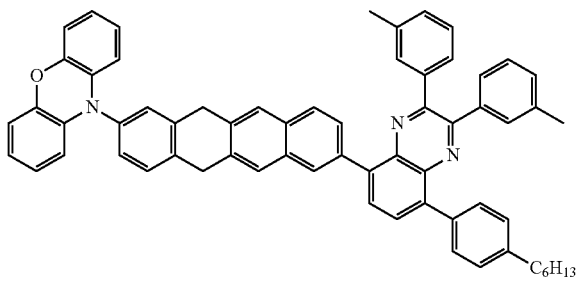
Compound 111
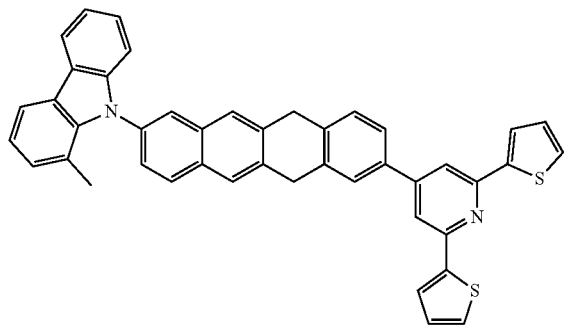
Compound 112
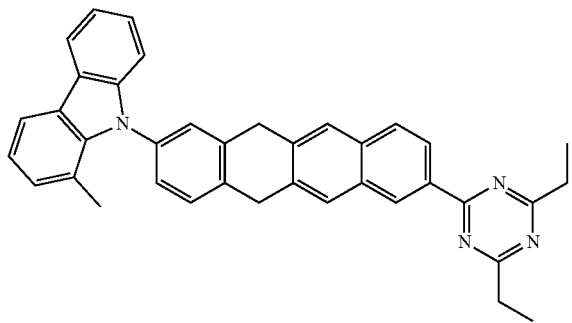

Compound 113
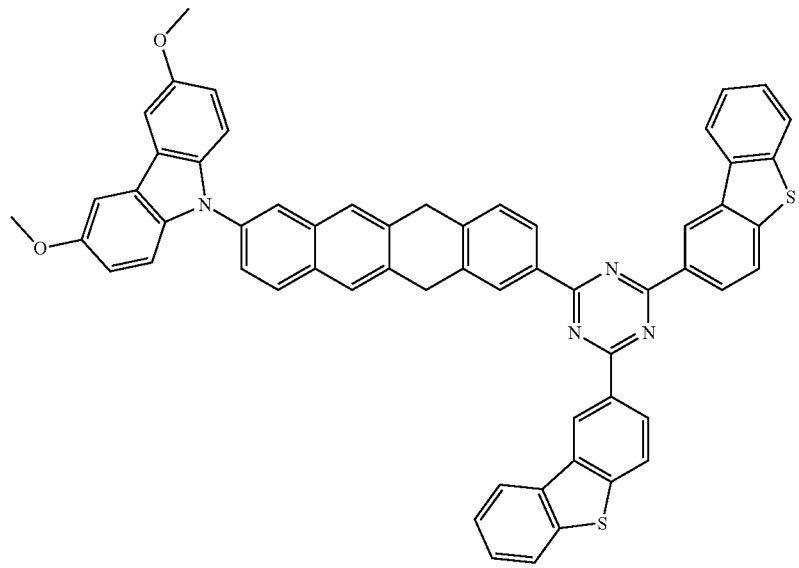
Compound 114
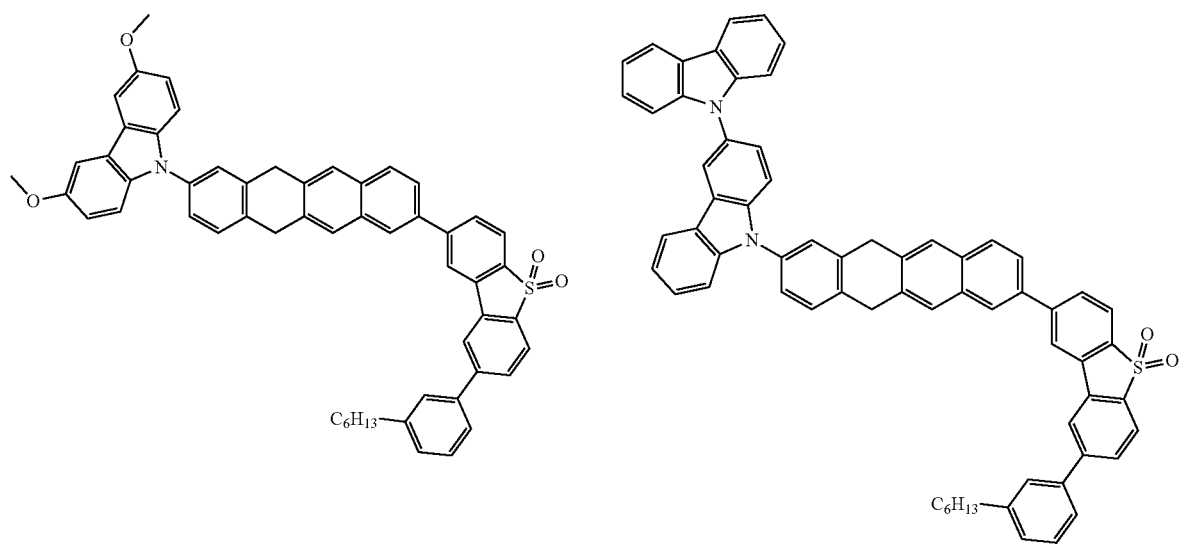
Compound 115
Compound 116
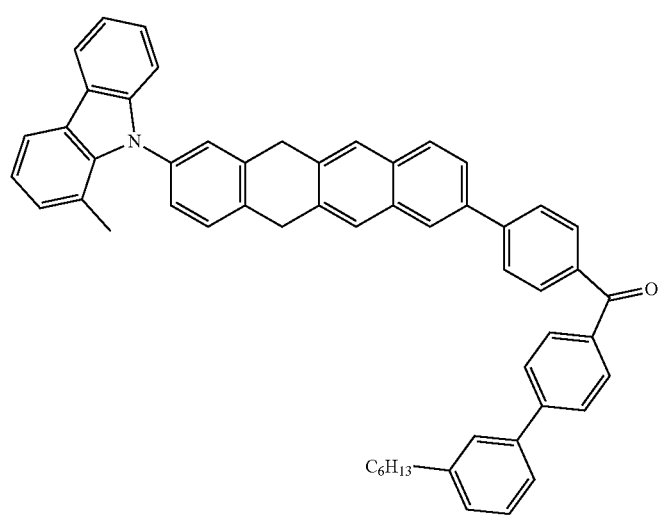

Compound 117
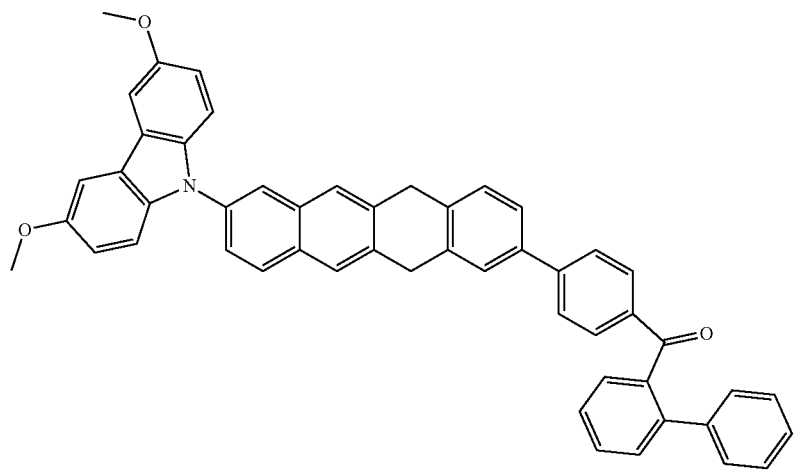
Compound 118
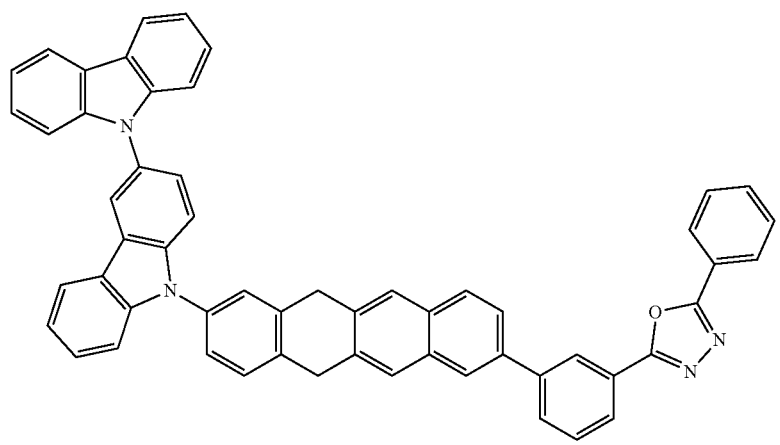
Compound 119
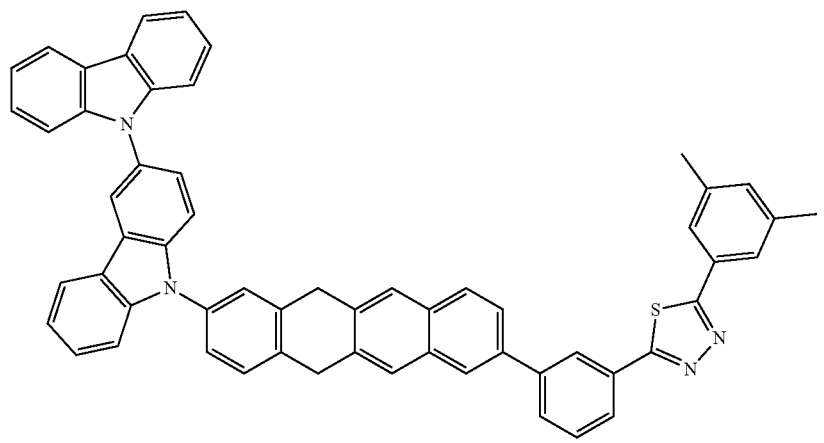

-continued
Compound 120
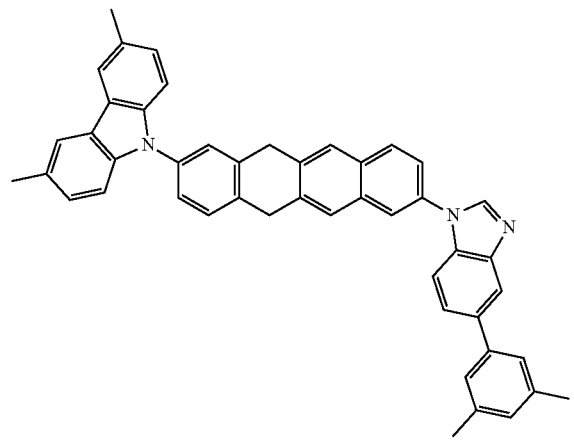
Compound 121
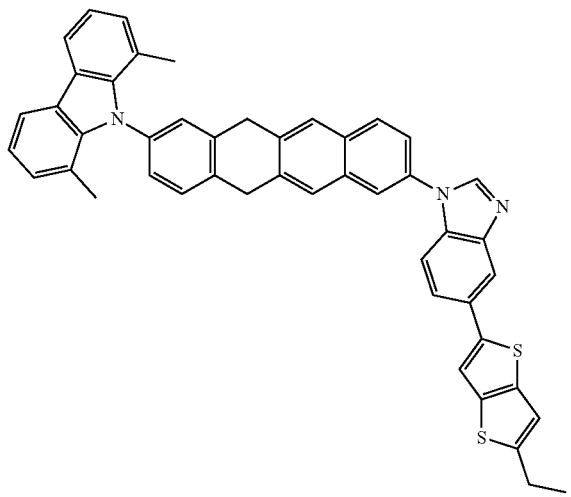
Compound 122
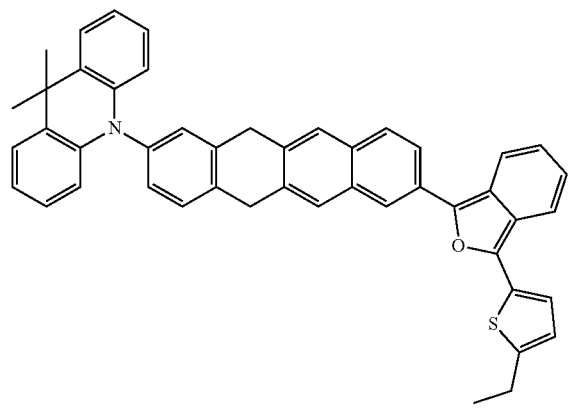
Compound 123
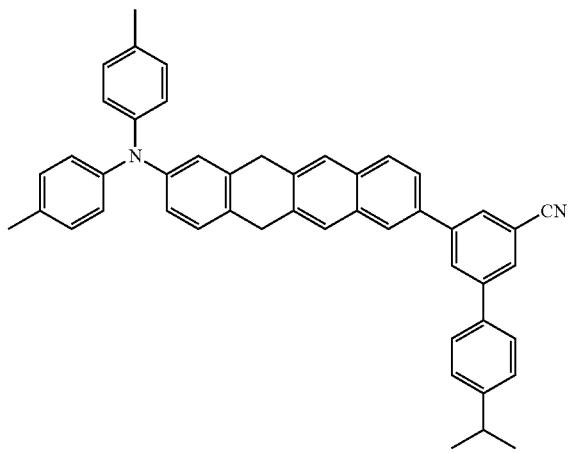
Compound 124
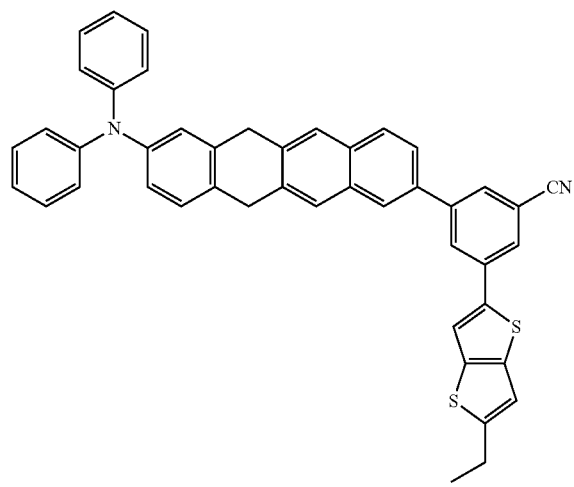

Compound 125
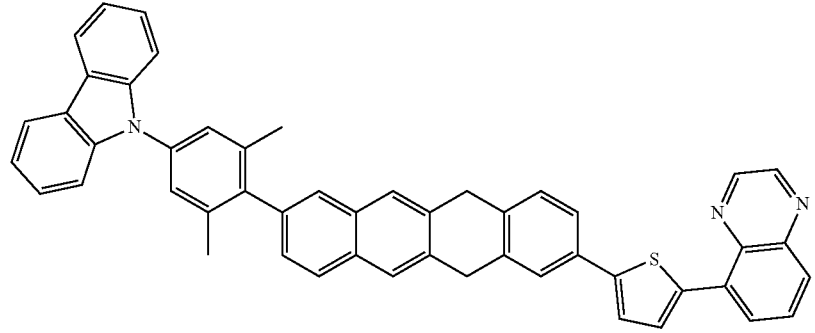
Compound 126
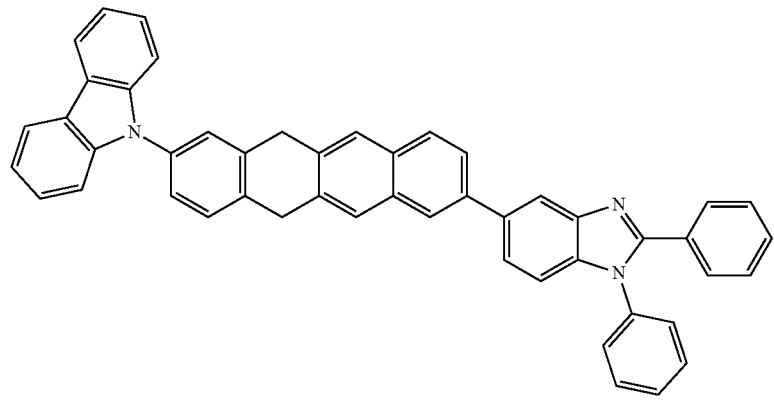
Compound 127
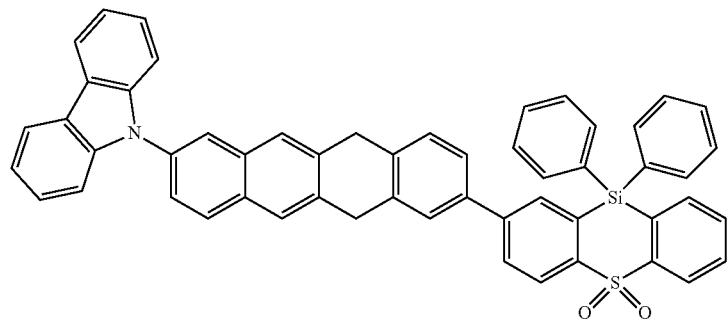
Compound 128
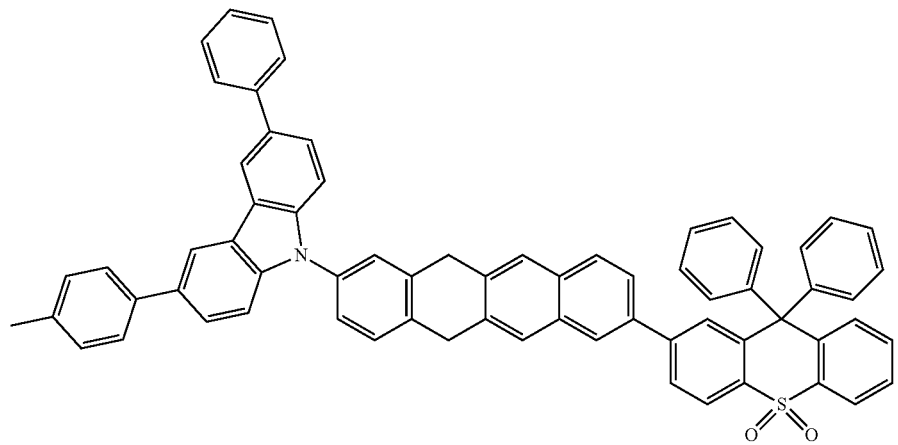

-continued
Compound 129
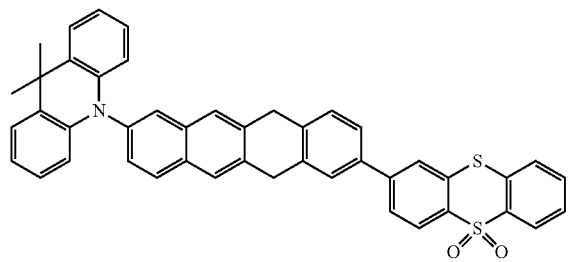
Compound 130
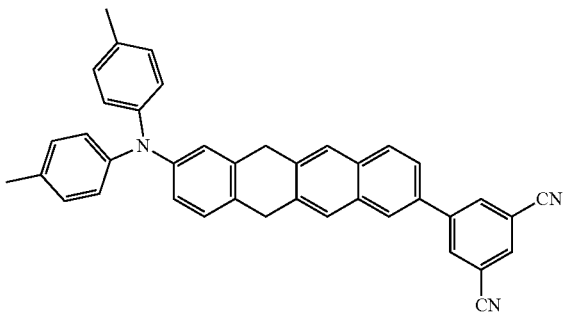
Compound 131
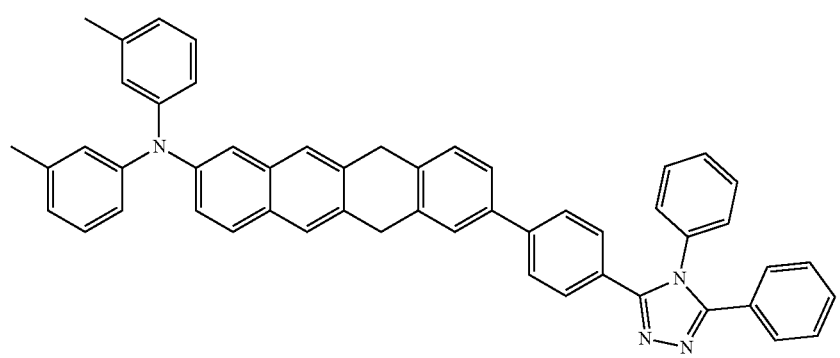
Compound 132
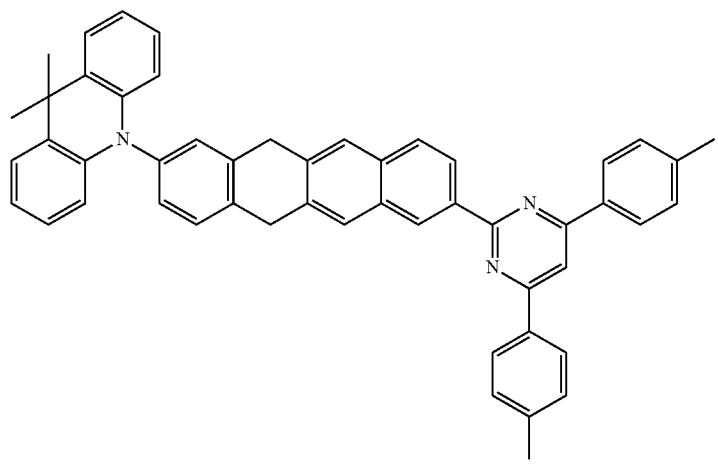
Compound 133
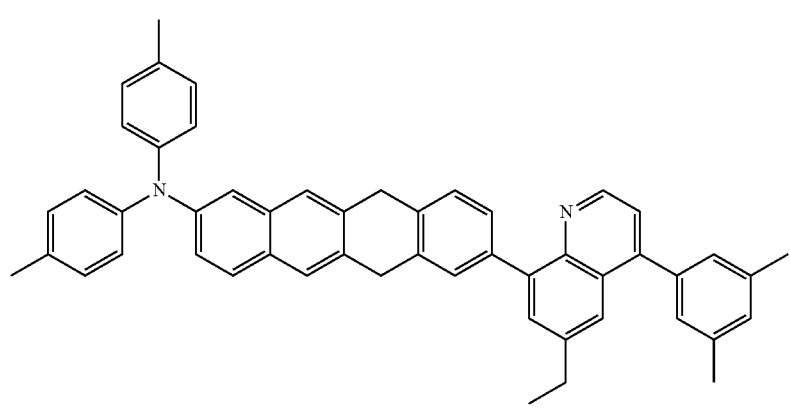

Compound 134
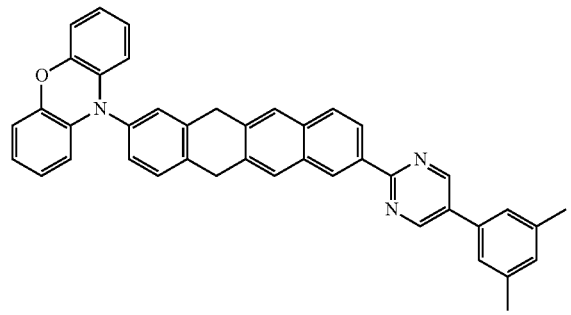
Compound 135
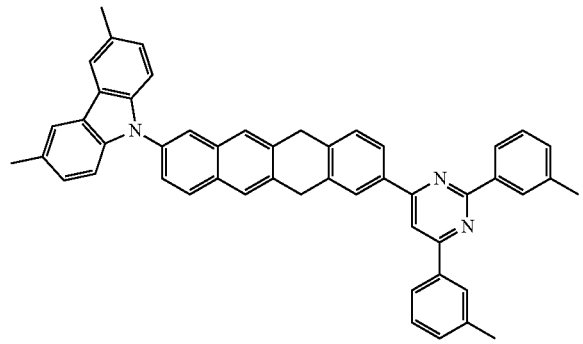
Compound 136
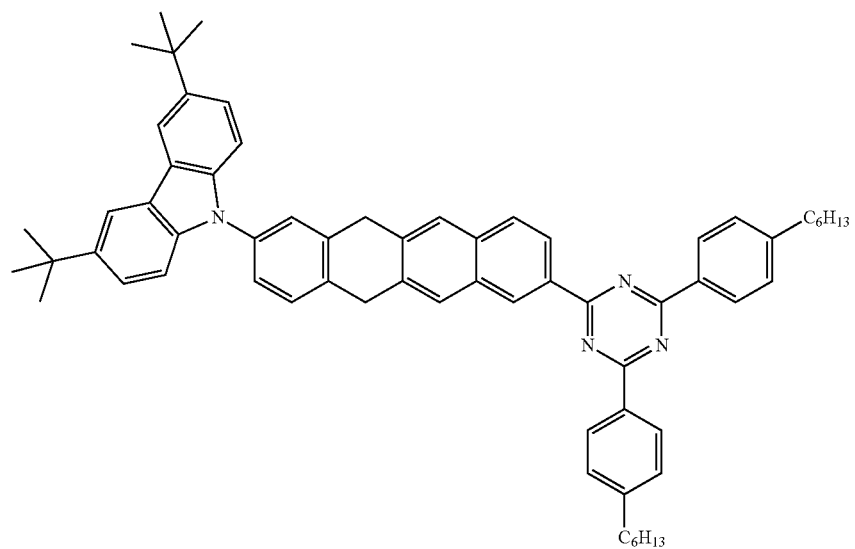
Compound 137
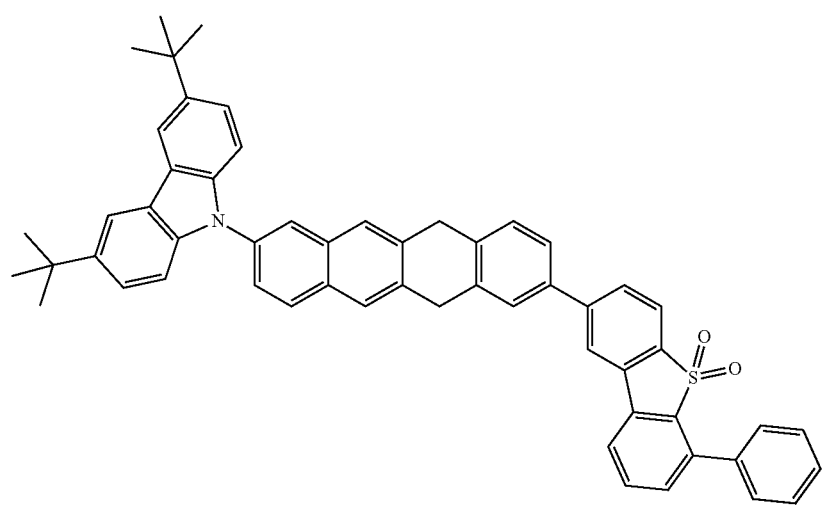

Compound 138
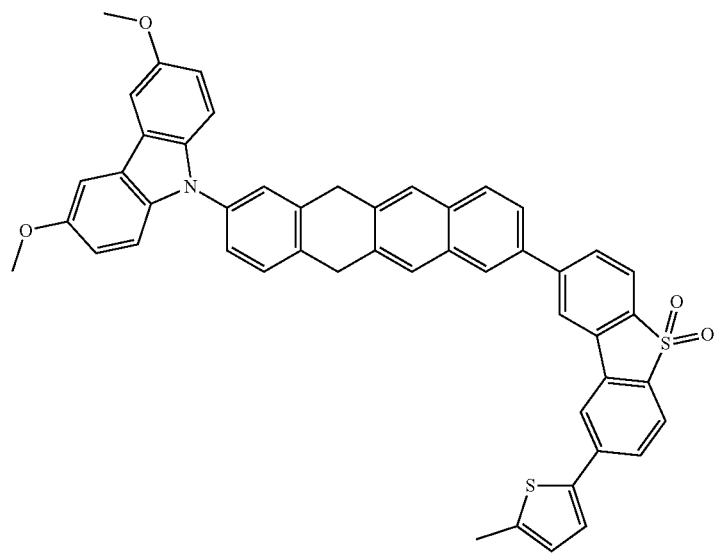
Compound 139
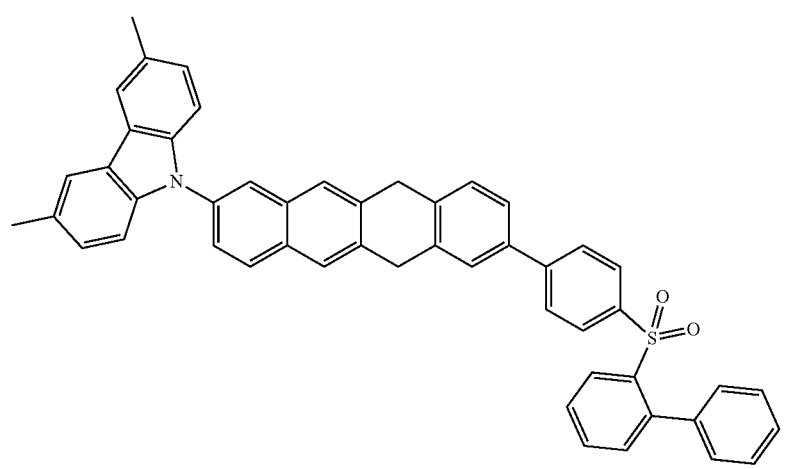
Compound 140
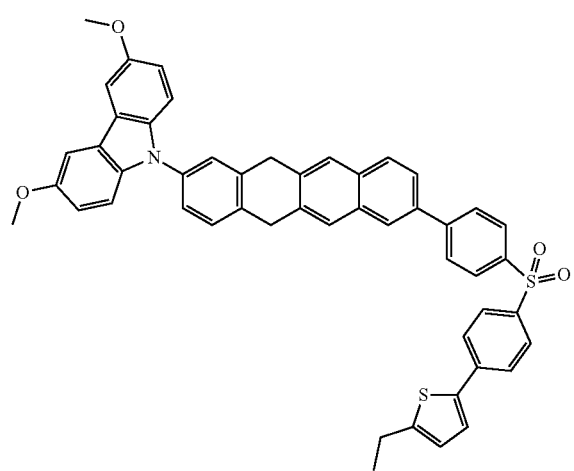
Compound 141
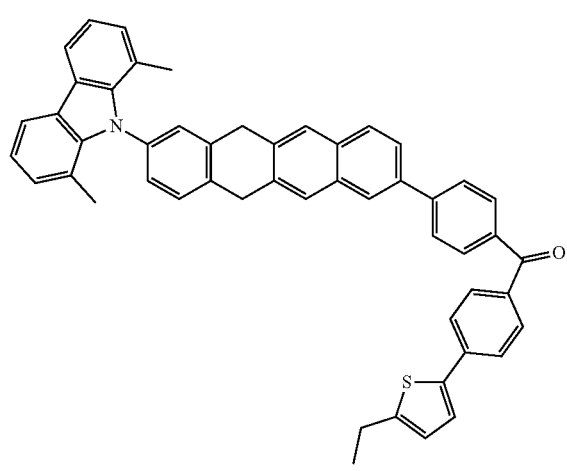

-continued
Compound 142
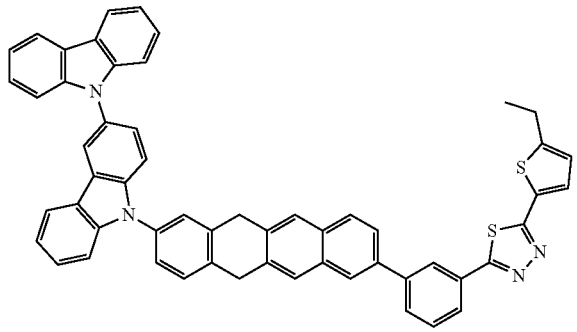
Compound 143
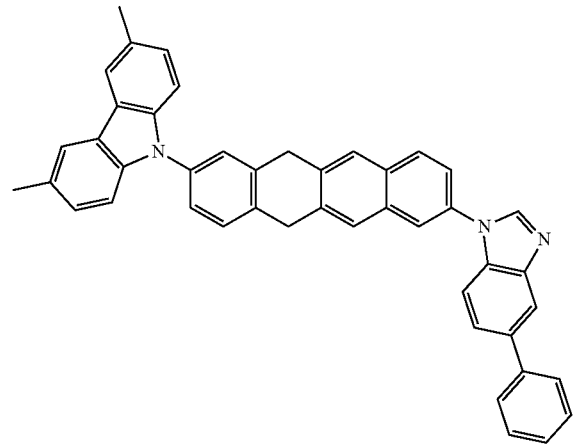
Compound 144
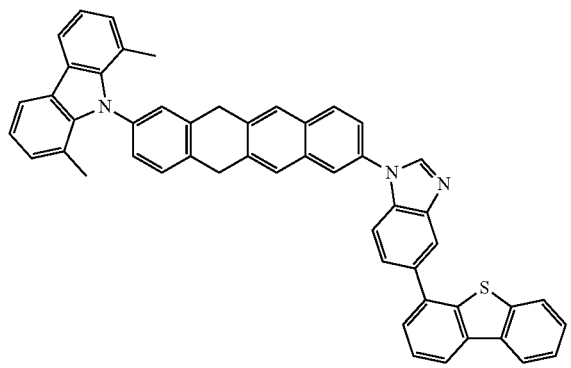
Compound 145
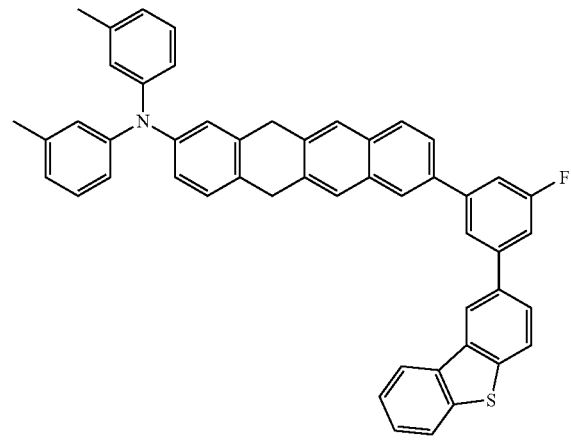
Compound 146
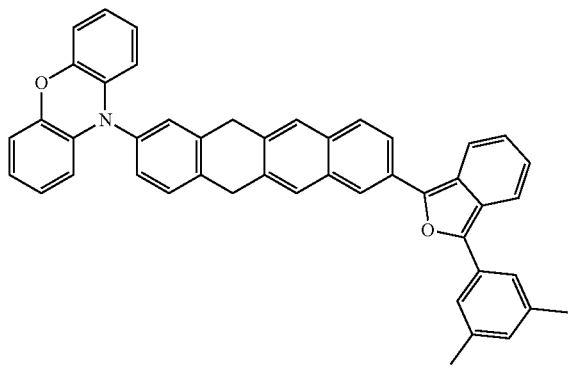
Compound 147
Compound 148
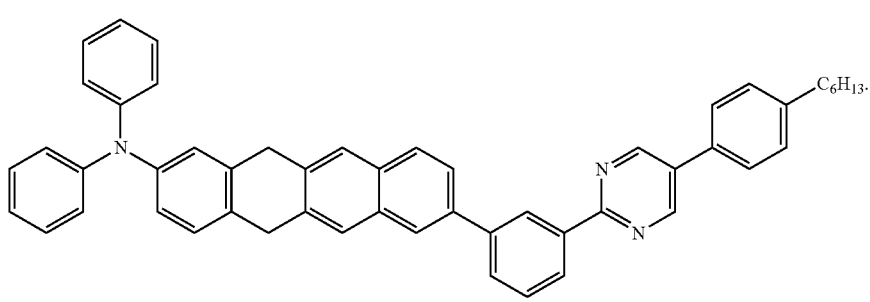

3. An organic electroluminescence device, comprising a pair of electrodes composed of a cathode and an anode, and a light emitting layer between the pair of electrodes, wherein the light emitting layer comprises the 5,12-dihydrotetracene derivative according to claim 1.

4. The organic electroluminescence device according to claim 3, wherein the light emitting layer comprising the 5,12-dihydrotetracene derivative is a thermally activated delayed fluorescence host material.

5. The organic electroluminescence device according to claim 4, wherein the light emitting layer further comprises a second fluorescence host material.

6. The organic electroluminescence device according to claim 3, wherein the light emitting layer comprising the 5,12-dihydrotetracene derivative is a thermally activated delayed fluorescence dopant material.

7. The organic electroluminescence device according to claim 6, wherein the light emitting layer further comprises a second fluorescence dopant material.

8. The organic electroluminescence device according to claim 3, wherein the organic electroluminescence device is a lighting panel.

9. The organic electroluminescence device according to claim 3, wherein the organic electroluminescence device is a backlight panel.

* * * * *